(12) United States Patent
Kas

(10) Patent No.: US 9,791,457 B2
(45) Date of Patent: Oct. 17, 2017

(54) BIOMARKERS FOR HYPERTENSIVE DISORDERS OF PREGNANCY

(71) Applicant: MyCartis NV, Ghent (BE)

(72) Inventor: Koen Kas, Schilde (BE)

(73) Assignee: MYCARTIS NV, Ghent (BE)

( * ) Notice: Subject to any disclaimer, the term of this patent is extended or adjusted under 35 U.S.C. 154(b) by 0 days.

(21) Appl. No.: 14/931,524

(22) Filed: Nov. 3, 2015

(65) Prior Publication Data

US 2016/0054330 A1  Feb. 25, 2016

Related U.S. Application Data

(63) Continuation of application No. 13/085,805, filed on Apr. 13, 2011, now abandoned.

(60) Provisional application No. 61/323,490, filed on Apr. 13, 2010.

(51) Int. Cl.
   *G01N 33/68* (2006.01)
   *C40B 20/04* (2006.01)

(52) U.S. Cl.
   CPC .......... *G01N 33/689* (2013.01); *C40B 20/04* (2013.01); *G01N 2333/47* (2013.01); *G01N 2800/368* (2013.01); *G01N 2800/52* (2013.01)

(58) Field of Classification Search
   None
   See application file for complete search history.

(56) References Cited

U.S. PATENT DOCUMENTS

| | | |
|---|---|---|
| 2006/0134654 A1 | 6/2006 | Wewer et al. |
| 2007/0178605 A1 | 8/2007 | Mor et al. |
| 2008/0090305 A1 | 4/2008 | Day et al. |
| 2008/0233583 A1 | 9/2008 | Fisher et al. |
| 2009/0136971 A1 | 5/2009 | Krizman et al. |
| 2009/0258002 A1 | 10/2009 | Barrett et al. |
| 2011/0251094 A1 | 10/2011 | Kas |
| 2011/0281801 A1* | 11/2011 | Stewart ............. G01N 33/689 514/12.7 |
| 2012/0077209 A1 | 3/2012 | Chance et al. |
| 2012/0142559 A1 | 6/2012 | Tuytten et al. |
| 2013/0045889 A1 | 2/2013 | Kas |
| 2013/0116151 A1 | 5/2013 | Kas |

FOREIGN PATENT DOCUMENTS

| | | |
|---|---|---|
| CN | 101163970 A | 4/2008 |
| CN | 101517078 A | 8/2009 |
| KR | 10-2010-0088217 | 8/2010 |
| WO | WO 2007/092353 | 8/2007 |
| WO | WO 2009/097584 | 8/2009 |
| WO | WO 2010/086380 | 8/2010 |
| WO | WO 2011/128357 A2 | 10/2011 |

OTHER PUBLICATIONS

Wagner et al. Diagnosis and Management of Preeclampsia. Dec. 15, 2004. vol. 70, No. 12, pp. 2317-2324.*
Atkinson, "Proteomic Biomarker Discovery for Preeclampsia," Thesis submitted in partial fulfillment of the requirements for the degree of Doctor of Philosophy in Biological Sciences, The University of Auckland, Jan. 1, 2008, pp. 1-241.
Gerszten et al., "The search for new cardiovascular biomarkers," Nature, vol. 451(7181), pp. 949-952 (Feb. 21, 2008).
International Search Report and Written Opinion for International Application No. PCT/EP2011/071978, dated Jan. 21, 2013, in 22 pages.
International Search Report dated Dec. 30, 2011, issued to priority international application No. PCT/EP2011/061565.
International Search Report dated Oct. 17, 2011, issued to priority international application No. PCT/EP2011/055768.
Kaaja, "Predictors and risk factors of pre-eclampsia," Minerva Ginecologica, vol. 60(5), pp. 421-429 (Oct. 2008).
Lewitt et al., "Developmental Regulation of Circulating Insulin-like Growth Factor-binding Proteins in Normal Pregnancies and in Pre-eclampsia," Progress in Growth Factor Research, vol. 6(2-4), pp. 475-480 (1995).
Lewitt et al., "Regulation of insulin-like growth factor-binding protein-3 ternary complex formation in pregnancy," Journal of Endocrinology, vol. 159(2), pp. 265-274 (1998).
Liu et al., "Pre-eclampsia is associated with the failure of melanoma cell adhesion molecule (MCAM/CD146) expression by intermediate trophoblast," Laboratory Investigation, vol. 84, pp. 221-228 (2004).
Lopez-Novoa, J. Nephrology Dial Transplant, 2007, 22, pp. 712-714.
Mori et al., Biology of Reproduction, 2006, 76, pp. 164-172.
Park et al., "Discovery of the serum biomarker proteins in severe preeclampsia by proteomic analysis," Experimental and Molecular Medicine, vol. 43(7), pp. 427-435 (Jul. 2011).
Portes et al. "Tissue Distribution of Quiescin Q6/sulfhydryl Oxidase (QSOX) in Developing Mouse," Journal of Molecular Histology, vol. 39, No. 2, pp. 217-225 (2008).
Rayman, "Selenoproteins and human health: Insights from epidemiological data," Biochimica et Biophysica Acta, vol. 1790, pp. 1533-1540 (2009).
Sibai et al. Am J. Obstet Gynec, Feb. 1995, 2(1 ), pp. 642-648.
Wang et al. New England Journal of Medicine, 2006, 355(25), pp. 2631-2639.

* cited by examiner

*Primary Examiner* — Channing S Mahatan
(74) *Attorney, Agent, or Firm* — Knobbe, Martens, Olson & Bear LLP

(57) ABSTRACT

The application discloses new biomarkers for hypertensive disorders of pregnancy and particularly preeclampsia; methods for the diagnosis, prediction, prognosis and/or monitoring said disorders based on measuring said biomarkers; and kits and devices for measuring said biomarker and/or performing said methods.

11 Claims, 15 Drawing Sheets

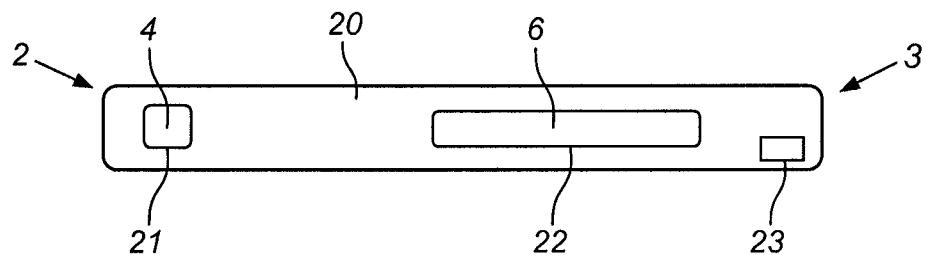
Fig. 15
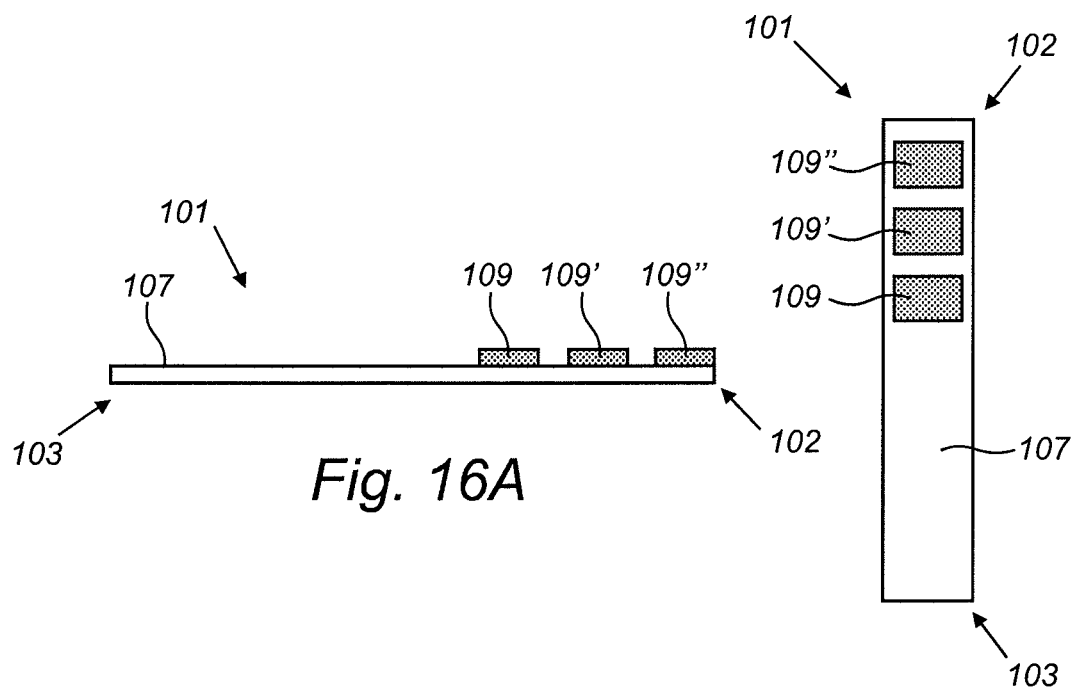
Fig. 16A
Fig. 16B

BIOMARKERS FOR HYPERTENSIVE DISORDERS OF PREGNANCY

RELATED APPLICATIONS

This application is a continuation of U.S. application Ser. No. 13/085,805, filed Apr. 13, 2011 which claims priority to U.S. provisional application No. 61/323,490 filed Apr. 13, 2010. Both applications are incorporated herein by reference.

SEQUENCE LISTING

This application includes a sequence listing as an Appendix

FIELD OF THE INVENTION

The invention relates to biomarkers, particularly protein- and/or peptide-based biomarkers, useful for the diagnosis, prediction, prognosis and/or monitoring of diseases and conditions in subjects, in particular hypertensive disorders of pregnancy, more in particular preeclampsia; and to related methods, uses, kits and devices.

BACKGROUND OF THE INVENTION

In many diseases and conditions, a favourable outcome of prophylactic and/or therapeutic treatments is strongly correlated with early and/or accurate prediction, diagnosis, prognosis and/or monitoring of a disease or condition. Therefore, there exists a continuous need for additional and preferably improved manners for early and/or accurate prediction, diagnosis, prognosis and/or monitoring of diseases and conditions to guide the treatment choices.

Hypertensive disorders occurring during pregnancy represent a major cause of maternal morbidity and mortality worldwide, and are also associated with increased perinatal mortality.

A prominent place among hypertensive disorders of pregnancy belongs to preeclampsia (PE), which develops in about 5% to 10% of pregnant females (Solomon & Seely 2006, Endocrinol Metab Clin North Am 35(1): 157-71, vii).

PE may be described as new onset hypertension and proteinuria past 20 weeks gestation in a previously normotensive pregnant female, which may be mild or severe. Patients with mild disease display blood pressures >140/90 and proteinuria with >300 mg protein noted on a 24 hour urine after 20 weeks gestation, and usually deliver near term without significant co-morbidities. However, about 25% of PE tends to be severe, involving symptoms and signs of central nervous system dysfunction, hepatocellular injury, reduced urine output and markedly elevated blood pressure (systolic >160 mmHg or diastolic >110 mmHg). Severe PE typically occurs in late $2^{nd}$ and early $3^{rd}$ trimester and is associated with increased maternal and perinatal morbidity and mortality.

Severe complications of PE include 1) HELLP syndrome characterised by haemolysis, elevated liver enzymes and low platelets, and 2) eclampsia characterised by the development of seizures. Whereas both these conditions are rare, they are associated with poor prognosis (Solomon & Seely 2006, supra).

Preeclampsia is also associated with foetal complications such as intrauterine growth retardation (IUGR) and small for gestational age (SGA).

The only cure for PE is delivery of the baby and placenta. Beyond 37 weeks of gestation, delivery is warranted. At gestational ages of less than 34 weeks, treatment of hypertension and close foetal surveillance may prevent cerebral vascular accidents and prolong the pregnancy, without curing the underlying disease process. Delivery is also warranted for development of severe PE or eclampsia (Sibai & Barton 2007, Am J Obstet Gynecol 196(6):514.e1-9).

The aetiology and pathophysiology of PE remains largely unresolved and its diagnosis is currently based entirely on clinical criteria once the disease unfolds (Roberts et al. 2003, Hypertension 41(3): 37-45). However, recent data suggests that events leading to PE may begin and progress insidiously as early as $1^{st}$ trimester.

Dependable and early prediction and/or diagnosis is therefore crucial for successful treatment interventions in hypertensive disorders of pregnancy including inter alia PE. Consequently, provision of further, alternative and preferably improved markers and tools for diagnosis, prediction, prognosis and/or monitoring of hypertensive disorders of pregnancy continues to be of prime importance.

Clinically useful screening tests to predict the development of PE are sparse (Conde-Agudelo et al. 2004, Obstet Gynecol 104: 1367-91). Reliance on risk factors is also substandard, since (although several risk factors for PE have been identified) over 50% of cases occur among otherwise young, low risk, nulliparous females. Hence, hypertensive disorders of pregnancy and particularly PE remain largely unpredictable in their onset and disease progression.

Recent reports suggested that an imbalance of vasoactive placental peptides, more specifically soluble fms-like tyrosine kinase-1 (sFlt-1, sVEGFR-1) (Maynard et al. 2003, J Clin Invest 111(5): 649-58), endoglin (Levine et al. 2006, N Engl J Med 355: 992-1005), placental growth factor (PlGF) and vascular endothelial growth factor (VEGF) (Polliotti et al. 2003; Obstet Gynecol 101: 1266-74), may be useful in early prediction of preeclampsia. In particular, sFlt-1 and endoglin are anti-angiogenic peptides produced in excess about 2-3 months prior to development of PE. PlGF and VEGF are pro-angiogenic peptides shown to be reduced in $2^{nd}$ trimester maternal sera of females who subsequently develop severe PE.

WO2009/097584A1 to Proteogenix Inc. and WO2009/108073A1 to Auckland Uniservices Ltd also disclose PE biomarkers.

The present invention addresses the above needs in the art by identifying biomarkers for hypertensive disorders of pregnancy, particularly for preeclampsia, and providing uses therefore.

SUMMARY OF THE INVENTION

Having conducted extensive experiments and tests, the inventors identified 33 biomarkers whose levels are closely predictive and/or indicative of hypertensive disorders of pregnancy, more specifically preeclampsia. For sake of conciseness, hypertensive disorder(s) of pregnancy and preeclampsia is/are henceforth abbreviated respectively as HDP and PE throughout this specification.

In particular, using 1) samples obtained at 22 weeks and 26 weeks of gestation from 10 pregnant women (cases) who would develop clinically manifest PE as from 28 weeks of gestation or later, and 2) samples obtained at 22 weeks and 26 weeks of gestation from pregnant women (controls) who would not develop PE during their pregnancy, the inventors realised that the quantity of the following protein- and/or peptide-based markers in said samples displayed a behaviour predictive and/or indicative of PE: insulin-like growth factor-binding protein complex acid labile chain (ALS), disintegrin and metalloproteinase domain-containing protein 12 (ADA12), angiogenin, (ANGI), calpain-1 catalytic subunit (CAN1), macrophage colony-stimulating factor 1 receptor (CSF1R), C-reactive protein (CRP), chorionic somatomammotropin hormone (CSH), dystroglycan (DAG1), dipeptidase 2 (DPEP2), desmoglein-2 (DSG2), extracellular matrix protein 1 (ECM1), endoglin (EGLN), ectonucleotide pyrophosphatase/phosphodiesterase family member 2 (ENPP2), fibulin-1 (FBLN1), fibrillin-2 (FBN2), probable G-protein coupled receptor 126 (GP126), hepatocyte growth factor-like protein (HGFL), intercellular adhesion molecule 3 (ICAM3), metastasis-suppressor KISS-1 (KISS1), leucyl-cystinyl aminopeptidase (LCAP), phosphatidylcholine-sterol acyltransferase (LCAT), basement membrane-specific heparan sulfate proteoglycan core protein (PGBM), N-acetylmuramoyl-L-alanine amidase (PGRP2), phosphatidylinositol-glycan-specific phospholipase D (PHLD), peroxiredoxin 1 (PRDX1), peroxiredoxin 2 (PRDX2), receptor-type tyrosine-protein phosphatase S (PTPRS), roundabout homolog 4 (ROBO4), protein S100-A9 (S10A9), serum amyloid A-4 protein (SAA4), tenascin-X (TENX), trefoil factor 3 (TFF3), vascular endothelial growth factor receptor 3 (VGFR3). These proteins may be encoded respectively by IGFALS, ADAM12, ANG, CAPN1, CSF1R, CRP, CSH, DAG1, DPEP2, DSG2, ECM1, ENG, ENPP2, FBLN1, FBN2, GPR126, MST1, ICAM3, KISS1, LNPEP, LCAT, HSPG2, PGLYRP2, GPLD1, PRDX1/2, PTPRS, ROBO4, S100A9, SAA4, TNXB, TFF3 and FLT4 genes.

Hence, provided is use of any one or more of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 as a biomarker, more particularly as a biomarker for a HDP, even more particularly as a biomarker for the diagnosis, prediction, prognosis and/or monitoring of said HDP. Preferably, said HDP disorder is PE.

Also provided is use of any one or more of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 for the diagnosis, prediction, prognosis and/or monitoring of a HDP. Preferably, said HDP disorder is PE.

Further provided is a method for the diagnosis, prediction, prognosis and/or monitoring of a HDP in a subject comprising measuring the level of any one or more of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in a sample from said subject. Preferably, said HDP disorder is PE.

As used throughout this specification, measuring the levels of any one or more biomarker(s) in a sample from a subject may particularly denote that the examination phase of a method comprises measuring the quantity of said one or more biomarker(s) in the sample from the subject. One understands that methods for the diagnosis, prediction, prognosis and/or monitoring of diseases and conditions generally comprise an examination phase in which data is collected from and/or about the subject.

In an embodiment, a method for the diagnosis, prediction and/or prognosis of a HDP such as preferably PE in the subject comprises the steps of: (i) measuring the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in a sample from the subject; (ii) comparing the quantity of the one or more markers measured in (i) with a reference value of the quantity of said one or more markers, said reference value representing a known diagnosis, prediction and/or prognosis of the HDP; (iii) finding a deviation or no deviation of the quantity of the one or more markers measured in (i) from the reference value; and (iv) attributing said finding of deviation or no deviation to a particular diagnosis, prediction and/or prognosis of the HDP in the subject.

The method for the diagnosis, prediction and/or prognosis of a HDP such as preferably PE, and in particular such method comprising steps (i) to (iv) set forth in the previous paragraph, may be performed for a subject at two or more successive time points and the respective outcomes at said successive time points may be compared, whereby the presence or absence of a change between the diagnosis, prediction and/or prognosis of the HDP at said successive time points is determined. The method thus allows to monitor a change in the diagnosis, prediction and/or prognosis of the HDP in a subject over time.

The quantity of biomarkers as taught herein may vary during pregnancy and/or postpartum. Therefore, to improve the diagnostic, predictive and/or prognostic dependability of the uses and methods taught herein, the quantity of a given marker measured at a given age of gestation or postpartum in the subject under examination is preferably compared to a reference value of the quantity of said marker established at substantially the same age of gestation or postpartum (e.g., within +/−about 3 weeks, preferably within +/−about 2 weeks, more preferably within +/−about 1 week, yet more preferably within +/−about 0.5 week).

One shall also appreciate that a given marker may display its diagnostic, predictive and/or prognostic value when assessed at one or at more than one time points during pregnancy or postpartum. For example, a marker may be informative when evaluated substantially throughout pregnancy and/or postpartum, or only when evaluated within a portion of pregnancy (e.g., within $1^{st}$, $2^{nd}$ and/or $3^{rd}$ trimesters) or postpartum, or only when evaluated within one or more comparably short periods of pregnancy or postpartum (e.g., within a period of about 10, 8, 6, 4 or 2 weeks). All such markers are useful and suitable herein.

Hence, an elevated quantity or a reduced quantity (i.e., a deviation) of any one or more markers chosen from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in a sample from a subject compared to a reference value representing the prediction or diagnosis of no HDP such as preferably no PE (i.e., healthy state) or representing a good prognosis for a HDP such as preferably PE may indicate respectively that the subject has or is at risk of having the HDP or indicates a poor prognosis for the HDP in the subject (such as, e.g., a prognosis that PE will worsen or progress to HELLP syndrome or eclampsia).

By means of example only and without any limitation, (a) an elevated quantity (i.e., a deviation) of any one or more markers chosen from the group consisting of ALS, ADA12, CRP, CSH, DAG1, ENPP2, GP126, ICAM3, KISS1, LCAP, LCAT, PHLD, PRDX1 and/or PRDX2, S10A9, SAA4 and TFF3 and/or (b) a reduced quantity (i.e., a deviation) of any one or more markers chosen from the group consisting of ADA12, ANGI, CAN1, CSF1R, CSH, DAG1, DPEP2, DSG2, ECM1, FBLN1, FBN2, HGFL, ICAM3, LCAP, PGBM, PGRP2, PTPRS, ROBO4, TENX and VGFR3 in a sample from a subject compared to a reference value representing the prediction or diagnosis of no HDP such as preferably no PE (i.e., healthy state) or representing a good prognosis for a HDP such as preferably PE may indicate respectively that the subject has or is at risk of having the HDP or indicates a poor prognosis for the HDP in the subject (such as, e.g., a prognosis that PE will worsen or progress to HELLP syndrome or eclampsia).

As indicated by the experiments, and reflected in the embodiments below by means of example only and without any limitation, preferably in pregnant human females:

the elevation in the quantity of a marker chosen from the group consisting of ALS, CRP, ENPP2, GP126, KISS1, LCAT, PHLD, PRDX1 and/or PRDX2, S10A9, SAA4 and TFF3 vis-à-vis a reference value may be assessed between about 15 and about 23 or 24 weeks of gestation, more preferably between about 18 and about 23 or 24 weeks of gestation, even more preferably between about 20 and about 23 or 24 weeks of gestation, and most preferably at about 22 weeks of gestation; and/or the reduction in the quantity of a marker chosen from the group consisting of ADA12, ANGI, CAN1, CSF1R, CSH, DAG1, DPEP2, DSG2, ECM1, FBLN1, FBN2, HGFL, ICAM3, LCAP, PGBM, PGRP2, PTPRS, ROBO4, TENX and VGFR3 vis-à-vis a reference value may be assessed between about 15 and about 23 or 24 weeks of gestation, more preferably between about 18 and about 23 or 24 weeks of gestation, even more preferably between about 20 and about 23 or 24 weeks of gestation, and most preferably at about 22 weeks of gestation; and/or the elevation in the quantity of a marker chosen from the group consisting of ALS, ADA12, CRP, CSH, DAG1, ENPP2, GP126, ICAM3, KISS1, LCAP, LCAT, PHLD, PRDX1, and/or PRDX2, S10A9, SAA4 and TFF3 vis-à-vis a reference value may be assessed between about 24 or 25 and about 37 weeks of gestation, more preferably between about 24 or 25 and about 34 weeks of gestation, even more preferably between about 24 or 25 and about 30 weeks of gestation, still more preferably between about 24 or 25 and about 28 weeks of gestation and most preferably at about 26 weeks of gestation; and/or the reduction in the quantity of a marker chosen from the group consisting of ANGI, CAN1, CSF1R, DPEP2, DSG2, ECM1, FBLN1, FBN2, HGFL, PGBM, PGRP2, PTPRS, ROBO4, TENX and VGFR3 vis-à-vis a reference value may be assessed between about 24 or 25 and about 37 weeks of gestation, more preferably between about 24 or 25 and about 34 weeks of gestation, even more preferably between about 24 or 25 and about 30 weeks of gestation, still more preferably between about 24 or 25 and about 28 weeks of gestation and most preferably at about 26 weeks of gestation.

The present methods for the diagnosis, prediction, prognosis and/or monitoring of a HDP and preferably PE may also assess two or more biomarkers as taught herein in a subject. Each so-measured biomarker may be evaluated separately and independently, or one may generate a biomarker profile from the quantities of said two or more biomarkers.

Accordingly, disclosed is also a method for the diagnosis, prediction and/or prognosis of a HDP such as preferably PE in a subject comprising the steps: (i) measuring the quantity of any two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in the sample from the subject; (ii) using the measurements of (i) to establish a subject profile of the quantity of the two or more markers; (iii) comparing said subject profile of (ii) to a reference profile of the quantity of said two or more markers, said reference profile representing a known diagnosis, prediction and/or prognosis of the HDP; (iv) finding a deviation or no deviation of the subject profile of (ii) from the reference profile; (v) attributing said finding of deviation or no deviation to a particular diagnosis, prediction and/or prognosis of the HDP.

Applying the method at two or more successive time points allows for monitoring the HDP.

The quantity of biomarkers as taught herein may vary during pregnancy and/or postpartum. Therefore, to improve the diagnostic, predictive and/or prognostic dependability of the uses and methods taught herein, the subject profile of the quantity of two or more markers established at a given age of gestation or postpartum in the subject under examination is preferably compared to a reference profile of the quantity of said two or more markers established at substantially the same age of gestation or postpartum (e.g., within +/−about 3 weeks, preferably within +/−about 2 weeks, more preferably within +/−about 1 week, yet more preferably within +/−about 0.5 week).

One shall also appreciate that a given marker profile may display its diagnostic, predictive and/or prognostic value when assessed at one or at more than one time points during pregnancy or postpartum. For example, a marker profile may be informative when evaluated substantially throughout pregnancy and/or postpartum, or only when evaluated within a portion of pregnancy (e.g., within $1^{st}$, $2^{nd}$ and/or $3^{rd}$ trimesters) or postpartum, or only when evaluated within one or more comparably short periods of pregnancy or postpartum (e.g., within a period of about 10, 8, 6, 4 or 2 weeks). All such marker profiles and the constituting markers are useful and suitable herein.

Hence, a biomarker profile established using the measured quantities of two or more markers as taught herein in a sample from a subject and comprising an elevated quantity or a reduced quantity (i.e., a deviation) of any one or more markers chosen from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 compared to a reference profile representing the prediction or diagnosis of no HDP such as preferably no PE (i.e., healthy state) or representing a good prognosis for a HDP such as preferably PE may indicate respectively that the subject has or is at risk of having the HDP or indicates a poor prognosis for the HDP in the subject (such as, e.g., a prognosis that PE will worsen or progress to HELLP syndrome or eclampsia).

By means of example only and without any limitation, a biomarker profile established using the measured quantities of two or more markers as taught herein in a sample from a subject and comprising (a) an elevated quantity (i.e., a deviation) of any one or more markers chosen from the group consisting of ALS, ADA12, CRP, CSH, DAG1, ENPP2, GP126, ICAM3, KISS1, LCAP, LCAT, PHLD, PRDX1 and/or PRDX2, S10A9, SAA4 and TFF3 and/or (b) a reduced quantity (i.e., a deviation) of any one or more markers chosen from the group consisting of ADA12, ANGI, CAN1, CSF1R, CSH, DAG1, DPEP2, DSG2, ECM1, FBLN1, FBN2, HGFL, ICAM3, LCAP, PGBM, PGRP2, PTPRS, ROBO4, TENX and VGFR3 compared to a reference profile representing the prediction or diagnosis of no HDP such as preferably no PE (i.e., healthy state) or representing a good prognosis for a HDP such as preferably PE may indicate respectively that the subject has or is at risk of having the HDP or indicates a poor prognosis for the HDP in the subject (such as, e.g., a prognosis that PE will worsen or progress to HELLP syndrome or eclampsia).

As indicated by the experiments, and reflected in the embodiments below by means of example only and without any limitation, preferably in pregnant human females:

a biomarker profile comprising the elevation in the quantity of a marker chosen from the group consisting of ALS, CRP, ENPP2, GP126, KISS1, LCAT, PHLD, PRDX1 and/or PRDX2, S10A9, SAA4 and TFF3 vis-à-vis a reference profile may be assessed between about 15 and about 23 or 24 weeks of gestation, more preferably between about 18 and about 23 or 24 weeks of gestation, even more preferably between about 20 and about 23 or 24 weeks of gestation, and most preferably at about 22 weeks of gestation; and/or a biomarker profile comprising the reduction in the quantity of a marker chosen from the group consisting of ADA12, ANGI, CAN1, CSF1R, CSH, DAG1, DPEP2, DSG2, ECM1, FBLN1, FBN2, HGFL, ICAM3, LCAP, PGBM, PGRP2, PTPRS, ROBO4, TENX and VGFR3 vis-à-vis a reference profile may be assessed between about 15 and about 23 or 24 weeks of gestation, more preferably between about 18 and about 23 or 24 weeks of gestation, even more preferably between about 20 and about 23 or 24 weeks of gestation, and most preferably at about 22 weeks of gestation; and/or a biomarker profile comprising the elevation in the quantity of a marker chosen from the group consisting of ALS, ADA12, CRP, CSH, DAG1, ENPP2, GP126, ICAM3, KISS1, LCAP, LCAT, PHLD, PRDX1, and/or PRDX2, S10A9, SAA4 and TFF3 vis-à-vis a reference profile may be assessed between about 24 or 25 and about 37 weeks of gestation, more preferably between about 24 or 25 and about 34 weeks of gestation, even more preferably between about 24 or 25 and about 30 weeks of gestation, still more preferably between about 24 or 25 and about 28 weeks of gestation and most preferably at about 26 weeks of gestation; and/or a biomarker profile comprising the reduction in the quantity of a marker chosen from the group consisting of ANGI, CAN1, CSF1R, DPEP2, DSG2, ECM1, FBLN1, FBN2, HGFL, PGBM, PGRP2, PTPRS, ROBO4, TENX and VGFR3 vis-à-vis a reference profile may be assessed between about 24 or 25 and about 37 weeks of gestation, more preferably between about 24 or 25 and about 34 weeks of gestation, even more preferably between about 24 or 25 and about 30 weeks of gestation, still more preferably between about 24 or 25 and about 28 weeks of gestation and most preferably at about 26 weeks of gestation.

In an embodiment, a method for monitoring a HDP such as preferably PE (or for monitoring the probability of developing a HDP such as preferably PE) comprises the steps of: (i) measuring the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in samples from a subject from two or more successive time points; (ii) comparing the quantity of the one or more markers between the samples as measured in (i); (iii) finding a deviation or no deviation of the quantity of the one or more markers between the samples as compared in (ii); and (iv) attributing said finding of deviation or no deviation to a change in the HDP (or to a change in the probability of developing the HDP) in the subject between the two or more successive time points. The method thus allows to monitor the HDP or the risk of developing the HDP in a subject over time.

In another embodiment, a method for monitoring a HDP such as preferably PE (or for monitoring the probability of developing a HDP such as preferably PE) comprises the steps of: (i) measuring the quantity of any two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in samples from a subject from two or more successive time points; (ii) using the measurements of (i) to establish subject profiles of the quantity of the two or more markers at the two or more successive time points; (iii) comparing the subject profiles as established in (ii); (iv) finding a deviation or no deviation between the subject profiles as compared in (iii); and (v) attributing said finding of deviation or no deviation to a change in the HDP (or to a change in the probability of developing the HDP) in the subject between the two or more successive time points. The method thus allows to monitor the HDP or the risk of developing the HDP in a subject over time.

Without limitation, such successive time points may be about 2 weeks or more apart, preferably about 4 weeks or more apart, e.g., about 6 or 8 weeks apart, or also preferably about 10 weeks or more apart, e.g., about 12 weeks or 15 weeks apart.

Throughout the present disclosure, methods for monitoring any one disease or condition as taught herein can inter alia allow to predict the occurrence of the disease or condition, or to monitor the progression, aggravation, alleviation or recurrence of the disease or condition, or response to treatment or to other external or internal factors, situations or stressors, etc. Advantageously, monitoring methods as taught herein may be applied in the course of a medical treatment of the subject, preferably medical treatment aimed at alleviating the so-monitored disease or condition. Such monitoring may be comprised, e.g., in decision making whether a patient may be discharged, needs a change in treatment or needs further hospitalisation. As intended herein, a reference to monitoring of a disease or condition also specifically includes monitoring of the probability, risk or chance of a subject to develop the disease or condition, i.e., monitoring change(s) in said probability, risk or chance over time.

Similarly, throughout the present disclosure, methods for the prediction or prognosis of any one disease or condition as taught herein can inter alia allow to predict or make a prognosis of the occurrence of the disease or condition, or to predict or make a prognosis of the progression, aggravation, alleviation or recurrence of the disease or condition or response to treatment or to other external or internal factors, situations or stressors, etc.

The inventors further realised that the evaluation of biomarkers as taught herein at successive time points during pregnancy or postpartum may also allow for the diagnosis, prediction and/or prognosis of HDP and preferably PE. For example, where the difference between the quantities of a marker at said successive time points deviates from the difference between the quantities of said marker measured at corresponding time points in women who would not develop HDP or PE, such deviation may indicate that the subject has or is at risk of developing the HDP or PE.

Accordingly, provided is also a method for the diagnosis, prediction and/or prognosis of a HDP such as preferably PE in a subject comprising the steps of: (i) measuring the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in a sample from the subject from a first time point; (ii) measuring the quantity of said one or more markers in a sample from the subject from a successive second time point; (iii) calculating the difference between the quantities of said one or more markers as measured in (i) and (ii); (iv) comparing the difference as calculated in (iii) with a reference value of the difference between the quantity of said one or more markers at said first and second time points, said reference value representing a known diagnosis, prediction and/or prognosis of the HDP; (v) finding a deviation or no deviation of the difference as calculated in (iii) from the reference value; and (iv) attributing said finding of deviation or no deviation to a particular diagnosis, prediction and/or prognosis of the HDP in the subject.

Also disclosed is a method for the diagnosis, prediction and/or prognosis of a HDP such as preferably PE in a subject comprising the steps of: (i) measuring the quantity of any two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in a sample from the subject from a first time point; (ii) using the measurements of (i) to establish a subject profile of the quantity of the two or more markers at said first time point; (iii) measuring the quantity of said two or more markers in a sample from the subject from a successive second time point; (iv) using the measurements of (iii) to establish a subject profile of the quantity of the two or more markers at said second time point; (v) calculating the difference between the subject profiles as established in (ii) and (iv); (vi) comparing the difference as calculated in (v) with a reference profile of the difference between the quantity of said two or more markers at said first and second time points, said reference profile representing a known diagnosis, prediction and/or prognosis of the HDP; (vii) finding a deviation or no deviation of the difference as calculated in (v) from the reference profile; and (viii) attributing said finding of deviation or no deviation to a particular diagnosis, prediction and/or prognosis of the HDP in the subject.

For example, where the difference ($D_S$) calculated between the quantities of a given marker measured in a subject at said first and second time points deviates from the corresponding difference ($D_N$) as observed in normal pregnancies, the deviation may indicate that the subject has or is at risk of having a HDP such as PE. Without limitation, a deviation may be pronounced where $D_S > D_N$ or where $D_S < D_N$ or where $D_S > 0$ whereas $D_N < 0$, or where $D_S < 0$ whereas $D_N > 0$. The difference may be suitable expressed as an arithmetic operation, such as, e.g., subtraction or division (e.g., slope, ratio).

Without limitation, such successive time points may be about 2 weeks or more apart, preferably about 4 weeks or more apart, e.g., about 6 or 8 weeks apart, or also preferably about 10 weeks or more apart, e.g., about 12 weeks or 15 weeks apart.

Also without limitation, the first time point may be between about 15 and about 23 or 24 weeks of gestation, preferably between about 18 and about 23 or 24 weeks of gestation, more preferably between about 20 and about 23 or 24 weeks of gestation, even more preferably at about 22 weeks of gestation. The second time point may be between about 24 or 25 and about 37 weeks of gestation, preferably between about 24 or 25 and about 34 weeks of gestation, more preferably between about 24 or 25 and about 30 weeks of gestation, still more preferably between about 24 or 25 and about 28 weeks of gestation and even more preferably at about 26 weeks of gestation.

Also disclosed is a method to determine whether a subject is or is not (such as, e.g., still is, or is no longer) in need of a therapeutic or prophylactic (preventative) treatment of a HDP such as preferably PE, comprising: (i) measuring the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in the sample from the subject; (ii) comparing the quantity of the one or more markers measured in (i) with a reference value of the quantity of said one or more markers, said reference value representing a known diagnosis, prediction and/or prognosis of the HDP; (iii) finding a deviation or no deviation of the quantity of the one or more markers measured in (i) from said reference value; (iv) inferring from said finding the presence or absence of a need for a therapeutic or prophylactic treatment of the HDP such as preferably PE.

Also disclosed is a method to determine whether a subject is or is not (such as, e.g., still is, or is no longer) in need of a therapeutic or prophylactic (preventative) treatment of a HDP such as preferably PE, comprising: (i) measuring the quantity of any two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in the sample from the subject; (ii) using the measurements of (i) to establish a subject profile of the quantity of the two or more markers; (iii) comparing said subject profile of (ii) to a reference profile of the quantity of said two or more markers, said reference profile representing a known diagnosis, prediction and/or prognosis of the HDP (iv) finding a deviation or no deviation of the subject profile of (ii) from the reference profile; (v) inferring from said finding the presence or absence of a need for a therapeutic or prophylactic treatment of the HDP such as preferably PE.

A treatment may be particularly indicated where the method allows for a conclusion that the subject has or is at risk of having the HDP or has a poor prognosis for the HDP. Without limitation, a patient having HDP upon admission to or during stay in a medical care centre may be tested as taught herein for the necessity of continuing the treatment of said HDP, and may be discharged when such treatment is no longer needed or is needed only to a given limited extent. Exemplary therapeutic and prophylactic treatments of HDP such as PE encompass without limitation anti-hypertensive treatments (using inter alia beta-blockers, calcium channel blockers, vasodilators and/or DOPA decarboxylase inhibitors, such as, e.g., methyldopa, labetalol, acebutolol, metoprolol, pindolol, propranolol, nifedipine, isradipine and/or hydralazine, and/or $MgSO_4$ treatment), abortion, and delivery such as by labour induction or Caesarean section.

The uses and methods involving evaluation of biomarker(s) as taught herein may principally be carried out for a pregnant or postpartum viviparous animal female subject. Preferably said subject is mammalian, more preferably human.

The uses and methods involving evaluation of biomarker(s) as taught herein may be preferably carried out for a pregnant or postpartum human female subject as from any age of gestation and up to about 12 weeks postpartum, such as without limitation:

wherein the pregnant human female subject is about 5 or more weeks of gestation, or about 10 or more weeks of gestation, or preferably about 15 or more weeks of gestation, or more preferably about 20 or more weeks of gestation, e.g., about 21, 22, 23 or 24 weeks of gestation, or even more preferably about 25 or more weeks of gestation, e.g., about 26, 27, 28 or 29 weeks of gestation; and/or wherein the pregnant human female subject is about 40 or less weeks of gestation, e.g., about 39 or 38 weeks of gestation, or about 37 or less weeks of gestation, e.g., about 36 or 35 weeks of gestation, or about 34 or less weeks of gestation, e.g., about 33, 32, 31 or 30 weeks of gestation; and/or wherein the pregnant human female subject is between about 10 weeks and about 40 weeks of gestation, preferably between about 15 weeks and about 37 weeks of gestation, or also preferably between about 20 weeks and 34 weeks of gestation; or wherein the postpartum human female subject is about 12 weeks or less postpartum, e.g., about 11 or 10 weeks postpartum, or about 9 weeks or less postpartum, e.g., about 8 or 7 weeks postpartum, or about 6 weeks or less postpartum, e.g., about 5 or 4 weeks postpartum, or about 3 weeks or less postpartum, e.g., about 2 or 1 weeks postpartum.

Moreover, the present examples show that the biomarkers as taught herein allow to predict a prospective (i.e., future or forthcoming) occurrence of a HDP and preferably PE in pregnant females who, when the biomarkers are being evaluated, do not yet suffer from clinically manifest HDP or PE.

Hence, the uses and methods involving evaluation of biomarker(s) as taught herein may be preferably intended and employed for the prediction of a HDP and preferably PE in subjects, particularly in subjects not having clinically manifest (i.e., active) HDP or PE. Such prediction may preferably indicate a probability, chance or risk that a tested subject will develop clinically manifest HDP or PE, for example within a certain time period or at a given age of gestation or postpartum.

For example, the uses and methods involving evaluation of biomarker(s) as taught herein, and particularly the uses and methods intended to predict a HDP and preferably PE, may be carried out for a pregnant human female subject, wherein the pregnant human female subject is preferably:

about 37 or less weeks of gestation, e.g., about 36 or 35 weeks of gestation, or about 34 or less weeks of gestation, e.g., about 33, 32 or 31 weeks of gestation, or about 30 or less weeks of gestation, e.g., about 29, 28 or 27 weeks of gestation, or preferably about 26 or less weeks of gestation, e.g., about 25, 24 or 23 weeks of gestation, or more preferably about 22 or less weeks of gestation, e.g., about 21 weeks of gestation, or also preferably about 20 or less weeks of gestation, e.g., about 19, 18, 17 or 16 weeks of gestation, or about as well preferably 15 or less weeks of gestation, e.g., about 14, 13, 12, 11 or 10 weeks of gestation; and/or between about 10 weeks and about 37 weeks of gestation, preferably between about 15 weeks and about 34 weeks of gestation, more preferably between about 20 and about 30 weeks of gestation, even more preferably between about 22 and about 26 weeks of gestation; and wherein the pregnant human female subject preferably does not have active HDP or PE, for example the subject does not manifest clinical symptoms and signs allowing the diagnosis of the HDP or PE.

Further disclosed are uses and methods as taught herein whereby gestational or postpartum age of onset and/or time remaining to onset of a HDP such as preferably PE is predicted. Such uses and methods may advantageously compare biomarker quantities or profiles to reference values or reference profiles which represent known gestational or postpartum ages of onset of the HDP and/or known times remaining to onset of the HDP. Any one or more markers chosen from HGFL, PTPRS, ROBO4 and VGFR3 may be particularly useful in this respect.

Further disclosed are uses and methods as taught herein whereby the methods allow discriminate between subjects having or being at risk of having early onset preeclampsia (i.e., clinical manifestation <34 weeks of gestation) vs. preterm PE (i.e., clinical manifestation >34 and <37 weeks of gestation) vs. term PE (i.e., clinical manifestation ≥37 weeks of gestation).

Hence, also disclosed are the present uses and methods employed for the diagnosis, prediction, prognosis and/or monitoring of HDP, wherein the HDP is early onset PE or preterm PE or term PE.

Using the herein disclosed markers for HDP and preferably PE may be particularly useful in subjects known or expected to be at risk of developing HDP or PE. Without limitation risk factors associated with HDP and preferably PE include nulliparity, multiple gestation, prolonged interval between pregnancies, history of HDP or PE in a prior pregnancy or family history of HDP or PE, extremes in age (<20 years and >40 years), obesity, chronic hypertension, chronic renal disease, migraine, headaches, (gestational) diabetes mellitus, polycystic ovarian syndrome, autoimmune disorders such as lupus, rheumatoid arthritis, sarcoidosis or MS, vascular or connective tissue diseases, vitamin D insufficiency, antiphospholipid antibody syndrome or inherited thrombophilia, male partner whose previous partner had HDP or PE, hydrops fetalis and unexplained foetal intrauterine growth restriction.

Hence, the present diagnosis, prediction, prognosis and/or monitoring methods may be preferably employed in subjects and subject populations having one or more such risk factors. In an embodiment, the present diagnosis, prediction, prognosis and/or monitoring methods may preferably further comprise determining the presence or absence and/or level of one or more risk factors for HDP such as preferably PE in the subject.

Any one prediction, diagnosis, prognosis and/or monitoring use or method as taught herein may preferably allow for sensitivity and/or specificity (preferably, sensitivity and specificity) of at least 50%, at least 60%, at least 70% or at least 80%, e.g., ≥85% or ≥90% or ≥95%, e.g., between about 80% and 100% or between about 85% and 95%.

Reference throughout this specification to "diseases and/or conditions" encompasses any such diseases and conditions as disclosed herein insofar consistent with the context of a particular recitation, more specifically but without limitation including hypertensive disorders of pregnancy (HDP) and preferably preeclampsia (PE).

The uses and methods for the diagnosis, prediction, prognosis and/or monitoring of the diseases and conditions taught herein may be used in subjects who have not yet been diagnosed as having such (for example, preventative screening), or who have been diagnosed as having such, or who are suspected of having such (for example, display one or more characteristic signs and/or symptoms), or who are at risk of developing such (for example, genetic predisposition; presence of one or more developmental, environmental or behavioural risk factors). The uses and methods may also be used to detect various stages of progression or severity of the diseases and conditions. The uses and methods may also be used to detect response of the diseases and conditions to prophylactic or therapeutic treatments or other interventions. The uses and methods can furthermore be used to help the medical practitioner in deciding upon worsening, status-quo, partial recovery, or complete recovery of the subject from the diseases and conditions, resulting in either further treatment or observation or in discharge of the patient from a medical care centre.

Also, the uses and methods for the diagnosis, prediction, prognosis and/or monitoring of the diseases and conditions taught herein may be employed for population screening, such as, e.g., screening in a general population or in a population stratified based on one or more criteria, e.g., age, ancestry, occupation, presence or absence of risk factors of the respective diseases and conditions, etc.

In the uses and methods for the prediction, diagnosis, prognosis and/or monitoring of diseases and conditions taught herein, particularly HDP and preferably PE, the measurement of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 may be combined with the assessment of one or more further biomarkers or clinical parameters relevant for the respective diseases and conditions.

Hence, also provided are methods for the diagnosis, prediction, prognosis and/or monitoring of a HDP such as preferably PE in a subject as taught above, further comprising measuring the presence or absence and/or level of one or more such other markers in the sample from the subject. Specifically provided are such methods wherein the examination phase of the methods further comprises measuring the presence or absence and/or quantity of one or more such other markers in the sample from the subject. Any known or yet unknown suitable markers can be used.

A reference throughout this specification to "other (bio) markers" generally encompasses such other markers which are useful for the diagnosis, prediction, prognosis and/or monitoring of the diseases and conditions as disclosed herein. By means of example and not limitation, biomarkers useful in evaluating HDP and preferably PE include soluble fms-like tyrosine kinase-1 (sFlt-1, sVEGFR-1) (Maynard et al. 2003, supra), endoglin (Levine et al. 2006, supra), placental growth factor (PlGF) and vascular endothelial growth factor (VEGF) (Polliotti et al. 2003, supra). Further biomarkers may include those disclosed in WO2009/097584A1 to Proteogenix Inc. and WO2009/108073A1 to Auckland Uniservices Ltd., incorporated by reference herein.

One shall appreciate that the presence or absence and/or quantity of such other biomarkers may be evaluated each separately and independently, or the presence or absence and/or quantity of such other biomarkers may be included within subject profiles or reference profiles established in the methods disclosed herein.

Reference values as employed herein may be established according to known procedures previously employed for other biomarkers. Such reference values may be established either within (i.e., constituting a step of) or external to (i.e., not constituting a step of) the methods as taught herein. Accordingly, any one of the methods taught herein may comprise a step of establishing a reference value for the quantity of one or more markers as taught herein, said reference value representing either (a) a prediction or diagnosis of the absence of the diseases or conditions as taught herein or a good prognosis thereof, or (b) a prediction or diagnosis of the diseases or conditions as taught herein or a poor prognosis thereof.

A further aspect provides a method for establishing a reference value for the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3, said reference value representing:
(a) a prediction or diagnosis of the absence of the diseases or conditions as taught herein or a good prognosis thereof, or
(b) a prediction or diagnosis of the diseases or conditions as taught herein or a poor prognosis thereof,
comprising:
(i) measuring the quantity of said one or more markers in:
 (i a) one or more samples from one or more subjects not having the respective diseases or conditions or not being at risk of having such or having a good prognosis for such, or
 (i b) one or more samples from one or more subjects having the respective diseases or conditions or being at risk of having such or having a poor prognosis for such, and
(ii) storing the quantity of said one or more markers:
 (ii a) as measured in (i a) as the reference value representing the prediction or diagnosis of the absence of the respective diseases or conditions or representing the good prognosis therefore, or
 (ii b) as measured in (i b) as the reference value representing the prediction or diagnosis of the respective diseases or conditions or representing the poor prognosis therefore.

The present methods may otherwise employ reference profiles for the quantity of any one, two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3, and optionally the presence or absence and/or quantity of one or more other biomarkers, which may be established according to known procedures previously employed for other biomarkers. Such reference profiles may be established either within (i.e., constituting a step of) or external to (i.e., not constituting a step of) the present methods. Accordingly, the methods taught herein may comprise a step of establishing a reference profile for the quantity of any one, any two or more markers as taught herein and optionally the presence or absence and/or quantity of one or more other biomarkers, said reference profile representing either (a) a prediction or diagnosis of the absence of the diseases or conditions as taught herein or a good prognosis therefore, or (b) a prediction or diagnosis of the diseases or conditions as taught herein or a poor prognosis therefore.

A further aspect provides a method for establishing a reference profile for the quantity of any one, two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3, and optionally the presence or absence and/or quantity of one or more other biomarkers useful for the diagnosis, prediction, prognosis and/or monitoring of the diseases or conditions as taught herein, said reference profile representing:
(a) a prediction or diagnosis of the absence of the respective diseases or conditions or a good prognosis therefore, or
(b) a prediction or diagnosis of the respective diseases or conditions or a poor prognosis therefore,
comprising:
(i) measuring the quantity of said one, two or more markers as taught herein and the presence or absence and/or quantity of said one or more other biomarkers in:
  (i a) one or more samples from one or more subjects not having the respective diseases or conditions or not being at risk of having such or having a good prognosis for such; or
  (i b) one or more samples from one or more subjects having the respective diseases or conditions or being at risk of having such or having a poor prognosis for such;
(ii)
  (ii a) using the measurements of (i a) to create a profile of the quantity of said one, two or more markers as taught herein and the presence or absence and/or quantity of said one or more other biomarkers; or
  (ii b) using the measurements of (i b) to create a profile of the quantity of said one, two or more markers as taught herein and the presence or absence and/or quantity of said one or more other biomarkers;
(iii)
  (iii a) storing the profile of (ii a) as the reference profile representing the prediction or diagnosis of the absence of the respective diseases or conditions or representing the good prognosis therefore; or
  (iii b) storing the profile of (ii b) as the reference profile representing the prediction or diagnosis of the respective diseases conditions or representing the poor prognosis therefore.

Further provided is a method for establishing a base-line or reference value in a subject, comprising: (i) measuring the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in the sample from the subject at different time points wherein the subject is not suffering from the diseases or conditions as taught herein, and (ii) calculating the range or mean value of the subject, which is the base-line or reference value for said subject. The quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or the presence or absence and/or quantity of the one or more other biomarkers may be measured by any suitable technique such as may be known in the art.

For example, one may employ binding agents capable of specifically binding to the respective biomarkers and/or to fragments thereof. Binding agent may be inter alia an antibody, aptamer, photoaptamer, protein, peptide, peptidomimetic or a small molecule. For instance, one may employ an immunoassay technology or a mass spectrometry analysis method or a chromatography method, or a combination of said methods.

Further disclosed is a kit for the diagnosis, prediction, prognosis and/or monitoring the diseases or conditions as taught herein in a subject, the kit comprising (i) means for measuring the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in a sample from the subject, and optionally and preferably (ii) a reference value of the quantity of said one or more markers or means for establishing said reference value, wherein said reference value represents a known diagnosis, prediction and/or prognosis of the respective diseases or conditions. The kit thus allows one to: measure the quantity of said one or more markers in the sample from the subject by means (i); compare the quantity of said one or more markers measured by means (i) with the reference value of (ii) or established by means (ii); find a deviation or no deviation of the quantity of said one or more markers measured by means (i) from the reference value of (ii); and consequently attribute said finding of deviation or no deviation to a particular diagnosis, prediction and/or prognosis of the respective diseases or conditions in the subject.

A further embodiment provides a kit for the diagnosis, prediction, prognosis and/or monitoring the diseases or conditions as taught herein in a subject, the kit comprising (i) means for measuring the quantity of any one, two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 in a sample from the subject and (ii) optionally, means for measuring the presence or absence and/or quantity of one or more other biomarkers in the sample from the subject, and optionally and preferably (iii) means for establishing a subject profile of the quantity of said one, two or more biomarkers as taught herein and optionally the presence or absence and/or quantity of said one or more other biomarkers, and optionally and preferably (iv) a reference profile of the quantity of said one, two or more biomarkers as taught herein and optionally the presence or absence and/or quantity of said one or more other biomarkers, or means for establishing said reference profile, said reference profile representing a known diagnosis, prediction and/or prognosis of the respective diseases or conditions. Such kit thus allows one to: measure the quantity of any one, two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and optionally the presence or absence and/or quantity of one or more other biomarkers in the sample from the subject by respectively means (i) and (ii); establish (e.g., using means included in the kit or using suitable external means) a subject profile of the quantity of said one, two or more markers as taught herein and the presence or absence and/or quantity of said one or more other biomarkers based on said measurements; compare the subject profile with the reference profile of (iv) or established by means (iv); find a deviation or no deviation of said subject profile from said reference profile; and consequently attribute said finding of deviation or no deviation to a particular diagnosis, prediction and/or prognosis of the respective diseases or conditions in the subject.

The means for measuring the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or the presence or absence and/or quantity of the one or more other biomarkers in the present kits may comprise, respectively, one or more binding agents capable of specifically binding to said one or more marker as taught herein and/or to fragments thereof, and one or more binding agents capable of specifically binding to said one or more other biomarkers. Binding agent may be inter alia an antibody, aptamer, photoaptamer, protein, peptide, peptidomimetic or a small molecule. A binding agent may be advantageously immobilised on a solid phase or support. The present kits may employ an immunoassay technology or mass spectrometry analysis technology or chromatography technology, or a combination of said technologies.

Disclosed is thus also a kit for the diagnosis, prediction, prognosis and/or monitoring the diseases or conditions as taught herein comprising: (a) one or more binding agents capable of specifically binding to any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or to fragments thereof; (b) preferably, a known quantity or concentration of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or a fragment thereof (e.g., for use as controls, standards and/or calibrators); (c) preferably, a reference value of the quantity of said one or more markers, or means for establishing said reference value. Said components under (a) and/or (c) may be suitably labelled as taught elsewhere in this specification.

Also disclosed is a kit for the diagnosis, prediction and/or prognosis the diseases or conditions as taught herein comprising: (a) one or more binding agents capable of specifically binding to any one, two or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or to fragments thereof; (b) optionally one or more binding agents capable of specifically binding to one or more other biomarkers; (c) preferably, a known quantity or concentration of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or a fragment thereof and optionally a known quantity or concentration of said one or more other biomarkers (e.g., for use as controls, standards and/or calibrators); (d) preferably, a reference profile of the quantity of said one, two or more markers as taught herein and optionally of the presence or absence and/or quantity of said one or more other biomarkers, or means for establishing said reference profiles. Said components under (a), (b) and/or (c) may be suitably labelled as taught elsewhere in this specification.

Further disclosed is the use of the kit as described herein for the diagnosis, prediction, prognosis and/or monitoring the diseases or conditions as taught herein.

Also disclosed are reagents and tools useful for measuring any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and optionally the one or more other biomarkers concerned herein.

Hence, disclosed is a protein, polypeptide or peptide array or microarray comprising (a) any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or a fragment thereof, preferably a known quantity or concentration of said one or more marker and/or fragment thereof; and (b) optionally and preferably, one or more other biomarkers, preferably a known quantity or concentration of said one or more other biomarkers.

Also disclosed is a binding agent array or microarray comprising: (a) one or more binding agents capable of specifically binding to any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or to fragments thereof, preferably a known quantity or concentration of said binding agents; and (b) optionally and preferably, one or more binding agents capable of specifically binding to one or more other biomarkers, preferably a known quantity or concentration of said binding agents.

Also disclosed are kits as taught here above configured as portable devices, such as, for example, bed-side devices, for use at home or in clinical settings.

A related aspect thus provides a portable testing device capable of measuring the quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or fragments thereof in a sample from a subject comprising: (i) means for obtaining a sample from the subject, (ii) means for measuring the quantity of said one or more markers and/or fragments in said sample, and (iii) means for visualising the quantity of said one or more markers and/or fragments measured in the sample.

In an embodiment, the means of parts (ii) and (iii) may be the same, thus providing a portable testing device capable of measuring the quantity of said one or more markers and/or fragments thereof in a sample from a subject comprising (i) means for obtaining a sample from the subject; and (ii) means for measuring the quantity of said one or more markers and/or thereof in said sample and visualising the quantity of said one or more markers and/or fragments measured in the sample.

In an embodiment, said visualising means is capable of indicating whether the quantity of said one or more markers and/or fragments in the sample is above or below a certain threshold level and/or whether the quantity of said one or more markers and/or fragments in the sample deviates or not from a reference value of the quantity of said one or more markers and/or fragments, said reference value representing a known diagnosis, prediction and/or prognosis of the diseases or conditions as taught herein. Hence, the portable testing device may suitably also comprise said reference value or means for establishing the reference value.

In an embodiment, the threshold level is chosen such that the quantity of said one or more markers and/or fragments in the sample above or below (depending on the marker and the disease or condition) said threshold level indicates that the subject has or is at risk of having the respective disease or condition or indicates a poor prognosis for such in the subject, and the quantity of said one or more markers and/or fragments in the sample below or above (depending on the marker and the disease or condition) said threshold level indicates that the subject does not have or is not at risk of having the diseases or conditions as taught herein or indicates a good prognosis for such in the subject.

In an embodiment, the portable testing device comprises a reference value representing the prediction or diagnosis of the absence of the diseases or conditions as taught herein or representing a good prognosis for such, or comprises means for establishing said reference value, and an elevated or reduced (depending on the marker and the disease or condition) quantity of any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or fragments thereof in the sample from the subject compared to said reference value indicates that the subject has or is at risk of having the respective disease or condition or indicates a poor prognosis for such in the subject. In another embodiment, the portable testing device comprises a reference value representing the prediction or diagnosis of the diseases or conditions as taught herein or representing a poor prognosis for such, or comprises means for establishing said reference value, and a comparable quantity of said one or more markers and/or fragments as taught herein in the sample from the subject compared to said reference value indicates that the subject has or is at risk of having the respective disease or condition or indicates a poor prognosis for such in the subject.

In a further embodiment, the measuring (and optionally visualisation) means of the portable testing device may comprise a solid support having a proximal and distal end, comprising: —a sample application zone in the vicinity of the proximal end; —a reaction zone distal to the sample application zone; and —a detection zone distal to the reaction zone; —optionally control standards comprising any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or fragments thereof, whereby said support has a capillary property that directs a flow of fluid sample applied in the application zone in a direction from the proximal end to the distal end; and —optionally comprising a fluid source improving the capillary flow of a more viscous sample.

The reaction zone may comprise one or more bands of a specific binding molecules for any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or fragments thereof conjugated to a detection agent, which specific binding molecule conjugate is disposed on the solid support such that it can migrate with the capillary flow of fluid; and wherein the detection zone comprises one or more capture bands comprising a population of marker specific molecule immobilised on the solid support.

The reaction zone may additionally comprise one or more bands of capture specific binding molecules for any one or more markers selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 and/or fragments thereof in an amount sufficient to prevent a threshold quantity of marker specific binding molecule conjugates to migrate to the detection zone. Alternatively, said device additionally comprises means for comparing the amount of captured marker specific binding molecule conjugate with a threshold value.

Other aspects relate to the realisation that markers disclosed herein may be valuable targets for therapeutic and/or prophylactic interventions in diseases and conditions as taught herein, in particular but without limitation including HDP and preferably PE.

Hence, also disclosed herein are any one and all of the following:
(1) an agent that is able to modulate the level and/or the activity of any one or more nucleic acids or proteins selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 for use as a medicament, preferably for use in the treatment of any one disease or condition as taught herein;
(2) use of an agent that is able to modulate the level and/or the activity of said one or more nucleic acids or proteins as defined in (1) above for the manufacture of a medicament for the treatment of any one disease or condition as taught herein; or use of an agent that is able to modulate the level and/or the activity of said one or more nucleic acids or proteins as defined in (1) above for the treatment of any one disease or condition as taught herein;

(3) a method for treating any one disease or condition as taught herein in a subject in need of such treatment, comprising administering to said subject a therapeutically or prophylactically effective amount of an agent that is able to modulate the level and/or the activity of said one or more nucleic acids or proteins as defined in (1) above;

(4) The subject matter as set forth in any one of (1) to (3) above, wherein the agent is able to reduce or increase the level and/or the activity of said one or more nucleic acids or proteins as defined in (1) above.

(5) The subject matter as set forth in any one of (1) to (4) above, wherein said agent is able to specifically bind to said one or more nucleic acids or proteins as defined in (1) above.

(6) The subject matter as set forth in any one of (1) to (5) above, wherein said agent is an antibody or a fragment or derivative thereof; a polypeptide; a peptide; a peptidomimetic; an aptamer; a photoaptamer; or a chemical substance, preferably an organic molecule, more preferably a small organic molecule.

(7) The subject matter as set forth in any one of (1) to (4) above, wherein the agent is able to reduce or inhibit the expression of said one or more nucleic acids or proteins as defined in (1) above, preferably wherein said agent is an antisense agent; a ribozyme; or an agent capable of causing RNA interference.

(8) The subject matter as set forth in any one of (1) to (4) above, wherein said agent is able to reduce or inhibit the level and/or activity of said one or more nucleic acids or proteins as defined in (1) above, preferably wherein said agent is a recombinant or isolated deletion construct of the said one or more proteins as defined in (1) above polypeptide having a dominant negative activity over the native one or more proteins as defined in (1) above.

(9) An assay to select, from a group of test agents, a candidate agent potentially useful in the treatment of any one disease or condition as taught herein, said assay comprising determining whether a tested agent can modulate, such as increase or reduce and preferably reduce, the level and/or activity of said one or more nucleic acids or proteins as defined in (1) above.

(10) The assay as set forth in (9) above, further comprising use of the selected candidate agent for the preparation of a composition for administration to and monitoring the prophylactic and/or therapeutic effect thereof in a non-human animal model, preferably a non-human mammal model, of any one disease or condition as taught herein.

(11) The agent isolated by the assay as set forth in (10) above.

(12) A pharmaceutical composition or formulation comprising a prophylactically and/or therapeutically effective amount of one or more agents as set forth in any one of (1) to (8) or (10) above, or a pharmaceutically acceptable N-oxide form, addition salt, prodrug or solvate thereof, and further comprising one or more of pharmaceutically acceptable carriers.

(13) A method for producing the pharmaceutical composition or formulation as set forth in (12) above, comprising admixing said one or more agents with said one or more pharmaceutically acceptable carriers.

Said condition or disease as set forth in any one of (1) to (13) above may be particularly chosen from HDP and preferably PE.

Also contemplated is thus a method (a screening assay) for selecting an agent capable of specifically binding to any one or more nucleic acids or proteins selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 (e.g., nucleic acid such as, or gene, or protein) comprising: (a) providing one or more, preferably a plurality of, test binding agents; (b) selecting from the test binding agents of (a) those which bind to said one or more nucleic acids or proteins; and (c) counter-selecting (i.e., removing) from the test binding agents selected in (b) those which bind to any one or more other, unintended or undesired, targets.

Binding between test binding agents and said one or more nucleic acids or proteins may be advantageously tested by contacting (i.e., combining, exposing or incubating) said one or more nucleic acids or proteins with the test binding agents under conditions generally conducive for such binding. For example and without limitation, binding between test binding agents and said one or more nucleic acids or proteins may be suitably tested in vitro; or may be tested in host cells or host organisms comprising said one or more nucleic acids or proteins and exposed to or configured to express the test binding agents.

Without limitation, the binding or modulating agents may be capable of binding said one or more nucleic acids or proteins or modulating the activity and/or level of said one or more nucleic acids or proteins in vitro, in a cell, in an organ and/or in an organism.

In the screening assays as set forth in any one of (9) and (10) above, modulation of the activity and/or level of said one or more nucleic acids or proteins by test modulating agents may be advantageously tested by contacting (i.e., combining, exposing or incubating) said one or more nucleic acids or proteins (e.g., gene or protein) with the test modulating agents under conditions generally conducive for such modulation. By means of example and not limitation, where modulation of the activity and/or level of said one or more nucleic acids or proteins results from binding of the test modulating agents to said one or more nucleic acids or proteins, said conditions may be generally conducive for such binding. For example and without limitation, modulation of the activity and/or level of said one or more nucleic acids or proteins by test modulating agents may be suitably tested in vitro; or may be tested in host cells or host organisms comprising said one or more nucleic acids or proteins and exposed to or configured to express the test modulating agents.

As well contemplated are:

any one or more of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 (e.g., nucleic acid such as a gene, or a polypeptide or protein) for use as a medicament, preferably for use in the treatment of any one disease or condition as taught herein;

use of said one or more nucleic acids or proteins for the manufacture of a medicament for the treatment of any one disease or condition as taught herein;

use of said one or more nucleic acids or proteins for the treatment of any one disease or condition as taught herein;

a method for treating any one disease or condition as taught herein in a subject in need of such treatment, comprising administering to said subject a therapeutically or prophylactically effective amount of said one or more nucleic acids or proteins; particularly wherein said condition or disease may be chosen from HDP and preferably PE.

In the herein disclosed aspects and embodiments, such as uses, methods, kits, devices, reagents, etc., the any one or more markers, nucleic acids or proteins may be in a further, preferred alternative selected from the group consisting of ALS, ADA12, ANGI, CAN1, CSF1R, DAG1, DPEP2, DSG2, ECM1, ENPP2, FBLN1, FBN2, GP126, ICAM3, KISS1, LCAT, PGBM, PGRP2, PHLD, PRDX1, PTPRS, ROBO4, S10A9, TENX, TFF3.

In a yet further preferred alternative, particularly where the aspects and embodiments relate to preeclampsia (PE), the any one or more markers, nucleic acids or proteins may be selected from the group consisting of ALS, ADA12, ANGI, CAN1, CSF1R, CRP, DAG1, DPEP2, DSG2, ECM1, ENPP2, FBLN1, FBN2, GP126, ICAM3, KISS1, LCAP, LCAT, PGBM, PGRP2, PHLD, PRDX1, PRDX2, PTPRS, ROBO4, S10A9, TENX, TFF3. The above and further aspects and preferred embodiments of the invention are described in the following sections and in the appended claims. The subject matter of appended claims is hereby specifically incorporated in this specification.

BRIEF DESCRIPTION OF THE DRAWINGS

FIG. 15: Plan view of a test cartridge according to the invention.

FIG. 16 A-B shows a side view and a top view, respectively, of a reagent strip according to the invention comprising several test pads.

DETAILED DESCRIPTION

Figure 1:
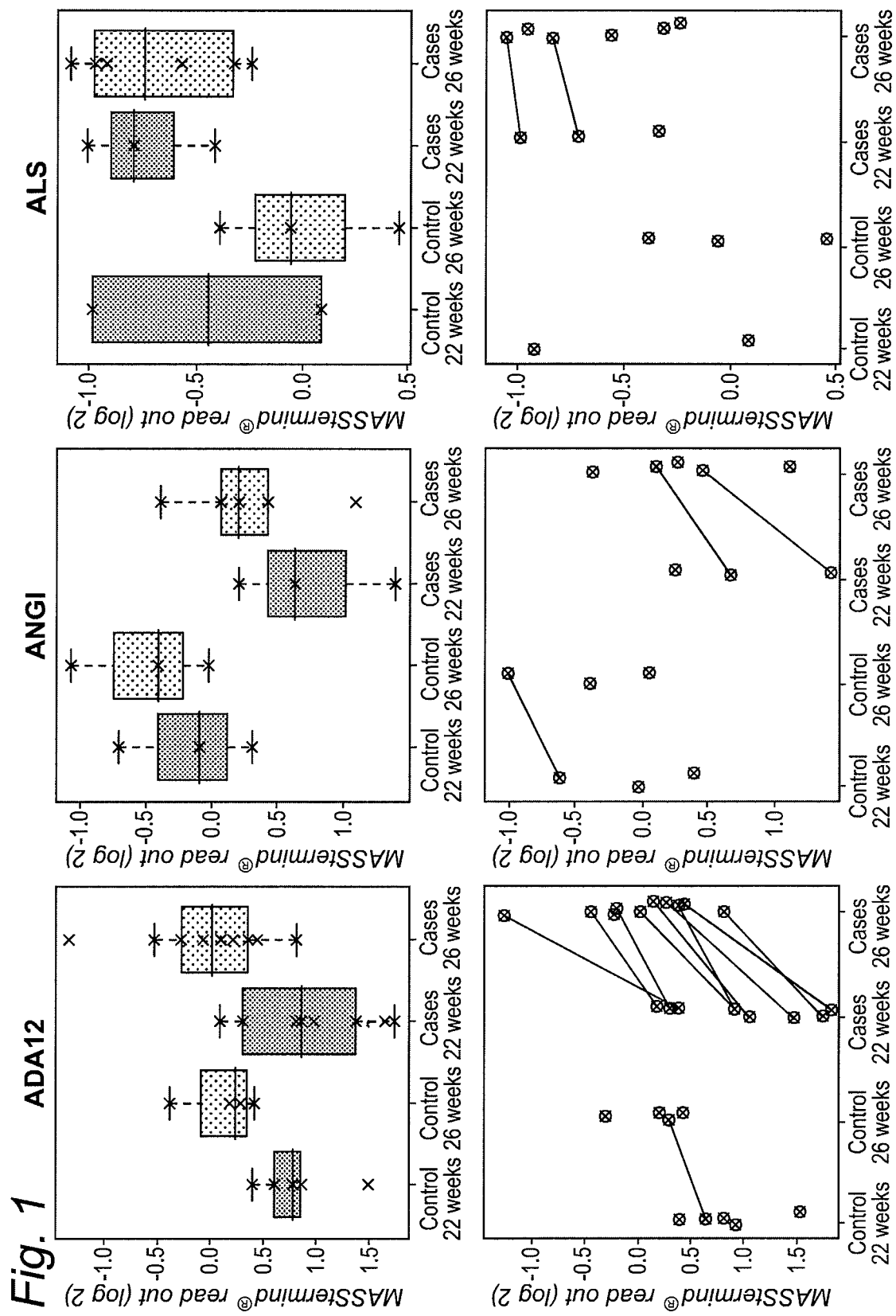
FIGS. 1 to 11 illustrate box and whisker plots for the quantity of the respective markers in cases (i.e., women that would develop PE later during pregnancy) vs. controls (i.e., women that would not develop PE later during pregnancy) at 22 weeks and 26 weeks gestation age.
Figure 2:
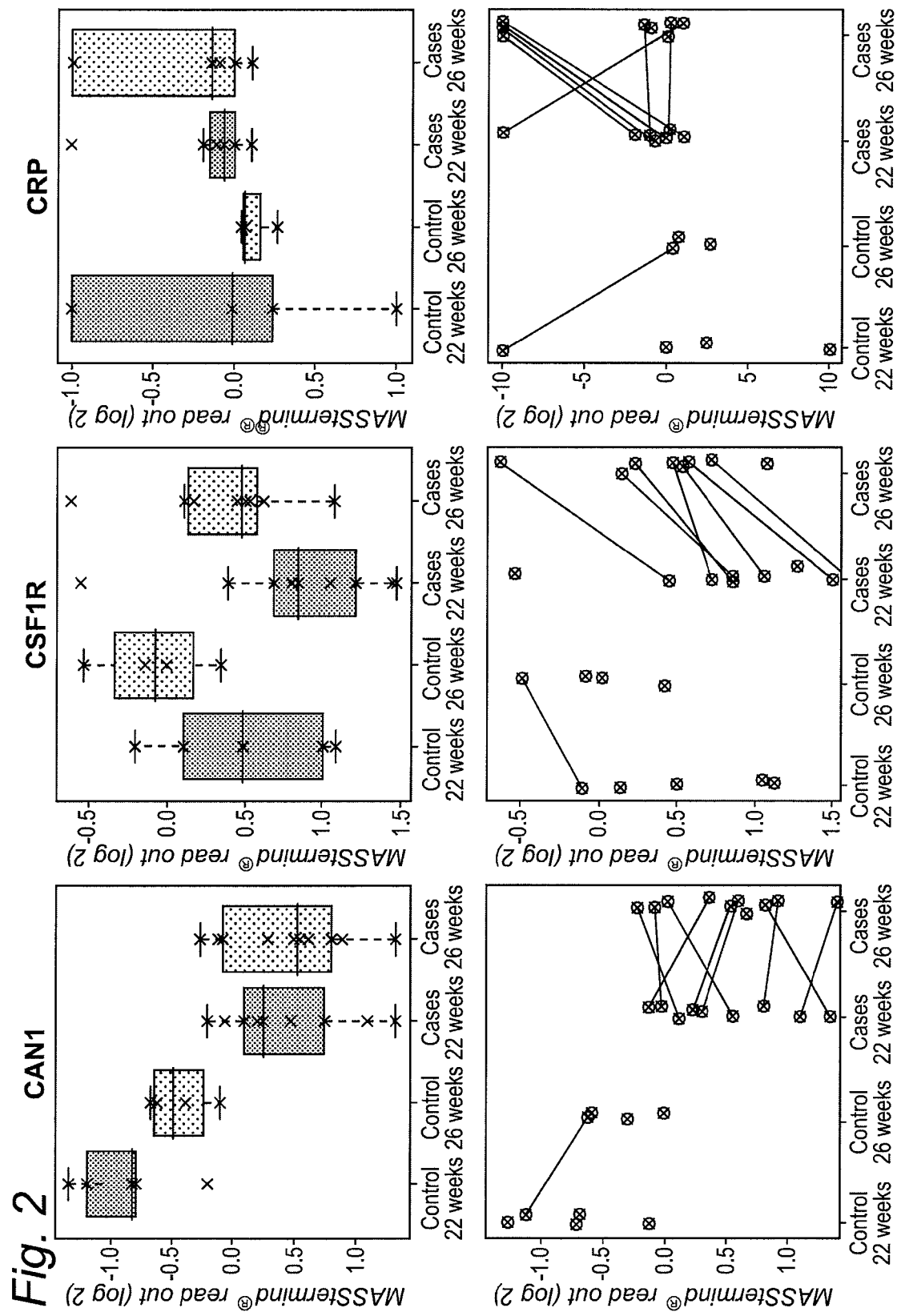
Figure 3:
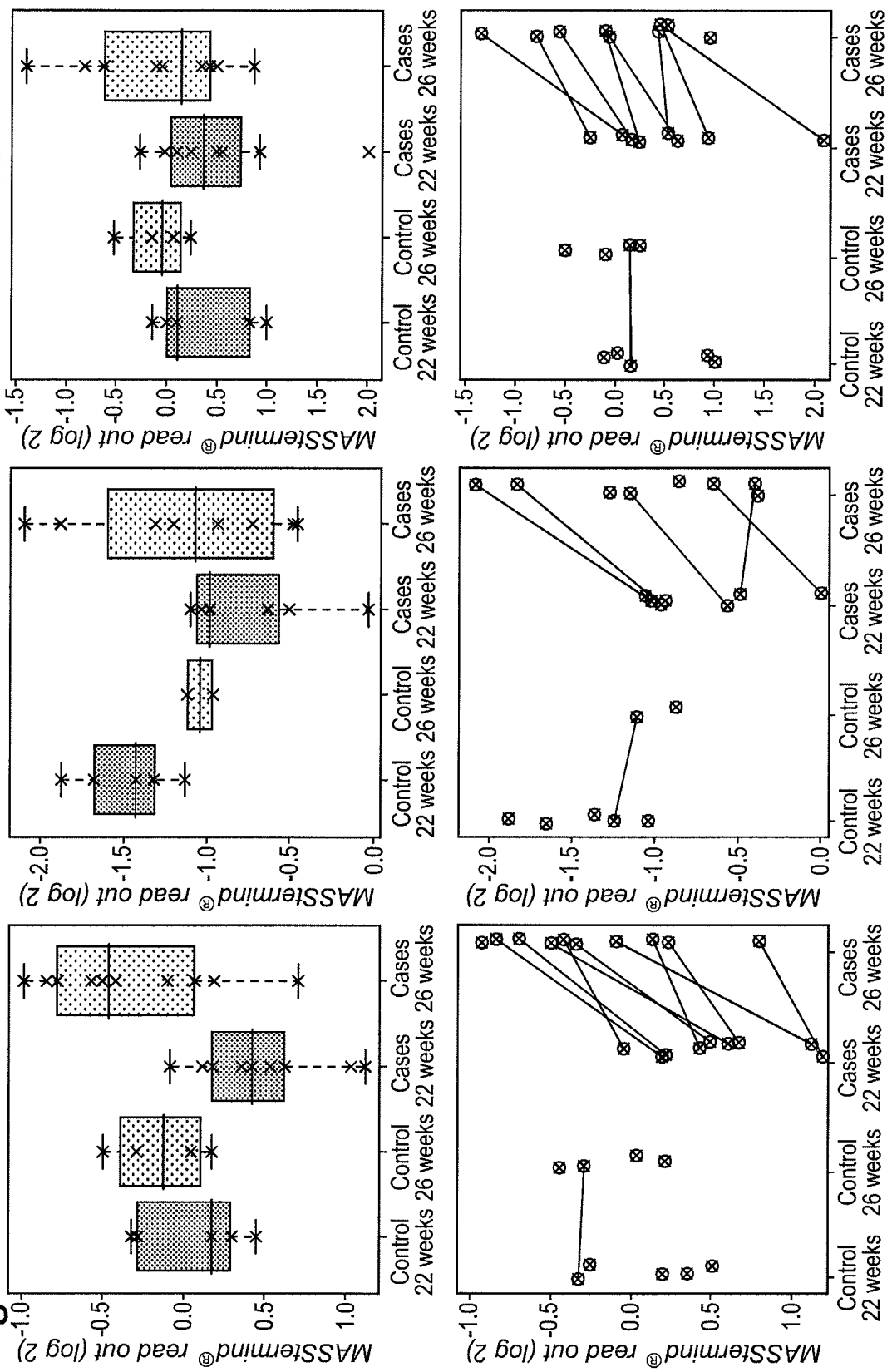
Figure 4:
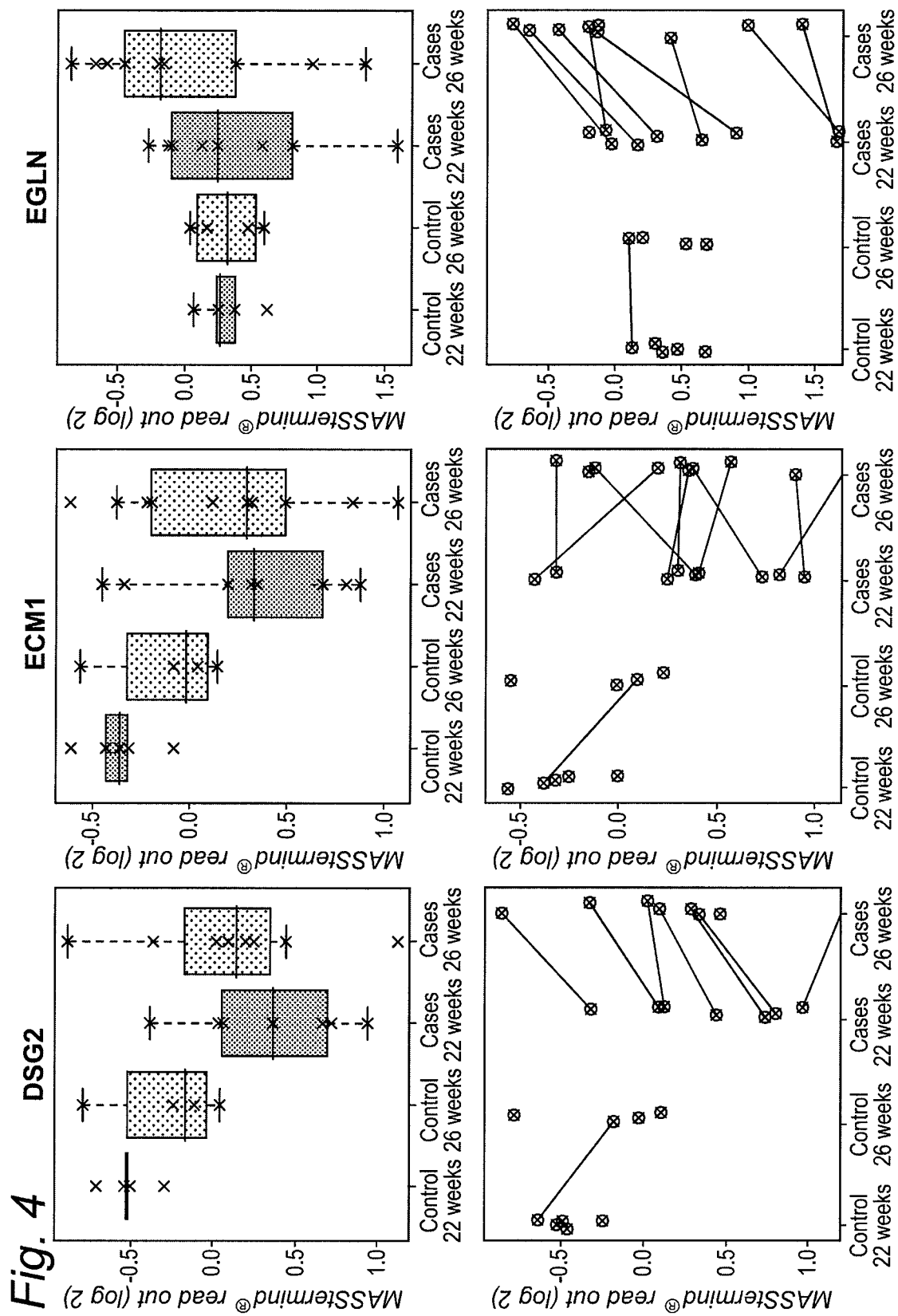
Figure 5:
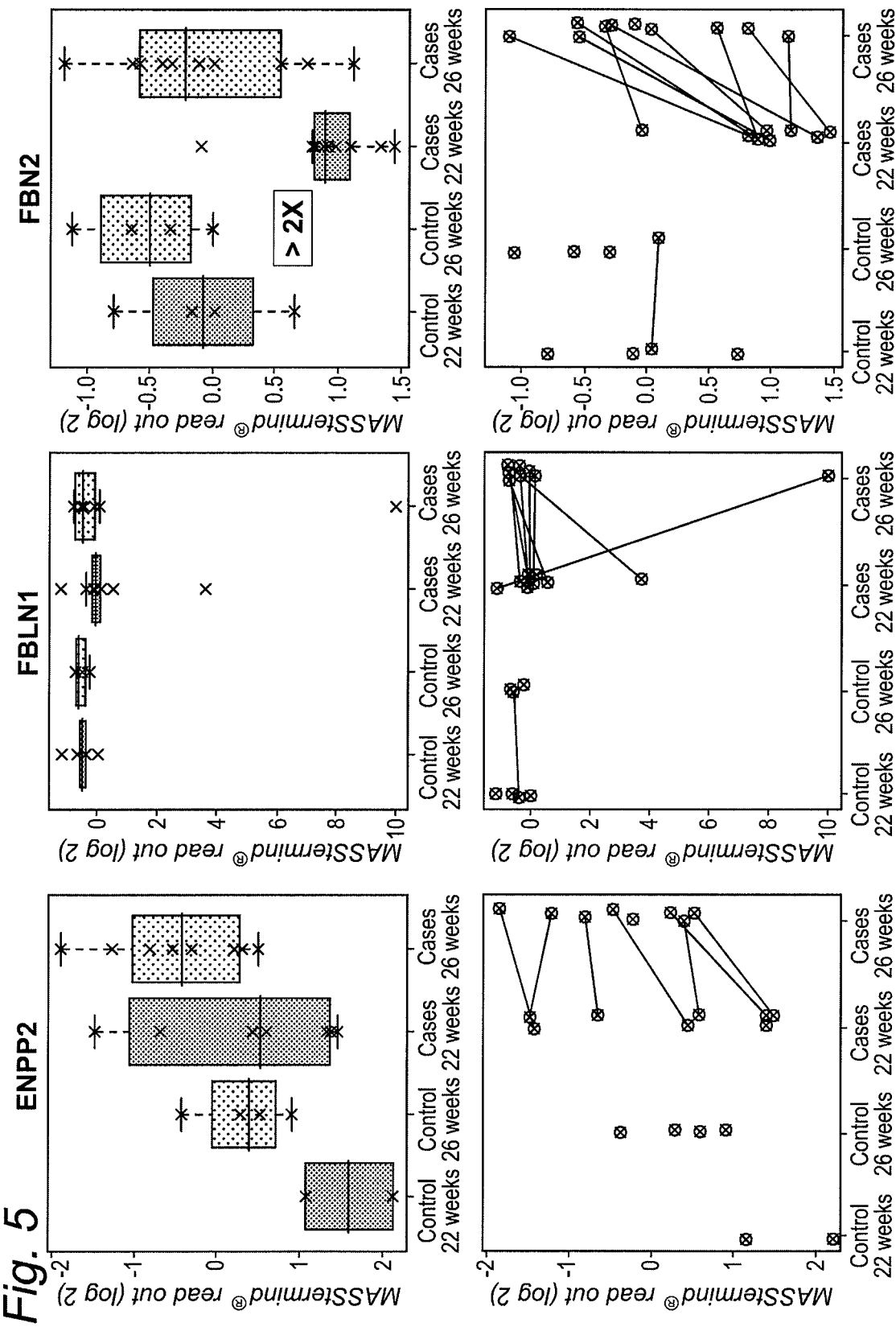
Figure 6:
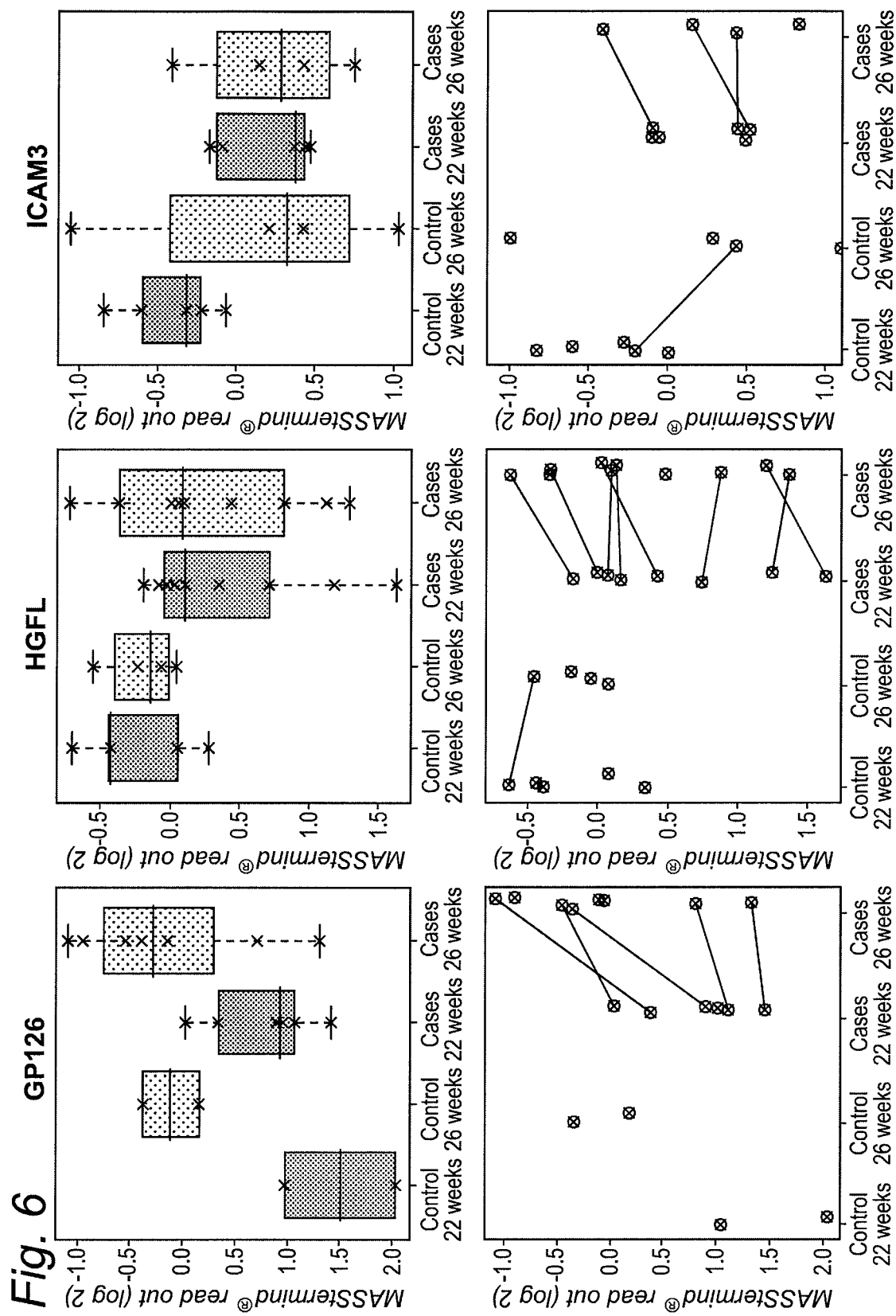
Figure 7:
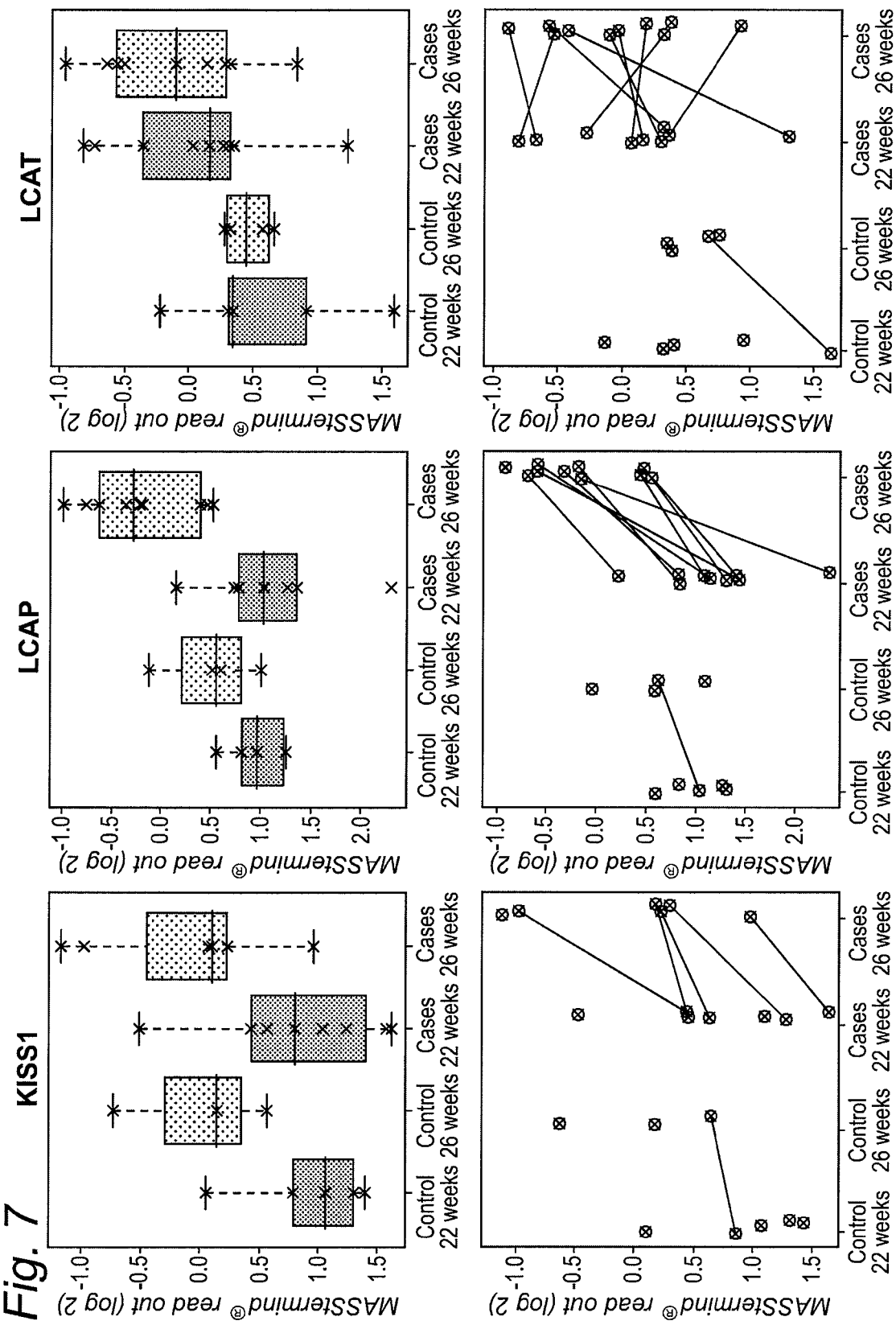
Figure 8:
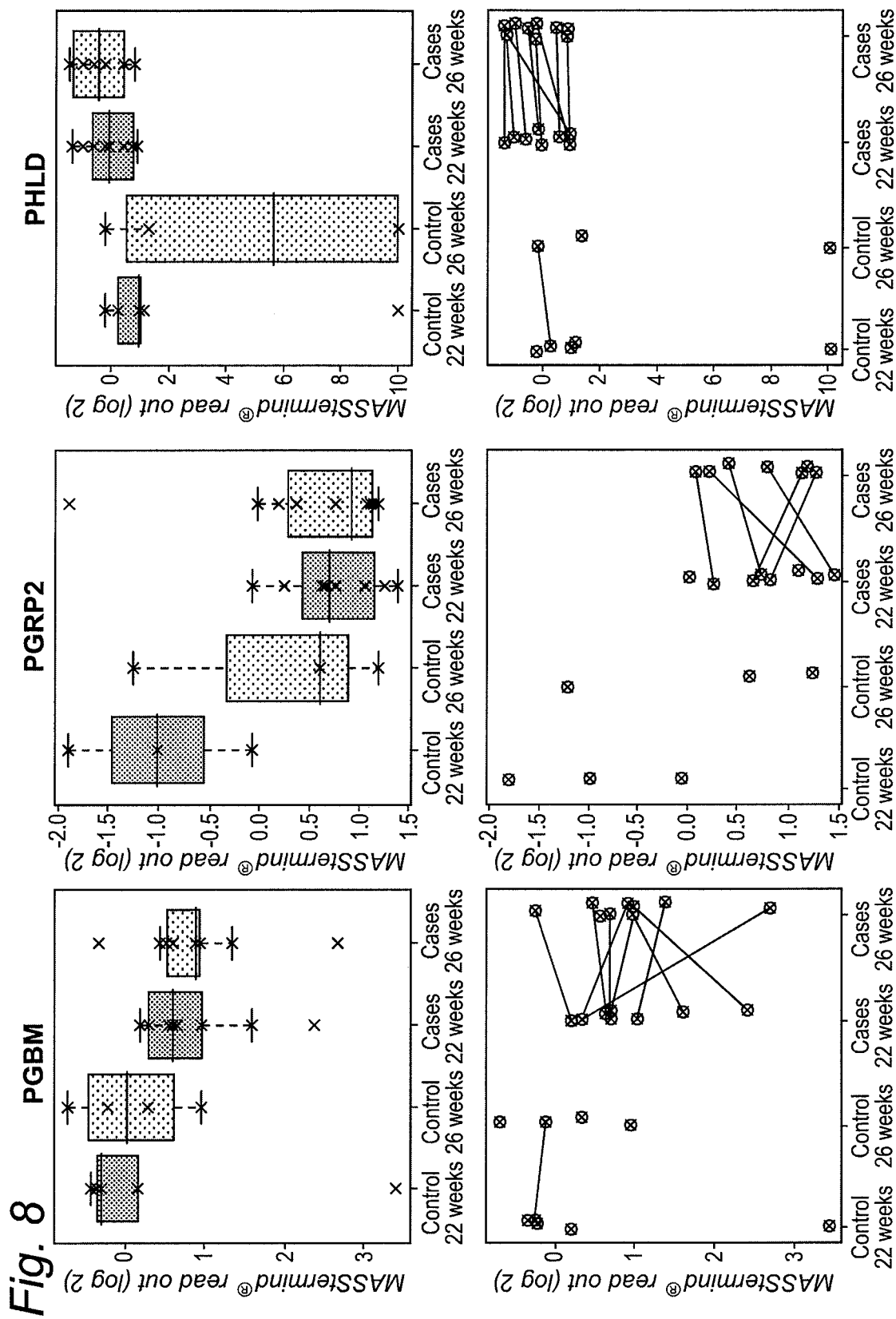
Figure 9:
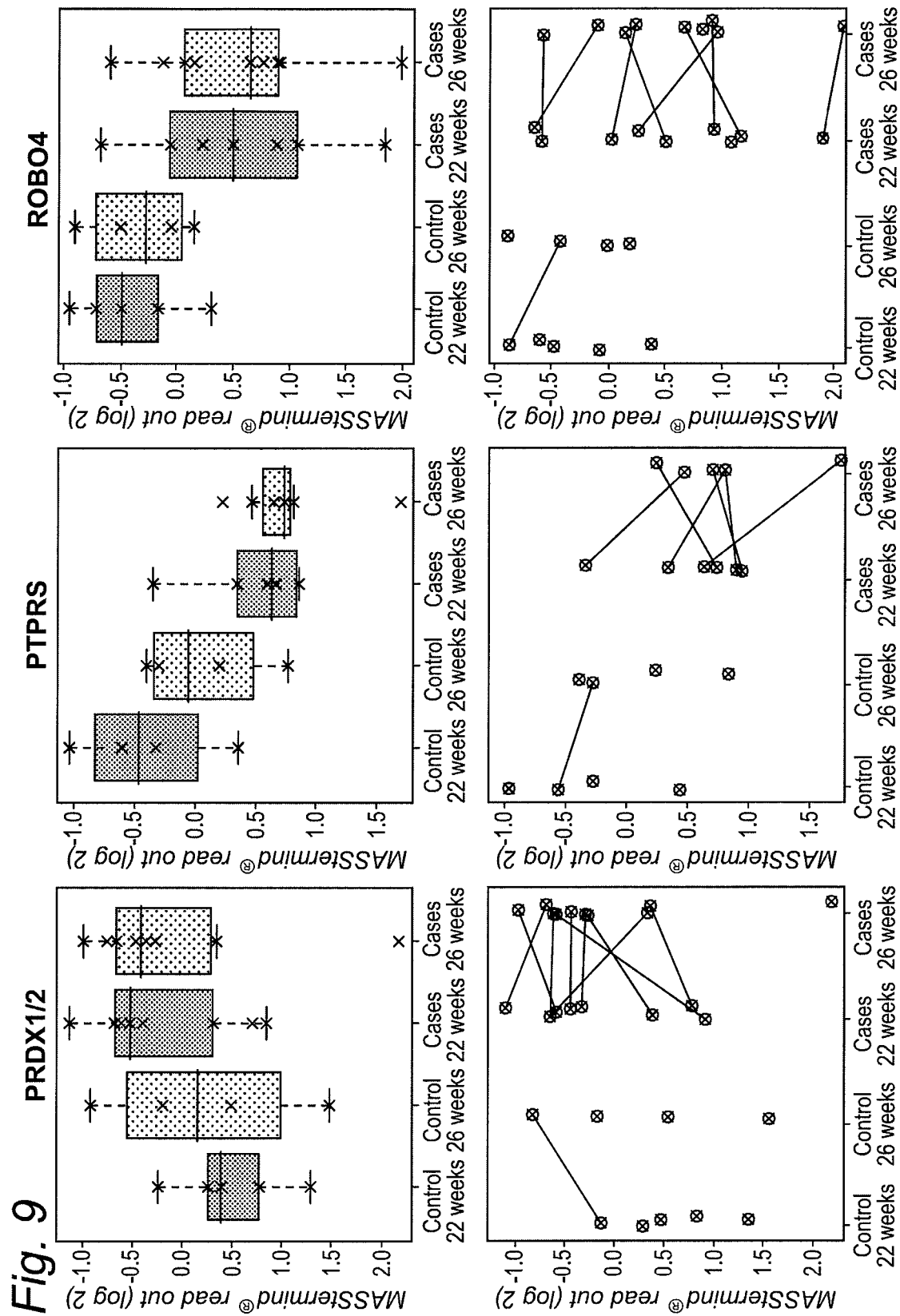
Figure 10:
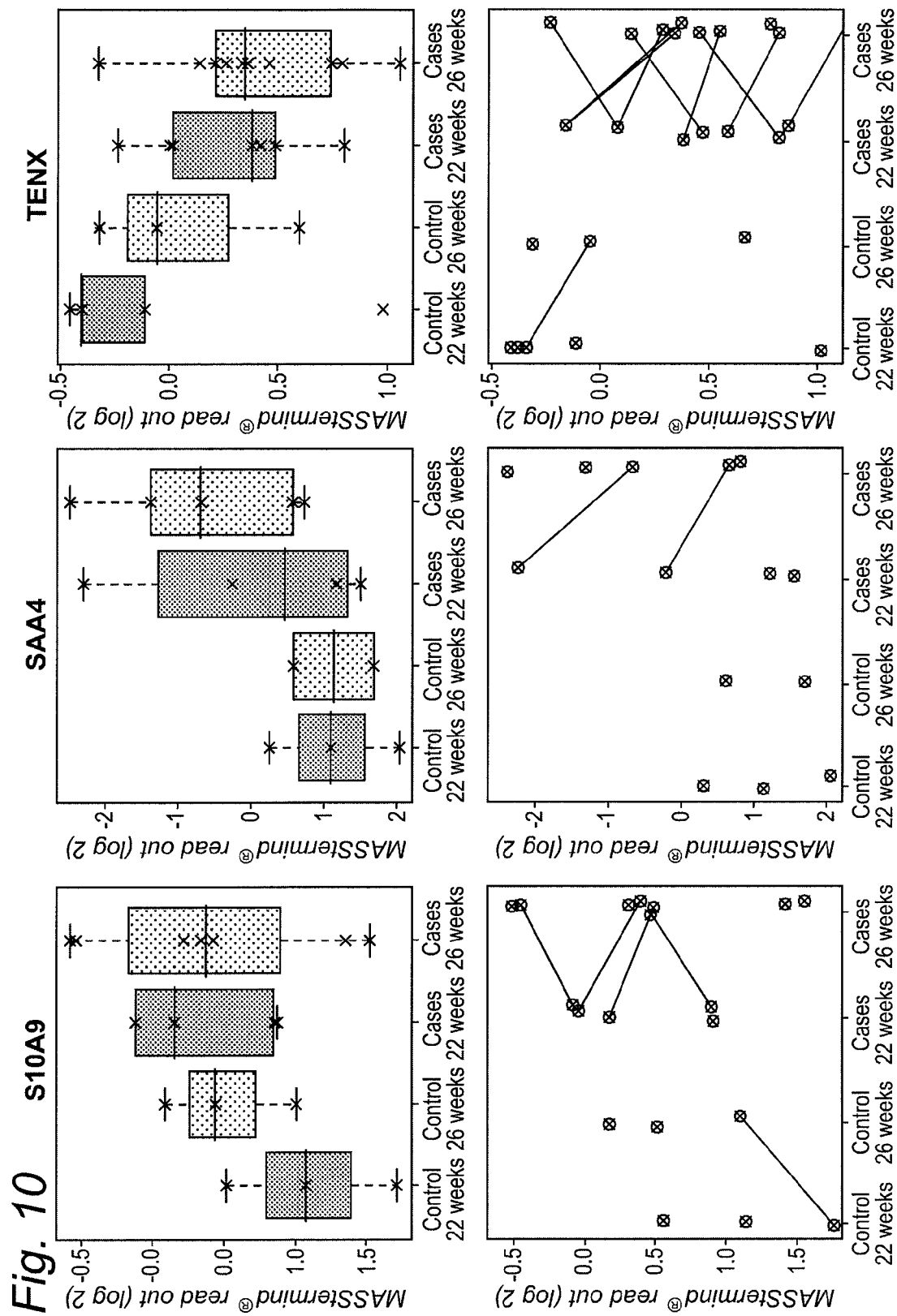
Figure 11:
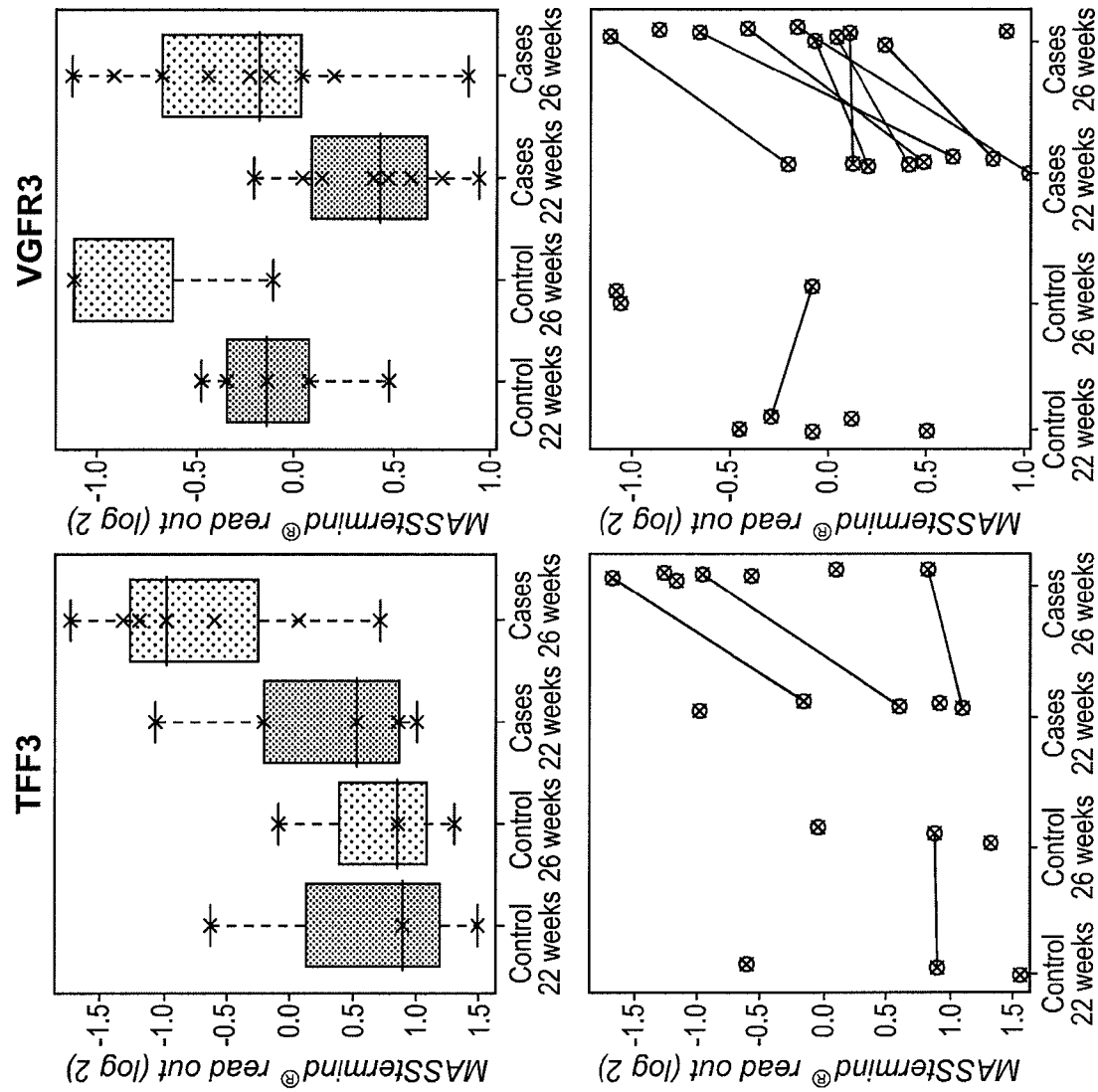
Figure 12:
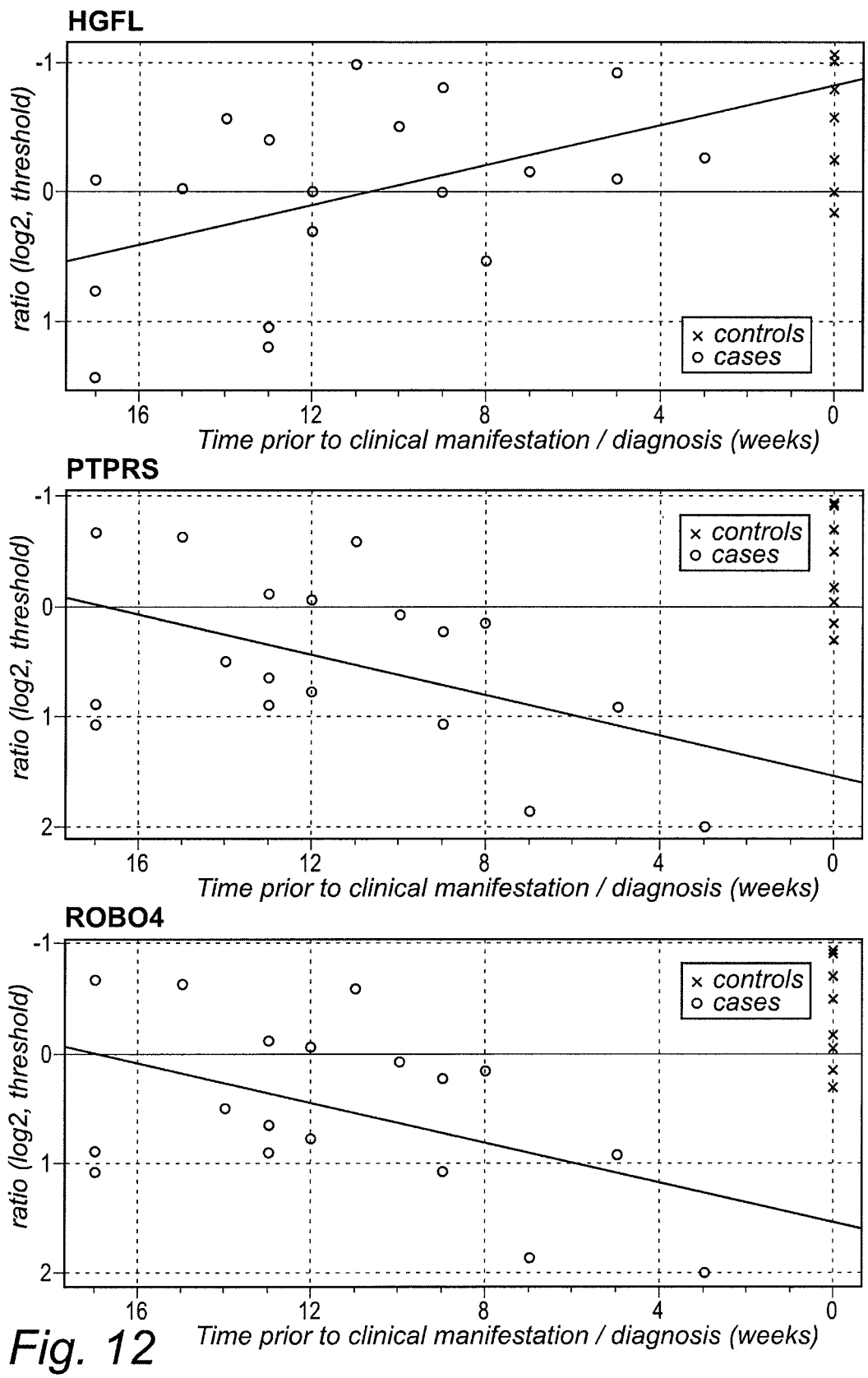
FIGS. 12 and 13 illustrate the correlation between the quantity of the respective markers in cases (Y-axis) and time to onset (manifestation/diagnosis) of PE (X-axis).
Figure 13:
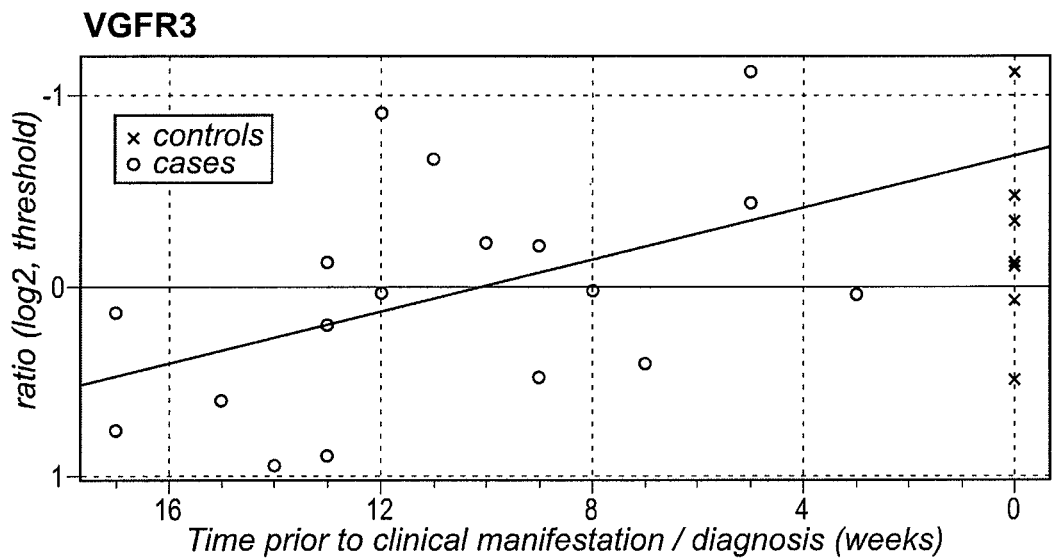

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The term also encompasses "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

The inventors realised any one or more of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 as valuable biomarkers particularly for hypertensive disorders of pregnancy (HDP) such as preferably preeclampsia (PE).

The term "biomarker" is widespread in the art and may broadly denote a biological molecule and/or a detectable portion thereof whose qualitative and/or quantitative evaluation in a subject is predictive or informative (e.g., predictive, diagnostic and/or prognostic) with respect to one or more aspects of the subject's phenotype and/or genotype, such as, for example, with respect to the status of the subject as to a given disease or condition. Preferably, biomarkers as intended herein are peptide-, polypeptide- and/or protein-based. The terms "biomarker" and "marker" may be used interchangeably herein.

Reference herein to "disease(s) and/or condition(s) as taught herein" or a similar reference encompasses any such diseases and conditions as disclosed herein insofar consistent with the context of such a recitation, in particular but without limitation including hypertensive disorders of pregnancy and preferably preeclampsia.

Hypertensive disorders of pregnancy (HDP) include a heterogeneous collection of diseases and conditions associated with hypertension during pregnancy and/or post partum (e.g., up to 12 weeks postpartum).

HDP may be conveniently classified as follows:
I. Hypertension induced by pregnancy
   a. without proteinuria or (generalised) oedema
   b. with proteinuria or (generalised) oedema (i.e., preeclampsia)
     i. mild
     ii. severe
   c. eclampsia
II. Coincidental hypertension (chronic hypertension)
III. Hypertension worsened by pregnancy (pregnancy aggravated hypertension)
   a. superimposed preeclampsia
   b. superimposed eclampsia Recent studies may no longer classify PE as mild or severe, but may instead identify PE groups based on gestation time, preferably: a. early onset (i.e., clinical manifestation <34 weeks of gestation); b. preterm (i.e., clinical manifestation >34 and <37 weeks of gestation); c. term (i.e., clinical manifestation ≥37 weeks of gestation).

HPD may otherwise be categorised as pre-existing or gestational, optionally adding "with preeclampsia" to either category if maternal or foetal symptoms, signs or test results necessitate this.

Non-proteinuric hypertension of pregnancy may be conveniently defined as blood pressure of systolic BP≥140 mmHg and/or a diastolic BP≥90 mmHg measured on two separate occasions over 4 hours apart, e.g., about 4 hours to about 168 hours apart.

When the hypertension was measured before pregnancy or is measured before 20 weeks of gestation, one may commonly denote such as chronic hypertension. When the hypertension is measured in a previously normotensive woman after 20 weeks of gestation, one may denote such as pregnancy-induced hypertension. Typically, pregnancy-induced hypertension will resolve within 12 weeks postpartum. When blood pressure of at least 140/90 mmHg is measured but does not persist for more than 6 hours, one may denote such as transient hypertension.

Proteinuric hypertension of pregnancy may be as defined in the previous paragraph, further accompanied by ≥300 mg of total protein in a 24-hour urine collection.

HDP also encompasses diseases and conditions commonly denoted in the art as gestational hypertension, mild preeclampsia, pregnancy-induced hypertension, specific hypertension of pregnancy, toxaemia of pregnancy, etc.

The terms "gestational age", "age of gestation" and similar are widespread in the art and commonly denote the time as measured in weeks from the 1$^{st}$ day of a female's last menstrual period. A human pregnancy of normal gestation is between about 38 and 42 weeks, preferably about 40 weeks.

"Preeclampsia" (PE or pre-eclampsia) generally denotes a pregnancy-associated disease or condition characterised by hypertension with proteinuria or oedema or both. PE may also be accompanied by glomerular dysfunction, brain oedema, liver oedema, coagulation abnormalities and/or other complications.

PE may be conveniently defined as some combination of the following signs and symptoms:
(1) a systolic blood pressure (BP)≥140 mmHg and/or a diastolic BP≥90 mmHg after 20 weeks gestation (generally measured on two occasions over 4 hours apart, e.g., about 4 to about 168 hours apart),
(2) new onset proteinuria (1+by dipstick on urinanalysis, ≥300 mg of protein in a 24-hour urine collection, or a single random urine sample having a protein/creatinine ratio ≥0.3) after 20 weeks gestation, and
(3) resolution of hypertension and proteinuria by 12 weeks postpartum,
such as in particular a combination of hypertension and proteinuria.

Severe PE may be conveniently defined as:
(1) a systolic BP ≥160 mmHg or diastolic BP≥110 mmHg (generally measured on two occasions over 4 hours apart, e.g., about 4 to about 168 hours apart) or
(2) proteinuria characterised by a measurement of ≥3.5 g in a 24-hour urine collection or two random urine specimens with at least 3+ protein by dipstick.

In PE, hypertension and proteinuria generally occur within seven days of each other. In severe PE, severe hypertension, severe proteinuria or HELLP syndrome (haemolysis, elevated liver enzymes, low platelets) or eclampsia can occur simultaneously or only one symptom at a time.

Occasionally, severe PE can lead to the development of seizures, i.e., to eclampsia. Eclampsia can also include dysfunction or damage to several organs or tissues such as the liver (e.g., hepatocellular damage, periportal necrosis) and the central nervous system (e.g., cerebral oedema and cerebral haemorrhage).

Hence, HDP also encompasses diseases and conditions commonly denoted in the art as PE, including inter alia mild PE, severe PE and PE with further complications, eclampsia and HELLP syndrome.

The terms "predicting" or "prediction", "diagnosing" or "diagnosis" and "prognosticating" or "prognosis" are commonplace and well-understood in medical and clinical practice. It shall be understood that the phrase "a method for the diagnosis, prediction and/or prognosis" a given disease or condition may also be interchanged with phrases such as "a method for diagnosing, predicting and/or prognosticating" of said disease or condition or "a method for making (or determining or establishing) the diagnosis, prediction and/or prognosis" of said disease or condition, or the like.

By means of further explanation and without limitation, "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

The terms "diagnosing" or "diagnosis" generally refer to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition). As used herein, "diagnosis of" the diseases or conditions as taught herein in a subject may particularly mean that the subject has such, hence, is diagnosed as having such. "Diagnosis of no" diseases or conditions as taught herein in a subject may particularly mean that the subject does not have such, hence, is diagnosed as not having such. A subject may be diagnosed as not having such despite displaying one or more conventional symptoms or signs reminiscent of such.

The terms "prognosticating" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The term "subject" or "patient" as used herein typically denotes humans, but may also encompass reference to non-human animals, preferably warm-blooded animals, more preferably viviparous animals, even more preferably mammals, such as, e.g., non-human primates, rodents, canines, felines, equines, ovines, porcines, and the like. Particularly intended are female subjects, more particularly pregnant or postpartum female subjects.

The terms "sample" or "biological sample" as used herein include any biological specimen obtained from a subject. Samples may include, without limitation, whole blood, plasma, serum, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. Preferred samples may include ones comprising any one or more markers as taught herein protein in detectable quantities. In preferred embodiments, the sample may be whole blood or a fractional component thereof such as, e.g., plasma, serum, or a cell pellet. Preferably the sample is readily obtainable by minimally invasive methods, allowing to remove or isolate said sample from the subject. Samples may also include tissue samples and biopsies, tissue homogenates and the like. Preferably, the sample used to detect the levels of any one or more markers as taught herein is blood plasma. The term "plasma" generally denotes the substantially colourless watery fluid of the blood that contains no cells, but in which the blood cells (erythrocytes, leukocytes, thrombocytes, etc.) are normally suspended, containing nutrients, sugars, proteins, minerals, enzymes, etc. Also preferably, said sample is urine.

A molecule or analyte such as a protein, polypeptide or peptide, or a group of two or more molecules or analytes such as two or more proteins, polypeptides or peptides, is "measured" in a sample when the presence or absence and/or quantity of said molecule or analyte or of said group of molecules or analytes is detected or determined in the sample, preferably substantially to the exclusion of other molecules and analytes.

The terms "quantity", "amount" and "level" are synonymous and generally well-understood in the art. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the biomarker. These values or ranges can be obtained from a single patient or from a group of patients.

An absolute quantity of a molecule or analyte in a sample may be advantageously expressed as weight or as molar amount, or more commonly as a concentration, e.g., weight per volume or mol per volume.

A relative quantity of a molecule or analyte in a sample may be advantageously expressed as an increase or decrease or as a fold-increase or fold-decrease relative to said another value, such as relative to a reference value as taught herein. Performing a relative comparison between first and second parameters (e.g., first and second quantities) may but need not require to first determine the absolute values of said first and second parameters. For example, a measurement method can produce quantifiable readouts (such as, e.g., signal intensities) for said first and second parameters, wherein said readouts are a function of the value of said parameters, and wherein said readouts can be directly compared to produce a relative value for the first parameter vs. the second parameter, without the actual need to first convert the readouts to absolute values of the respective parameters.

As used herein, the reference to any one marker (biomarker), nucleic acid, peptide, polypeptide or protein corresponds to the marker, nucleic acid, peptide, polypeptide or protein commonly known under the respective designations in the art. The terms encompass such markers, nucleic acids, proteins and polypeptides of any organism where found, and particularly of animals, preferably warm-blooded animals, more preferably vertebrates, yet more preferably mammals, including humans and non-human mammals, still more preferably of humans. The terms particularly encompass such markers, nucleic acids, proteins and polypeptides with a native sequence, i.e., ones of which the primary sequence is the same as that of the markers, nucleic acids, proteins and polypeptides found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to post-transcriptional or post-translational modifications. Any such variants or isoforms of markers, nucleic acids, proteins and polypeptides are intended herein. Accordingly, all sequences of markers, nucleic acids, proteins and polypeptides found in or derived from nature are considered "native". The terms encompass the markers, nucleic acids, proteins and polypeptides when forming a part of a living organism, organ, tissue or cell, when forming a part of a biological sample, as well as when at least partly isolated from such sources. The terms also encompass proteins and polypeptides when produced by recombinant or synthetic means.

Exemplary human markers, nucleic acids, proteins or polypeptides as taught herein may be as annotated under NCBI Genbank accession numbers given below. A skilled person can also appreciate that in some instances said sequences may be of precursors (e.g., preproteins) of the of markers, nucleic acids, proteins or polypeptides as taught herein and may include parts which are processed away from mature molecules. A skilled person can further appreciate that although only one or more isoforms may be listed below, all isoforms are intended. Unless otherwise specified, the entries below are presented in the form: Name (Code; Genbank accession number for one or more representative amino acid sequences (e.g., isoforms), Genbank sequence version "v."):

Insulin-like growth factor-binding protein complex acid labile chain (ALS; NP_004961, v.1). The sequence annotated under NP_004961 is reproduced below:

```
                                              (SEQ ID NO: 33)
MALRKGGLALALLLLSWVALGPRSLEGADPGTPGEAEGPACPAACVCSYD

DDADELSVFCSSRNLTRLPDGVPGGTQALWLDGNNLSSVPPAAFQNLSSL

GFLNLQGGQLGSLEPQALLGLENLCHLHLERNQLRSLALGTFAHTPALAS
```

-continued

```
LGLSNNRLSRLEDGLFEGLGSLWDLNLGWNSLAVLPDAAFRGLGSLRELV

LAGNRLAYLQPALFSGLAELRELDLSRNALRAIKANVFVQLPRLQKLYLD

RNLIAAVAPGAFLGLKALRWLDLSHNRVAGLLEDTFPGLLGLRVLRLSHN

AIASLRPRTFKDLHFLEELQLGHNRIRQLAERSFEGLGQLEVLTLDHNQL

QEVKAGAFLGLTNVAVMNLSGNCLRNLPEQVFRGLGKLHSLHLEGSCLGR

IRPHTFTGLSGLRRLFLKDNGLVGIEEQSLWGLAELLELDLTSNQLTHLP

HRLFQGLGKLEYLLLSRNRLAELPADALGPLQRAFWLDVSHNRLEALPNS

LLAPLGRLRYLSLRNNSLRTFTPQPPGLERLWLEGNPWDCGCPLKALRDF

ALQNPSAVPRFVQAICEGDDCQPPAYTYNNITCASPPEVVGLDLRDLSEA

HFAPC
```

Disintegrin and metalloproteinase domain-containing protein 12 (ADA12; NP_003465, v. 3; NP_067673, v.2)
Angiogenin (ANGI; NP_001091046, v.1; NP_001136, v.1)
Calpain-1 catalytic subunit (CAN1; NP_005177, v.2)
Macrophage colony-stimulating factor 1 receptor (CSF1R; NP_005202, v.2)
C-reactive protein (CRP; NP_000558, v.2)
Chorionic somatomammotropin hormone (CSH; NP_001308, v.1; NP_066271, v.1; NP_072166, v.1; NP_072167, v.1)
Dystroglycan (DAG1; NP_001159400, v.1; NP_004384, v.3)
Dipeptidase 2 (DPEP2; NP_071750, v.1)
Desmoglein-2 (DSG2; NP_001934, v.2)
Extracellular matrix protein 1 (ECM1; NP_004416, v.2; NP_073155, v.2)
Ectonucleotide pyrophosphatase/phosphodiesterase family member 2 (ENPP2; NP_001035181, v.1; NP_001124335, v.1; NP_006200, v.3)
Fibulin-1 (FBLN1; NP_001987, v.2; NP_006476, v.2; NP_006477, v.2; NP_006478, v.2)
Fibrillin-2 (FBN2; NP_001990, v.2.)
Probable G-protein coupled receptor 126 (GP126; NP_001027566, v.1; NP_001027567, v.1; NP_065188, v.4; NP_940971, v.1)
Hepatocyte growth factor-like protein (HGFL; NP_066278, v.3.)
Intercellular adhesion molecule 3 (ICAM3; NP_002153, v.2)
Metastasis-suppressor KISS-1 (KISS1; NP_002247, v.3)
Leucyl-cystinyl aminopeptidase (LCAP; NP_005566, v.2; NP_787116, v.2)
Phosphatidylcholine-sterol acyltransferase (LCAT; NP_000220, v.1)
Basement membrane-specific heparan sulfate proteoglycan core protein (PGBM; NP_005520, v.4)
N-acetylmuramoyl-L-alanine amidase (PGRP2; NP_443122, v.3)
Phosphatidylinositol-glycan-specific phospholipase D (PHLD; NP_001494, v.2; NP_803436, v.1)
Peroxiredoxin 1 (PRDX1; NP_002565, v.1; NP_859047, v.1; NP_859048, v.1)
Peroxiredoxin 2 (PRDX2; NP_005800, v.3),
Receptor-type tyrosine-protein phosphatase S (PTPRS; NP_002841, v.3; NP_570924, v.2; NP_570925, v.2)
Roundabout homolog 4 (ROBO4; NP_061928, v.4)
Protein S100-A9 (S10A9; NP_002956, v.1)
Serum amyloid A-4 protein (SAA4; NP_006503, v.1)
Tenascin-X (TENX; NP_061978, v.6; NP_115859, v.2)
Trefoil factor 3 (TFF3; Swissprot/Uniprot accession no. Q07654, sequence version 1)
Vascular endothelial growth factor receptor 3 (VGFR3; NP_002011, v.2; NP_891555, v.2)

Exemplary human other markers as taught herein may be as annotated under accession numbers given below. A skilled person can also appreciate that in some instances said sequences may be of precursors (e.g., preproteins) of the markers and may include parts which are processed away from mature molecules. Unless otherwise specified, the entries below are presented in the form: Name (Code; Swissprot/Uniprot accession number for one or more representative amino acid sequences (e.g., isoforms), Swissprot/Uniprot sequence version "v."):

Soluble fms-like tyrosine kinase-1 (sFlt-1, sVEGFR-1; P17948, v. 2, isoform P17948-2)
Endoglin (ENG; Genbank accession no. NP_000109, v.1; NP_001108225, v.1)
Placental growth factor (PLGF; P49763, v.2; Genbank accession no. NP_002623, v.2)
Vascular endothelial growth factor (VEGFA; P15692, v.2; e.g., Genbank accession no. NP_001020537, v.2 (VEGFA isoform a)).

The reference herein to any biomolecule, such as a marker (biomarker), peptide, polypeptide or protein may also encompass fragments thereof. Hence, the reference herein to measuring (or measuring the quantity of) any one marker or biomolecule may encompass measuring the marker or biomolecule, such as, e.g., measuring the mature and/or the processed soluble/secreted form (e.g. plasma circulating form) of the marker or biomolecule and/or measuring one or more fragments thereof.

For example, any marker or biomolecule and/or one or more fragments thereof may be measured collectively, such that the measured quantity corresponds to the sum amounts of the collectively measured species. In another example, any marker or biomolecule and/or one or more fragments thereof may be measured each individually. Preferably, said fragment may be a plasma circulating (i.e., not cell- or membrane-bound) form. Without being bound by any theory, such circulating forms can be derived from full-length markers or biomolecules through natural processing, or can be resulting from known degradation processes occurring in a sample. In certain situations, the circulating form can also be the full-length marker or biomolecule, which is found to be circulating in the plasma. Said "circulating form" can thus be any marker or biomolecule or any processed soluble form thereof or fragments of either one, that is circulating in the sample, i.e. which is not bound to a cell- or membrane fraction of said sample.

Unless otherwise apparent from the context, reference herein to any biomolecule such as a marker, peptide, polypeptide or protein encompasses such from any organism where found, and particularly preferably from animals, preferably warm-blooded animals, more preferably vertebrates, even preferably mammals, including humans and non-human mammals, still more preferably from humans.

Further, unless otherwise apparent from the context, reference herein to any marker, peptide, polypeptide or protein and fragments thereof may generally also encompass modified forms of said marker, peptide, polypeptide or protein and fragments such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

In an embodiment, any marker, peptide, polypeptide or protein and fragments thereof, or other biomarkers as employed herein and fragments thereof, may be human, i.e., their primary sequence may be the same as a corresponding primary sequence of or present in a naturally occurring human markers, peptides, polypeptides or proteins. Hence, the qualifier "human" in this connection relates to the primary sequence of the respective markers, peptides, polypeptides, proteins or fragments, rather than to their origin or source. For example, such markers, peptides, polypeptides, proteins or fragments may be present in or isolated from samples of human subjects or may be obtained by other means (e.g., by recombinant expression, cell-free translation or non-biological peptide synthesis).

The term "fragment" of a protein, polypeptide or peptide generally refers to N-terminally and/or C-terminally deleted or truncated forms of said protein, polypeptide or peptide. The term encompasses fragments arising by any mechanism, such as, without limitation, by alternative translation, exo- and/or endo-proteolysis and/or degradation of said peptide, polypeptide or protein, such as, for example, in vivo or in vitro, such as, for example, by physical, chemical and/or enzymatic proteolysis. Without limitation, a fragment of a protein, polypeptide or peptide may represent at least about 5%, or at least about 10%, e.g., ≥20%, ≥30% or ≥40%, such as ≥50%, e.g., ≥60%, ≥70% or ≥80%, or even ≥90% or ≥95% of the amino acid sequence of said protein, polypeptide or peptide.

For example, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full length protein.

In an embodiment, a fragment may be N-terminally and/or C-terminally truncated by between 1 and about 20 amino acids, such as, e.g., by between 1 and about 15 amino acids, or by between 1 and about 10 amino acids, or by between 1 and about 5 amino acids, compared to the corresponding mature, full-length protein or its soluble or plasma circulating form.

In an embodiment, fragments of a given protein, polypeptide or peptide may be achieved by in vitro proteolysis of said protein, polypeptide or peptide to obtain advantageously detectable peptide(s) from a sample. For example, such proteolysis may be effected by suitable physical, chemical and/or enzymatic agents, e.g., proteinases, preferably endoproteinases, i.e., protease cleaving internally within a protein, polypeptide or peptide chain. A non-limiting list of suitable endoproteinases includes serine proteinases (EC 3.4.21), threonine proteinases (EC 3.4.25), cysteine proteinases (EC 3.4.22), aspartic acid proteinases (EC 3.4.23), metalloproteinases (EC 3.4.24) and glutamic acid proteinases. Exemplary non-limiting endoproteinases include trypsin, chymotrypsin, elastase, *Lysobacter enzymogenes* endoproteinase Lys-C, *Staphylococcus aureus* endoproteinase Glu-C (endopeptidase V8) or *Clostridium histolyticum* endoproteinase Arg-C (clostripain). Further known or yet to be identified enzymes may be used; a skilled person can choose suitable protease(s) on the basis of their cleavage specificity and frequency to achieve desired peptide forms. Preferably, the proteolysis may be effected by endopeptidases of the trypsin type (EC 3.4.21.4), preferably trypsin, such as, without limitation, preparations of trypsin from bovine pancreas, human pancreas, porcine pancreas, recombinant trypsin, Lys-acetylated trypsin, trypsin in solution, trypsin immobilised to a solid support, etc. Trypsin is particularly useful, inter alia due to high specificity and efficiency of cleavage.

The invention also contemplates the use of any trypsin-like protease, i.e., with a similar specificity to that of trypsin. Otherwise, chemical reagents may be used for proteolysis. For example, CNBr can cleave at Met; BNPS-skatole can cleave at Trp. The conditions for treatment, e.g., protein concentration, enzyme or chemical reagent concentration, pH, buffer, temperature, time, can be determined by the skilled person depending on the enzyme or chemical reagent employed.

Also provided is thus an isolated fragment of any one marker, peptide, polypeptide or protein selected from the group consisting of ALS, ADA12, ANGI, CAN1, CSF1R, CRP, CSH, DAG1, DPEP2, DSG2, ECM1, ENPP2, FBLN1, FBN2, GP126, HGFL, ICAM3, KISS1, LCAP, LCAT, PGBM, PGRP2, PHLD, PRDX1, PRDX2, PTPRS, ROBO4, S10A9, SAA4, TENX, TFF3, VGFR3 as defined here above. Such fragments may give useful information about the presence and quantity of said markers, peptides, polypeptides or proteins in biological samples, whereby the detection of said fragments is of interest. Hence, the herein disclosed fragments of said markers, peptides, polypeptides or proteins are useful biomarkers.

Preferred fragments may comprise, consist essentially of or consist of the sequence as set forth in SEQ ID NO: 1 to 32 listed in Table 1, which were used in the examples to provide information on the respective markers.

TABLE 1

| Code | Sequence | SEQ ID | Start* |
|---|---|---|---|
| ALS | ADPGTPGEAEGPACPAACVCSYDD DADELSVFCSSR | 3 | 28 |
| ADA12 | QGKDLEKVKQR | 1 | 230 |
| ANGI | LTSPCKDINTFIHGNKR | 2 | 58 |
| CAN1 | PTELSNPQFIVDGATR | 4 | 88 |
| CSF1R | IPVIEPSVPELVVKPGATVTELR | 5 | 20 |
| CRP | FGQTDMSR | 6 | 17 |
| CSH | VQTVPLSR | 7 | 27 |
| DAG1 | HWPSEPSEAVR | 8 | 30 |
| DPEP2 | QVYQKGLQDVNLR | 9 | 98 |
| DSG2 | AWITAPVALR | 10 | 50 |
| ECM1 | SEGGFTATGQR | 11 | 21 |
| ENG | ETVHCDLQPVGPER | 12 | 26 |
| ENPP2 | SMYDPVFDATFHLR | 13 | 232 |
| FBLN1 | DVLLEACCADGHR | 14 | 30 |
| FBN2 | CNCNSGYEPDASGR | 15 | 793 |
| GP126 | THFGVLMDLPR | 16 | 841 |
| HGFL | SPLNDFQVLR | 17 | 21 |
| ICAM3 | QPAVEEPAEVTATVLASR | 18 | 164 |
| KISS1 | EKVASVGNSR | 19 | 23 |

TABLE 1-continued

| Code | Sequence | SEQ ID | Start* |
|---|---|---|---|
| LCAP | ATNGKLFPWAQIR** | 20 | 155 |
| LCAT | QPQAWKDR | 21 | 218 |
| PGBM | SIVPQGGSHSLR | 22 | 1686 |
| PGRP2 | AGLLRPDYALLGHR | 23 | 510 |
| PHLD | CGLSTHVEIGHR | 24 | 24 |
| PRDX1/2 | QITVNDLPVGR | 25 | 140 |
| PTPRS | PTLSVQQTPEGSLLAR | 26 | 836 |
| ROBO4 | QDSPPQILVHPQDQLFQGPGPAR | 27 | 28 |
| S10A9 | TCKMSQLER | 28 | 2 |
| SAA4 | SFFKEALQGVGDMGR | 29 | 23 |
| TENX | AEGTTGLAPAGQTSEESRP | 30 | 3683 |
| TFF3 | EEYVGLSANQCAVPAKDR | 31 | 22 |
| VGFR3 | QQQDLMPQCR | 32 | 478 |

*Start indicates the position in the respective proteins at which the peptide starts
**True N-terminus of the pregnancy specific form The term "isolated" with reference to a particular component (such as for instance, a protein, polypeptide, peptide or fragment thereof) generally denotes that such component exists in separation from—for example, has been separated from or prepared in separation from—one or more other components of its natural environment. For instance, an isolated human or animal protein, polypeptide, peptide or fragment exists in separation from a human or animal body where it occurs naturally.

The term "isolated" as used herein may preferably also encompass the qualifier "purified". As used herein, the term "purified" with reference to protein(s), polypeptide(s), peptide(s) and/or fragment(s) thereof does not require absolute purity. Instead, it denotes that such protein(s), polypeptide(s), peptide(s) and/or fragment(s) is (are) in a discrete environment in which their abundance (conveniently expressed in terms of mass or weight or concentration) relative to other proteins is greater than in a biological sample. A discrete environment denotes a single medium, such as for example a single solution, gel, precipitate, lyophilisate, etc. Purified peptides, polypeptides or fragments may be obtained by known methods including, for example, laboratory or recombinant synthesis, chromatography, preparative electrophoresis, centrifugation, precipitation, affinity purification, etc.

Purified protein(s), polypeptide(s), peptide(s) and/or fragment(s) may preferably constitute by weight ≥10%, more preferably ≥50%, such as ≥60%, yet more preferably ≥70%, such as ≥80%, and still more preferably ≥90%, such as ≥95%, ≥96%, ≥97%, ≥98%, ≥99% or even 100%, of the protein content of the discrete environment. Protein content may be determined, e.g., by the Lowry method (Lowry et al. 1951. J Biol Chem 193: 265), optionally as described by Hartree 1972 (Anal Biochem 48: 422-427). Also, purity of peptides or polypeptides may be determined by SDS-PAGE under reducing or non-reducing conditions using Coomassie blue or, preferably, silver stain.

Further disclosed are any isolated marker, peptide, polypeptide or protein and fragments thereof as taught herein comprising a detectable label. This facilitates ready detection of such fragments. The term "label" as used throughout this specification refers to any atom, molecule, moiety or biomolecule that can be used to provide a detectable and preferably quantifiable read-out or property, and that can be attached to or made part of an entity of interest, such as a peptide or polypeptide or a specific-binding agent. Labels may be suitably detectable by mass spectrometric, spectroscopic, optical, colourimetric, magnetic, photochemical, biochemical, immunochemical or chemical means. Labels include without limitation dyes; radiolabels such as $^{32}$P, $^{33}$P, $^{35}$S, $^{125}$I, $^{131}$I; electron-dense reagents; enzymes (e.g., horseradish phosphatise or alkaline phosphatise as commonly used in immunoassays); binding moieties such as biotin-streptavidin; haptens such as digoxigenin; luminogenic, phosphorescent or fluorogenic moieties; mass tags; and fluorescent dyes alone or in combination with moieties that can suppress or shift emission spectra by fluorescence resonance energy transfer (FRET).

For example, the label may be a mass-altering label. Preferably, a mass-altering label may involve the presence of a distinct stable isotope in one or more amino acids of the peptide vis-à-vis its corresponding non-labelled peptide. Mass-labelled peptides are particularly useful as positive controls, standards and calibrators in mass spectrometry applications. In particular, peptides including one or more distinct isotopes are chemically alike, separate chromatographically and electrophoretically in the same manner and also ionise and fragment in the same way. However, in a suitable mass analyser such peptides and optionally select fragmentation ions thereof will display distinguishable m/z ratios and can thus be discriminated. Examples of pairs of distinguishable stable isotopes include H and D, $^{12}$C and $^{13}$C, $^{14}$N and $^{15}$N or $^{16}$O and $^{18}$O. Usually, peptides and proteins of biological samples analysed in the present invention may substantially only contain common isotopes having high prevalence in nature, such as for example H, $^{12}$C, $^{14}$N and $^{16}$O. In such case, the mass-labelled peptide may be labelled with one or more uncommon isotopes having low prevalence in nature, such as for instance D, $^{13}$C, $^{15}$N and/or $^{18}$O. It is also conceivable that in cases where the peptides or proteins of a biological sample would include one or more uncommon isotopes, the mass-labelled peptide may comprise the respective common isotope(s).

Isotopically-labelled synthetic peptides may be obtained inter alia by synthesising or recombinantly producing such peptides using one or more isotopically-labelled amino acid substrates, or by chemically or enzymatically modifying unlabelled peptides to introduce thereto one or more distinct isotopes. By means of example and not limitation, D-labelled peptides may be synthesised or recombinantly produced in the presence of commercially available deuterated L-methionine $CH_3$—S—$CD_2CD_2$—$CH(NH_2)$—COOH or deuterated arginine $H_2NC(=NH)$—NH—$(CD_2)_3$—$CD(NH_2)$—COOH. It shall be appreciated that any amino acid of which deuterated or $^{15}$N- or $^{13}$C-containing forms exist may be considered for synthesis or recombinant production of labelled peptides. In another non-limiting example, a peptide may be treated with trypsin in $H_2^{16}O$ or $H_2^{18}O$, leading to incorporation of two oxygens ($^{16}$O or $^{18}$O, respectively) at the COOH-termini of said peptide (e.g., US 2006/105415).

Accordingly, also contemplated is the use of any (isolated) marker, peptide, polypeptide or protein and fragments thereof as taught herein, optionally comprising a detectable label, as (positive) controls, standards or calibrators in qualitative or quantitative detection assays (measurement methods) of said marker, peptide, polypeptide or protein and fragments thereof, and particularly in such methods for the diagnosis, prediction, prognosis and/or monitoring the diseases or conditions as taught herein in subjects. The markers, proteins, polypeptides or peptides may be supplied in any form, inter alia as precipitate, vacuum-dried, lyophilisate, in solution as liquid or frozen, or covalently or non-covalently immobilised on solid phase, such as for example, on solid chromatographic matrix or on glass or plastic or other suitable surfaces (e.g., as a part of peptide arrays and microarrays). The peptides may be readily prepared, for example, isolated from natural sources, or prepared recombinantly or synthetically.

Further disclosed are binding agents capable of specifically binding to any one or more (isolated) markers, peptides, polypeptides or proteins and fragments thereof as taught herein. Also disclosed are binding agents capable of specifically binding to only one of (isolated) markers, peptides, polypeptides or proteins and fragments thereof as taught herein. Binding agents as intended throughout this specification may include inter alia an antibody, aptamer, photoaptamer, protein, peptide, peptidomimetic or a small molecule.

The term "specifically bind" as used throughout this specification means that an agent (denoted herein also as "specific-binding agent") binds to one or more desired molecules or analytes, such as to one or more proteins, polypeptides or peptides of interest or fragments thereof substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to protein(s) polypeptide(s), peptide(s) and/or fragment(s) thereof of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater, than its affinity for a non-target molecule.

Preferably, the agent may bind to its intended target(s) with affinity constant ($K_A$) of such binding $K_A \geq 1 \times 10^6$ M$^{-1}$, more preferably $K_A \geq 1 \times 10^7$ M$^{-1}$, yet more preferably $K_A \geq 1 \times 10^8$ M$^{-1}$, even more preferably $K_A \geq 1 \times 10^9$ M$^{-1}$, and still more preferably $K_A \geq 1 \times 10^{10}$ M$^{-1}$ or $K_A \geq 1 \times 10^{11}$ M$^{-1}$, wherein $K_A = [SBA\_T]/[SBA][T]$, SBA denotes the specific-binding agent, T denotes the intended target. Determination of $K_A$ can be carried out by methods known in the art, such as for example, using equilibrium dialysis and Scatchard plot analysis.

Specific binding agents as used throughout this specification may include inter alia an antibody, aptamer, photoaptamer, protein, peptide, peptidomimetic or a small molecule.

As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments; diabodies; linear antibodies; single-chain antibody molecules; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromaderius*), llama (e.g., *Lama paccos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

The term "aptamer" refers to single-stranded or double-stranded oligo-DNA, oligo-RNA or oligo-DNA/RNA or any analogue thereof, that can specifically bind to a target molecule such as a peptide. Advantageously, aptamers can display fairly high specificity and affinity (e.g., $K_A$ in the order $1 \times 10^9$ $M^{-1}$) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Harwell 1995 (Trends Biotechnol 13: 132-134).

The term "small molecule" refers to compounds, preferably organic compounds, with a size comparable to those organic molecules generally used in pharmaceuticals. The term excludes biological macromolecules (e.g., proteins, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

Hence, also disclosed are methods for immunising animals, e.g., non-human animals such as laboratory or farm, animals using (i.e., using as the immunising antigen) any one or more (isolated) markers, peptides, polypeptides or proteins and fragments thereof as taught herein, optionally attached to a presenting carrier. Immunisation and preparation of antibody reagents from immune sera is well-known per se and described in documents referred to elsewhere in this specification. The animals to be immunised may include any animal species, preferably warm-blooded species, more preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel, llama or horse. The term "presenting carrier" or "carrier" generally denotes an immunogenic molecule which, when bound to a second molecule, augments immune responses to the latter, usually through the provision of additional T cell epitopes. The presenting carrier may be a (poly)peptidic structure or a non-peptidic structure, such as inter alia glycans, polyethylene glycols, peptide mimetics, synthetic polymers, etc. Exemplary non-limiting carriers include human Hepatitis B virus core protein, multiple C3d domains, tetanus toxin fragment C or yeast Ty particles.

Immune sera obtained or obtainable by immunisation as taught herein may be particularly useful for generating antibody reagents that specifically bind to any one or more (isolated) markers, peptides, polypeptides or proteins and fragments thereof disclosed herein.

Any existing, available or conventional separation, detection and quantification methods can be used herein to measure the presence or absence (e.g., readout being present vs. absent; or detectable amount vs. undetectable amount) and/or quantity (e.g., readout being an absolute or relative quantity, such as, for example, absolute or relative concentration) of markers, peptides, polypeptides, proteins and/or fragments thereof and optionally of the one or more other biomarkers or fragments thereof in samples (any molecules or analytes of interest to be so-measured in samples, including any one or more markers, peptides, polypeptides, proteins and fragments thereof as taught herein, may be herein below referred to collectively as biomarkers).

For example, such methods may include immunoassay methods, mass spectrometry analysis methods, or chromatography methods, or combinations thereof.

The term "immunoassay" generally refers to methods known as such for detecting one or more molecules or analytes of interest in a sample, wherein specificity of an immunoassay for the molecule(s) or analyte(s) of interest is conferred by specific binding between a specific-binding agent, commonly an antibody, and the molecule(s) or analyte(s) of interest. Immunoassay technologies include without limitation direct ELISA (enzyme-linked immunosorbent assay), indirect ELISA, sandwich ELISA, competitive ELISA, multiplex ELISA, radioimmunoassay (RIA), ELISPOT technologies, and other similar techniques known in the art. Principles of these immunoassay methods are known in the art, for example John R. Crowther, "The ELISA Guidebook", 1st ed., Humana Press 2000, ISBN 0896037282.

By means of further explanation and not limitation, direct ELISA employs a labelled primary antibody to bind to and thereby quantify target antigen in a sample immobilised on a solid support such as a microwell plate. Indirect ELISA uses a non-labelled primary antibody which binds to the target antigen and a secondary labelled antibody that recognises and allows to quantify the antigen-bound primary antibody. In sandwich ELISA the target antigen is captured from a sample using an immobilised 'capture' antibody which binds to one antigenic site within the antigen, and subsequent to removal of non-bound analytes the so-captured antigen is detected using a 'detection' antibody which binds to another antigenic site within said antigen, where the detection antibody may be directly labelled or indirectly detectable as above. Competitive ELISA uses a labelled 'competitor' that may either be the primary antibody or the target antigen. In an example, non-labelled immobilised primary antibody is incubated with a sample, this reaction is allowed to reach equilibrium, and then labelled target antigen is added. The latter will bind to the primary antibody wherever its binding sites are not yet occupied by non-labelled target antigen from the sample. Thus, the detected amount of bound labelled antigen inversely correlates with the amount of non-labelled antigen in the sample. Multiplex ELISA allows simultaneous detection of two or more analytes within a single compartment (e.g., microplate well) usually at a plurality of array addresses (see, for example, Nielsen & Geierstanger 2004. J Immunol Methods 290: 107-20 and Ling et al. 2007. Expert Rev Mol Diagn 7: 87-98 for further guidance). As appreciated, labelling in ELISA technologies is usually by enzyme (such as, e.g., horseradish peroxidase) conjugation and the end-point is typically colourimetric, chemiluminescent or fluorescent, magnetic, piezo electric, pyroelectric and other.

Radioimmunoassay (RIA) is a competition-based technique and involves mixing known quantities of radioactively-labelled (e.g., $^{125}$I- or $^{131}$I-labelled) target antigen with antibody to said antigen, then adding non-labelled or 'cold' antigen from a sample and measuring the amount of labelled antigen displaced (see, e.g., "An Introduction to Radioimmunoassay and Related Techniques", by Chard T, ed., Elsevier Science 1995, ISBN 0444821198 for guidance).

Generally, any mass spectrometric (MS) techniques that can obtain precise information on the mass of peptides, and preferably also on fragmentation and/or (partial) amino acid sequence of selected peptides (e.g., in tandem mass spectrometry, MS/MS; or in post source decay, TOF MS), are useful herein. Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)$^n$ (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)$^n$; atmospheric pressure photoionization mass spectrometry (APPI-MS); APPI-MS/MS; and APPI-(MS)$^n$. Peptide ion fragmentation in tandem MS (MS/MS) arrangements may be achieved using manners established in the art, such as, e.g., collision induced dissociation (CID). Detection and quantification of biomarkers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods described herein below.

Chromatography can also be used for measuring biomarkers. As used herein, the term "chromatography" encompasses methods for separating chemical substances, referred to as such and vastly available in the art. In a preferred approach, chromatography refers to a process in which a mixture of chemical substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography is also widely applicable for the separation of chemical compounds of biological origin, such as, e.g., amino acids, proteins, fragments of proteins or peptides, etc.

Chromatography as used herein may be preferably columnar (i.e., wherein the stationary phase is deposited or packed in a column), preferably liquid chromatography, and yet more preferably HPLC. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immuno-affinity, immobilised metal affinity chromatography, and the like.

Chromatography, including single-, two- or more-dimensional chromatography, may be used as a peptide fractionation method in conjunction with a further peptide analysis method, such as for example, with a downstream mass spectrometry analysis as described elsewhere in this specification.

Further peptide or polypeptide separation, identification or quantification methods may be used, optionally in conjunction with any of the above described analysis methods, for measuring biomarkers in the present disclosure. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

The various aspects and embodiments taught herein may further rely on comparing the quantity of any one or more biomarkers measured in samples with reference values of the quantity of said one or more biomarkers, wherein said reference values represent known predictions, diagnoses and/or prognoses of diseases or conditions as taught herein.

For example, distinct reference values may represent the prediction of a risk (e.g., an abnormally elevated risk) of having a given disease or condition as taught herein vs. the prediction of no or normal risk of having said disease or condition. In another example, distinct reference values may represent predictions of differing degrees of risk of having such disease or condition.

In a further example, distinct reference values can represent the diagnosis of a given disease or condition as taught herein vs. the diagnosis of no such disease or condition (such as, e.g., the diagnosis of healthy, or recovered from said disease or condition, etc.). In another example, distinct reference values may represent the diagnosis of such disease or condition of varying severity.

In yet another example, distinct reference values may represent a good prognosis for a given disease or condition as taught herein vs. a poor prognosis for said disease or condition. In a further example, distinct reference values may represent varyingly favourable or unfavourable prognoses for such disease or condition.

Such comparison may generally include any means to determine the presence or absence of at least one difference and optionally of the size of such different between values or profiles being compared. A comparison may include a visual inspection, an arithmetical or statistical comparison of measurements. Such statistical comparisons include, but are not limited to, applying a rule. If the values or biomarker profiles comprise at least one standard, the comparison may to determine a difference in said values or biomarker profiles may also include measurements of these standards, such that measurements of the biomarker are correlated to measurements of the internal standards.

Reference values for the quantity of any one or more biomarkers may be established according to known procedures previously employed for other biomarkers.

For example, a reference value of the quantity of any one or more biomarkers for a particular diagnosis, prediction and/or prognosis of given disease or condition as taught herein may be established by determining the quantity of said one or more biomarkers in sample(s) from one individual or from a population of individuals characterised by said particular diagnosis, prediction and/or prognosis of said disease or condition (i.e., for whom said diagnosis, prediction and/or prognosis of the disease or condition holds true). Such population may comprise without limitation ≥2, ≥10, ≥100, or even several hundreds or more individuals.

Hence, by means of an illustrative example, reference values of the quantity of any one or more biomarkers for the diagnoses of a given disease or condition as taught herein vs. no such disease or condition may be established by determining the quantity of said one or more biomarkers in sample(s) from one individual or from a population of individuals diagnosed (e.g., based on other adequately conclusive means, such as, for example, clinical signs and symptoms, imaging, ECG, etc.) as, respectively, having or not having said disease or condition.

In an embodiment, reference value(s) as intended herein may convey absolute quantities of any one or more biomarkers. In another embodiment, the quantity of any one or more biomarkers in a sample from a tested subject may be determined directly relative to the reference value (e.g., in terms of increase or decrease, or fold-increase or fold-decrease). Advantageously, this may allow to compare the quantity of any one or more biomarkers in the sample from the subject with the reference value (in other words to measure the relative quantity of any one or more biomarkers in the sample from the subject vis-à-vis the reference value) without the need to first determine the respective absolute quantities of said one or more biomarkers.

The expression level or presence of a biomarker in a sample of a patient may sometimes fluctuate, i.e. increase or decrease significantly without change (appearance of, worsening or improving of) symptoms. In such an event, the marker change precedes the change in symptoms and becomes a more sensitive measure than symptom change. Therapeutic intervention can be initiated earlier and be more effective than waiting for deteriorating symptoms. Early intervention at a more benign status may be carried out safely at home, which is a major improvement from treating seriously deteriorated patients in the emergency room.

Measuring the level of any one or more biomarkers of the same patient at different time points can in such a case thus enable the continuous monitoring of the status of the patient and can lead to prediction of worsening or improvement of the patient's condition with regard to a given disease or condition as taught herein. A home or clinical test kit or device as indicated herein can be used for this continuous monitoring. One or more reference values or ranges of levels of any one or more biomarkers linked to a certain disease state for such a test can e.g. be determined beforehand or during the monitoring process over a certain period of time in said subject. Alternatively, these reference values or ranges can be established through data sets of several patients with highly similar disease phenotypes, e.g. from healthy subjects or subjects not having the disease or condition of interest. A sudden deviation of the levels of any one or more biomarkers from said reference value or range can predict the worsening of the condition of the patient (e.g. at home or in the clinic) before the (often severe) symptoms actually can be felt or observed.

Also disclosed is thus a method or algorithm for determining a significant change in the level of any one or more biomarkers as taught herein in a certain patient, which is indicative for change (worsening or improving) in clinical status. In addition, the invention allows establishing the diagnosis that the subject is recovering or has recovered from a given disease or condition as taught herein.

In an embodiment the present methods may include a step of establishing such reference value(s). In an embodiment, the present kits and devices may include means for establishing a reference value of the quantity of any one or more biomarkers as taught herein for a particular diagnosis, prediction and/or prognosis of a given disease or condition as taught herein. Such means may for example comprise one or more samples (e.g., separate or pooled samples) from one or more individuals characterised by said particular diagnosis, prediction and/or prognosis of said disease or condition.

The various aspects and embodiments taught herein may further entail finding a deviation or no deviation between the quantity of any one or more biomarkers measured in a sample from a subject and a given reference value.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD, or ±1×SE or ±2×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off.

Such threshold or cut-off may be selected as generally known in the art to provide for a chosen sensitivity and/or specificity of the diagnosis, prediction and/or prognosis methods, e.g., sensitivity and/or specificity of at least 50%, or at least 60%, or at least 70%, or at least 80%, or at least 85%, or at least 90%, or at least 95%.

For example, in an embodiment, an elevated quantity of any one or more biomarkers in the sample from the subject—preferably at least about 1.1-fold elevated, or at least about 1.2-fold elevated, more preferably at least about 1.3-fold elevated, even more preferably at least about 1.4-fold elevated, yet more preferably at least about 1.5-fold elevated, such as between about 1.1-fold and 3-fold elevated or between about 1.5-fold and 2-fold elevated—compared to a reference value representing the prediction or diagnosis of no given disease or condition as taught herein or representing a good prognosis for said disease or condition indicates that the subject has or is at risk of having said disease or condition or indicates a poor prognosis for the disease or condition in the subject, or indicates that the subject does not have or is not at risk of having said disease or condition or indicates a good prognosis for the disease or condition in the subject.

When a deviation is found between the quantity of any one or more biomarkers in a sample from a subject and a reference value representing a certain diagnosis, prediction and/or prognosis of a given disease or condition as taught herein, said deviation is indicative of or may be attributed to the conclusion that the diagnosis, prediction and/or prognosis of said disease or condition in said subject is different from that represented by the reference value.

When no deviation is found between the quantity of any one or more biomarkers in a sample from a subject and a reference value representing a certain diagnosis, prediction and/or prognosis of a given disease or condition as taught herein, the absence of such deviation is indicative of or may be attributed to the conclusion that the diagnosis, prediction and/or prognosis of said disease or condition in said subject is substantially the same as that represented by the reference value.

The above considerations apply analogously to biomarker profiles.

When two or more different biomarkers are determined in a subject, their respective presence, absence and/or quantity may be together represented as a biomarker profile, the values for each measured biomarker making a part of said profile. As used herein, the term "profile" includes any set of data that represents the distinctive features or characteristics associated with a condition of interest, such as with a particular diagnosis, prediction and/or prognosis of a given disease or condition as taught herein. The term generally encompasses inter alia nucleic acid profiles, such as for example genotypic profiles (sets of genotypic data that represents the genotype of one or more genes associated with a condition of interest), gene copy number profiles (sets of gene copy number data that represents the amplification or deletion of one or more genes associated with a condition of interest), gene expression profiles (sets of gene expression data that represents the mRNA levels of one or more genes associated with a condition of interest), DNA methylation profiles (sets of methylation data that represents the DNA methylation levels of one or more genes associated with a condition of interest), as well as protein, polypeptide or peptide profiles, such as for example protein expression profiles (sets of protein expression data that represents the levels of one or more proteins associated with a condition of interest), protein activation profiles (sets of data that represents the activation or inactivation of one or more proteins associated with a condition of interest), protein modification profiles (sets of data that represents the modification of one or more proteins associated with a condition of interest), protein cleavage profiles (sets of data that represent the proteolytic cleavage of one or more proteins associated with a condition of interest), as well as any combinations thereof.

Biomarker profiles may be created in a number of ways and may be the combination of measurable biomarkers or aspects of biomarkers using methods such as ratios, or other more complex association methods or algorithms (e.g., rule-based methods). A biomarker profile comprises at least two measurements, where the measurements can correspond to the same or different biomarkers. A biomarker profile may also comprise at least three, four, five, 10, 20, 30 or more measurements. In one embodiment, a biomarker profile comprises hundreds, or even thousands, of measurements.

Hence, for example, distinct reference profiles may represent the prediction of a risk (e.g., an abnormally elevated risk) of having a given disease or condition vs. the prediction of no or normal risk of having said disease or condition. In another example, distinct reference profiles may represent predictions of differing degrees of risk of having said disease or condition.

In a further example, distinct reference profiles can represent the diagnosis of a given disease or condition as taught herein vs. the diagnosis no such disease or condition (such as, e.g., the diagnosis of healthy, recovered from said disease or condition, etc.). In another example, distinct reference profiles may represent the diagnosis of said disease or condition of varying severity.

In a yet another example, distinct reference profiles may represent a good prognosis for a disease or condition as taught herein vs. a poor prognosis for said disease or condition. In a further example, distinct reference profiles may represent varyingly favourable or unfavourable prognoses for such disease or condition.

Reference profiles used herein may be established according to known procedures previously employed for other biomarkers.

For example, a reference profile of the quantity of any two or more biomarkers for a particular diagnosis, prediction and/or prognosis of a given disease or condition as taught herein may be established by determining the profile in sample(s) from one individual or from a population of individuals characterised by said particular diagnosis, prediction and/or prognosis of said disease or condition (i.e., for whom said diagnosis, prediction and/or prognosis of said disease or condition holds true). Such population may comprise without limitation ≥2, ≥10, ≥100, or even several hundreds or more individuals.

Hence, by means of an illustrative example, reference profiles for the diagnoses of a given disease or condition as taught herein vs. no such disease or condition may be established by determining the biomarker profiles in sample(s) from one individual or from a population of individuals diagnosed as, respectively, having or not having said disease or condition.

In an embodiment the present methods may include a step of establishing such reference profile(s). In an embodiment, the present kits and devices may include means for establishing a reference profile for a particular diagnosis, prediction and/or prognosis of a given disease or condition as taught herein. Such means may for example comprise one or more samples (e.g., separate or pooled samples) from one or more individuals characterised by said particular diagnosis, prediction and/or prognosis of said disease or condition.

Further, art-known multi-parameter analyses may be employed mutatis mutandis to determine deviations between groups of values and profiles generated there from (e.g., between sample and reference biomarker profiles).

When a deviation is found between the sample profile and a reference profile representing a certain diagnosis, prediction and/or prognosis of a given disease or condition as taught herein, said deviation is indicative of or may be attributed to the conclusion that the diagnosis, prediction and/or prognosis of said disease or condition in said subject is different from that represented by the reference profile.

When no deviation is found between the sample profile and a reference profile representing a certain diagnosis, prediction and/or prognosis of a given disease or condition as taught herein, the absence of such deviation is indicative of or may be attributed to the conclusion that the diagnosis, prediction and/or prognosis of said disease or condition in said subject is substantially the same as that represented by the reference profile.

The present invention further provides kits or devices for the diagnosis, prediction, prognosis and/or monitoring of any one disease or condition as taught herein comprising means for detecting the level of any one or more biomarkers in a sample of the patient. In a more preferred embodiment, such a kit or kits of the invention can be used in clinical settings or at home. The kit according to the invention can be used for diagnosing said disease or condition, for monitoring the effectiveness of treatment of a subject suffering from said disease or condition with an agent, or for preventive screening of subjects for the occurrence of said disease or condition in said subject.

In a clinical setting, the kit or device can be in the form of a bed-side device or in an emergency team setting, e.g. as part of the equipment of an ambulance or other moving emergency vehicle or team equipment or as part of a first-aid kit. The diagnostic kit or device can assist a medical practitioner, a first aid helper, or nurse to decide whether the patient under observation is developing a disease or condition as taught herein, after which appropriate action or treatment can be performed.

A home-test kit gives the patient a readout which he can communicate to a medicinal practitioner, a first aid helper or to the emergency department of a hospital, after which appropriate action can be taken. Such a home-test device is of particular interest for people having either a history of, or are at risk of suffering from any one disease or condition as taught herein.

Typical kits or devices according to the invention comprise the following elements:
a) a means for obtaining a sample from the subject
b) a means or device for measuring the amount of any one or more markers as taught herein in said sample and visualizing whether the amount of the one or more markers in said sample is below or above a certain threshold level or value, indicating whether the subject is suffering from a given disease or condition as taught herein or not.

In any of the embodiments of the invention, the kits or devices can additionally comprise
c) means for communicating directly with a medical practitioner, an emergency department of the hospital or a first aid post, indicating that a person is suffering from said disease or condition or not.

The term "threshold level or value" or "reference value" is used interchangeably as a synonym and is as defined herein. It can also be a range of base-line (e.g. "dry weight") values determined in an individual patient or in a group of patients with highly similar disease conditions.

Any of kits as defined herein can be used as a bed-side device for use by the subject himself or by a clinical practitioner.

In said kit of the invention, the means for obtaining a sample from the subject (a) can be any means for obtaining a sample from the subject known in the art. Examples for obtaining e.g. a blood sample are known in the art and could be any kind of finger or skin prick or lancet based device, which basically pierces the skin and results in a drop of blood being released from the skin. When a urine sample is used, the means for obtaining a sample from the subject can be in the form of an absorbent strip such as the ones used in home pregnancy tests known in the art. In analogy, a saliva sample could be obtained using a mount swab known in the art. Example of blood sampling devices or other sampling devices are for example given in U.S. Pat. Nos. 4,802,493, 4,966,159, 5,099,857, 6,095,988, 5,944,671, 4,553,541, 3,760,809, 5,395,388, 5,212,879, 5,630,828, 5,133,730, 4,653,513, 5,368,047, 5,569,287, 4,360,016, 5,413,006 and U.S. Pat. Applic. 2002/111565, 2004/0096959, 2005/143713, 2005/137525, 2003/0153900, 2003/0088191, WO9955232, WO2005/049107, WO2004/060163, WO02/056751, WO02/100254, WO2003/022330, WO2004/066822, WO97/46157, WO2004/039429, or EP0364621, EP0078724, EP1212138, EP0081975, or EP0292928. The way of providing or obtaining the sample is by no means limiting.

In said kit of the invention, the means or device for measuring the amount of any one or more markers in said sample (b) can be any means or device that can specifically detect the amount of said one or more markers in the sample. Examples are systems comprising specific binding molecules for said one or more markers attached to a solid phase, e.g. lateral flow strips or dipstick devices and the like well known in the art. One non-limiting example to perform a biochemical assay is to use a test-strip and labelled antibodies which combination does not require any washing of the membrane. The test strip is well known, for example, in the field of pregnancy testing kits where an anti-hCG antibody is present on the support, and is carried complexed with hCG by the flow of urine onto an immobilised second antibody that permits visualisation. Other non-limiting examples of such home test devices, systems or kits can be found for example in the following U.S. Pat. Nos. 6,107,045, 6,974,706, 5,108,889, 6,027,944, 6,482,156, 6,511,814, 5,824,268, 5,726,010, 6,001,658 or U.S. patent applications: 2008/0090305 or 2003/0109067.

In a preferred embodiment, the invention provides a lateral flow device or dipstick. Such dipstick comprises a test strip allowing migration of a sample by capillary flow from one end of the strip where the sample is applied to the other end of such strip where presence of an analyte in said sample is measured.

In another embodiment, the invention provides a device comprising a reagent strip. Such reagent strip comprises one or more test pads which when wetted with the sample, provide a colour change in the presence of an analyte and/or indicate the concentration of the protein in said sample.

In one preferred embodiment of the kit of the invention, the means or device (1) for measuring the amount of protein in a sample (b) is a solid support (7) having a proximal (2) and distal (3) end, comprising:
a sample application zone (4) in the vicinity of the proximal end, a reaction zone (5) distal to the sample application zone (4), and a detection zone (6) distal to the reaction zone (5), whereby said support has a capillary property that directs a flow of fluid sample applied in the application zone in a direction from the proximal end to the distal end, optionally, the means or device also comprises a source of fluid, e.g. in a container, dropper pipette or vial, enabling viscous samples to flow easier through the strip.

The reaction zone (5) comprises one or more bands (10) of binding molecule(s) for any one or more markers conjugated to a detection agent (e.g. colloidal gold) which binding molecule conjugate is disposed on the solid support such that it can migrate with the capillary flow of fluid i.e. it is not immobilised. The detection zone (6) comprises one or more capture bands (11) comprising a population of binding molecules for any one or more markers immobilised on the solid support.

When a sample is applied to the sample application zone (4), it migrates towards the reaction zone (5) by capillary flow. Any one or more markers present in the sample reacts with the labelled binding molecule conjugate, and the complex so formed is carried by capillary flow to the detection zone (6). The detection zone (6), having binding molecules permanently immobilised thereon, captures and immobilises any complex, resulting in a localised concentration of conjugate that can be visualised.

The two zones (5 and 6) as described herein (one zone with the non-fixed conjugates and one zone with the fixed capture antibodies) generally do not overlap. They may be adjacently arranged with an absence or presence of an intervening gap of solid support devoid of band. A band may be disposed on a solid support by any means, for example, absorbed, adsorbed, coated, covalently attached or dried, depending on whether the reagent is required to be mobilised or not.

In order to obtain a semi-quantitative test strip in which only a signal is formed once the level of any one or more markers in the sample is higher than a certain predetermined threshold level or value, the reaction zone (5) comprising the non-fixed conjugated binding molecules, could also comprise a predetermined amount of fixed capture antibodies for said one or more markers. This enables to capture away a certain amount of said one or more markers present in the sample, corresponding to the threshold level or value as predetermined. The remaining amount of said any one or more markers (if any) bound by the conjugated or labelled binding molecules can then be allowed to migrate to the detection zone (6). In this case, the reaction zone (6) will only receive labelled binding molecule-biomarker complexes and subsequently only produce a signal if the level of said one or more biomarkers in the sample is higher than the predetermined threshold level or value.

Another possibility to determine whether the amount of any one or more markers in the sample is below or above a certain threshold level or value, is to use a primary capturing antibody capturing all said one or more markers protein present in the sample, in combination with a labelled secondary antibody, developing a certain signal or colour when bound to the solid phase. The intensity of the colour or signal can then either be compared to a reference colour or signal chart indicating that when the intensity of the signal is above a certain threshold signal, the test is positive. Alternatively, the amount or intensity of the colour or signal can be measured with an electronic device comprising e.g. a light absorbance sensor or light emission meter, resulting in a numerical value of signal intensity or colour absorbance formed, which can then be displayed to the subject in the form of a negative result if said numerical value is below the threshold value or a positive result if said numerical value is above the threshold value. This embodiment is of particular relevance in monitoring the level of said one or more markers in a patient over a period of time.

The reference value or range can e.g. be determined using the home device in a period wherein the subject is free of a given disease or condition, giving the patient an indication of his base-line level of any one or more markers. Regularly using the home test device will thus enable the subject to notice a sudden change in levels of said one or more markers as compared to the base-line level, which can enable him to contact a medical practitioner.

Alternatively, the reference value can be determined in the subject suffering from a given disease or condition as taught herein, which then indicates his personal "risk level" for any one or more markers, i.e. the level of said one or more markers which indicates he is or will soon be exposed to said disease or condition. This risk level is interesting for monitoring the disease progression or for evaluating the effect of the treatment.

Furthermore, the reference value or level can be established through combined measurement results in subjects with highly similar disease states or phenotypes (e.g. all having no disease or condition as taught herein or having said disease or condition).

Non-limiting examples of such semi-quantitative tests known in the art, the principle of which could be used for the home test device according to the present invention are the HIV/AIDS test or Prostate Cancer tests sold by Sanitoets. The home prostate test is a rapid test intended as an initial semi-quantitative test to detect PSA blood levels higher than 4 ng/ml in whole blood. The typical home self-test kit comprises the following components: a test device to which the blood sample is to be administered and which results in a signal when the protein level is above a certain threshold level, an amount of diluent e.g. in dropper pipette to help the transfer of the analytes (i.e. the protein of interest) from the sample application zone to the signal detection zone, optionally an empty pipette for blood specimen collection, a finger pricking device, optionally a sterile swab to clean the area of pricking and instructions of use of the kit.

Similar tests are also known for e.g. breast cancer detection and CRP-protein level detection in view of cardiac risk home tests. The latter test encompasses the sending of the test result to a laboratory, where the result is interpreted by a technical or medical expert. Such telephone or internet based diagnosis of the patient's condition is of course possible and advisable with most of the kits, since interpretation of the test result is often more important than conducting the test. When using an electronic device as mentioned above which gives a numerical value of the level of protein present in the sample, this value can of course easily be communicated through telephone, mobile telephone, satellite phone, E-mail, internet or other communication means, warning a hospital, a medicinal practitioner or a first aid team that a person is, or may be at risk of, suffering from the disease or condition as taught herein. A non-limiting example of such a system is disclosed in U.S. Pat. No. 6,482,156.

Reference is made in the description below to the drawings which exemplify particular embodiments of the invention; they are not at all intended to be limiting. The skilled person may adapt the device and substituent components and features according to the common practices of the person skilled in the art.

Figure 14:
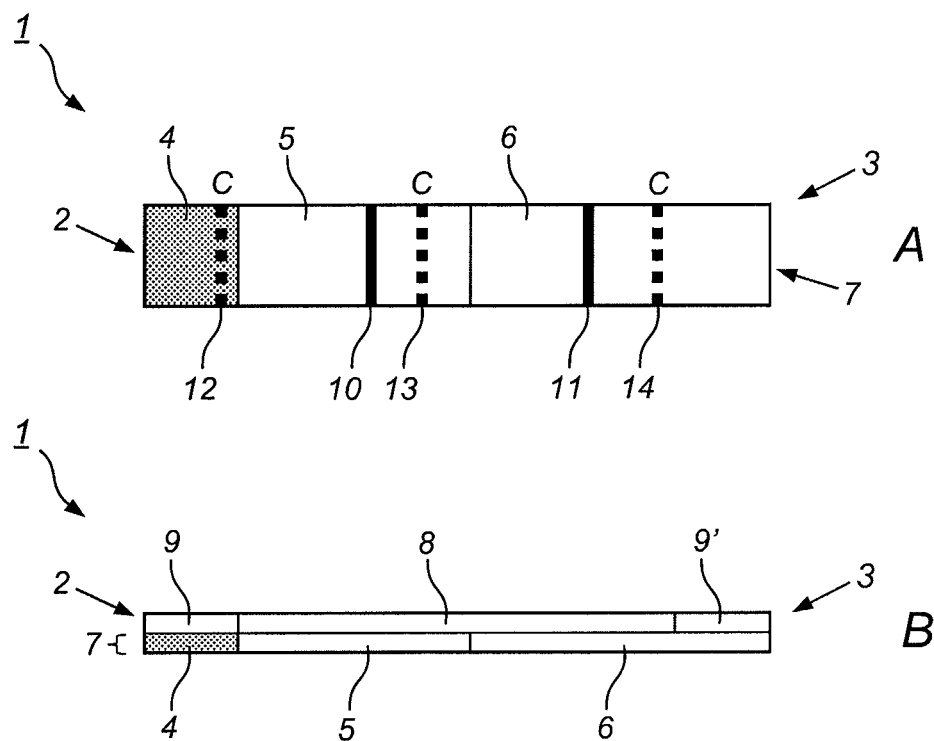
FIG. 14: Plan (A) and side view (B) of a test strip according to the invention.

FIGS. 14A and B shows a preferred embodiment of a test strip of the invention. The strip (1) includes a proximal end (2) and a distal end (3). A sample application zone (4) is provided in the proximal end (2), a reaction zone (5) is adjacent thereto and a detection zone (6) is in the vicinity of the distal end (3). A sample may be deposited onto the solid support (7) at the application zone (4) to transfer by capillary action to the detection zone (6). A protective layer (8) that covers either or both the surfaces of the solid support (7), except for a region of the sample application zone (4) may be provided. Such protective layer protects the sample and chemical constituency of the strip from contamination and evaporation. One or more absorbent pads (9) in capillary contact with the sample application zone (4) of the solid support (7) may absorb and release sample as necessary; such pad (9) is typically placed on the surface of the solid support (7) that is the same or opposing the sample application zone (4). In FIG. 14B, the absorbent pad (9) is part of the sample application zone (4). One or more other absorbent pads (9') in capillary may be placed in contact with the detection zone (6) of the solid support (7), distal to any capture bands (11), (14). These pads (9') may absorb fluid that has passed through the solid support; such pad (9') is typically placed on the surface of the solid support (7) that is the same or opposing the sample application zone (4). The solid support (7) may made from any suitable material that has a capillary action property, and may have the same properties as described above. It should also be capable of supporting a substance (e.g. non-immobilised binding molecule for any one or more markers), which, when hydrated, can migrate across the solid support by a capillary action fluid flow.

The solid support (7) may also comprise a band of binding molecule conjugate for any one or more markers (10), located in the reaction zone (5), at a position distal to the sample application zone (4). Any said one or more markers in the sample is carried by capillary action towards this band (10), where it reacts with the permanently immobilised binding molecule conjugate.

The binding molecule conjugate may be associated with or attached to a detection agent to facilitate detection. Examples of lab detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. More commonly, the detection agent is a particle. Examples of particles useful in the practice of the invention include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles are colloidal gold particles. Colloidal gold may be made by any conventional means, such as the methods outlined in G. Frens, 1973 Nature Physical Science, 241:20 (1973). Alternative methods may be described in U.S. Pat. Nos. 5,578,577, 5,141, 850; 4,775,636; 4,853,335; 4,859,612; 5,079,172; 5,202, 267; 5,514,602; 5,616,467; 5,681,775.

The solid support (7) further comprises one or more capture bands (11) in the detection zone (6). A capture band comprises a population of binding molecule for any one or more markers permanently immobilised thereon. The marker: binding molecule conjugate complex formed in the reaction zone (5) migrates towards the detection zone (6) where said band (11) captures migrating complex, and concentrates it, allowing it to be visualised either by eye, or using a machine reader. The binding molecule present in the reaction zone (5) and in the detection zone (6) may reaction to the same part of said one or more markers or may react to different parts of said one or more markers.

One or more controls bands (12) may be present on the solid support (7). For example, a non-immobilised peptide (12) might be present in the sample application zone (4), which peptide does not cross-react with any of bands of binding molecule for any one or more markers (13) or (14). As the sample is applied, it migrates towards the reaction zone (5), where an anti-peptide antibody conjugate is disposed (13), and where a complex peptide-antibody complex is formed. Said complex migrates towards the detection zone (6), where a capture band (14) of anti-peptide antibody is immobilised on the solid support, and which concentrates said complex enabling visualisation. The control capture band (14) is located separately from the capture band for any one or more markers (11), therefore, a positive reaction can be seen distinct from the detection reaction if the assay is working correctly.

A particular advantage of a control according to the invention is that they are internal controls—that is, the control against which the measurement of any one or more markers results may be compared is present on the individual solid support. Therefore, the controls according to the invention may be used to correct for variability in the solid support, for example. Such correction would be impractical with external controls that are based, for example, on a statistical sampling of supports. Additionally, lot-to-lot, and run-to-run, variations between different supports may be minimized by use of control binding agents and control agents according to the invention. Furthermore, the effects of non-specific binding may be reduced. All of these corrections would be difficult to accomplish using external, off-support, controls.

During the assay, any one or more markers from the sample and the binding molecule conjugate combine and concentrate on the solid support (7). This combination results in a concentration of compounds that may can be visualised above the background colour of the solid support (7). The compounds may be formed from a combination of above-mentioned compounds, including antibodies, detection agents, and other particles associated with the reaction and detection zones. Based on the particular assay being performed, the reaction and detection zones may be selectively implemented to achieve an appropriate dynamic range which may be linear or non-linear.

A solid support (7) for performing the assay may be housed within the cartridge (20) as shown, for example, in FIG. 15. The cartridge is preferably watertight, except for one or more openings. The solid support (7) may be exposed through an opening (21) in the cartridge to provide an application zone (4) in proximal end (2), and another opening (22) to enable reading of detection zone (6) close to the distal end (3). Cartridge (20) may include a sensor code (23) for communicating with a reading device.

The presence and/or concentration of any one or more markers in a sample can be measured by surface plasmon resonance (SPR) using a chip having binding molecule for said one or more markers immobilized thereon, fluorescence resonance energy transfer (FRET), bioluminescence resonance energy transfer (BRET), fluorescence quenching, fluorescence polarization measurement or other means known in the art. Any of the binding assays described can be used to determine the presence and/or concentration of any one or more markers in a sample. To do so, binding molecule for any one or more markers is reacted with a sample, and the concentration of said one or more markers is measured as appropriate for the binding assay being used. To validate and calibrate an assay, control reactions using different concentrations of standard one or more markers and/or binding molecule for said one or more markers can be performed. Where solid phase assays are employed, after incubation, a washing step is performed to remove unbound markers. Bound marker is measured as appropriate for the given label (e.g., scintillation counting, fluorescence, antibody-dye etc.). If a qualitative result is desired, controls and different concentrations may not be necessary. Of course, the roles of said one or more markers and binding molecule may be switched; the skilled person may adapt the method so binding molecule is applied to sample, at various concentrations of sample.

A binding molecule as intended herein is any substance that binds specifically to any one or more markers. Examples of a binding molecule useful according to the present invention, includes, but is not limited to an antibody, a polypeptide, a peptide, a lipid, a carbohydrate, a nucleic acid, peptide-nucleic acid, small molecule, small organic molecule, or other drug candidate. A binding molecule can be natural or synthetic compound, including, for example, synthetic small molecule, compound contained in extracts of animal, plant, bacterial or fungal cells, as well as conditioned medium from such cells. Alternatively, binding molecule can be an engineered protein having binding sites for said one or more markers. According to an aspect of the invention, a binding molecule binds specifically to said one or more markers with an affinity better than $10^{-6}$ M. A suitable binding molecule can be determined from its binding with a standard sample of said one or more markers. Methods for determining the binding between binding molecule and said any one or more markers are known in the art. As used herein, the term antibody includes, but is not limited to, polyclonal antibodies, monoclonal antibodies, humanised or chimeric antibodies, engineered antibodies, and biologically functional antibody fragments (e.g. scFv, nanobodies, Fv, etc) sufficient for binding of the antibody fragment to the protein. Such antibody may be commercially available antibody against said one or more markers, such as, for example, a mouse, rat, human or humanised monoclonal antibody.

The binding molecule may labelled with a tag that permits detection with another agent (e.g. with a probe binding partner). Such tags can be, for example, biotin, streptavidin, his-tag, myc tag, maltose, maltose binding protein or any other kind of tag known in the art that has a binding partner. Example of associations which can be utilised in the probe: binding partner arrangement may be any, and includes, for example biotin:streptavidin, his-tag:metal ion (e.g. $Ni^{2+}$), maltose:maltose binding protein.

Further disclosed is a simple and accurate colourimetric reagent strip and method for measuring presence of any one or more markers in a sample. More in particular, the present invention also relates to a device comprising a reagent strip. The present reagent strip comprises a solid support which is provided with at least one test pad for measuring the presence of any one or more markers in a sample. Said test pad preferably comprises a carrier matrix incorporating a reagent composition capable of interacting with said one or more markers to produce a measurable response, preferably a visually or instrumentally measurable response. The reagent strip may be manufactured in any size and shape, but in general the reagent strip is longer than wide. The solid support may be composed of any suitable material and is preferably made of firm or stiff material such as cellulose acetate, polyethylene terephthalate, polypropylene, polycarbonate or polystyrene. In general, the carrier matrix is an absorbent material that allows the urine sample to move, in response to capillary forces, through the carrier matrix to contact the reagent composition and produce a detectable or measurable colour transition. The carrier matrix can be any substance capable of incorporating the chemical reagents required to perform the assay of interest, as long as the carrier matrix is substantially inert with respect to the chemical reagents, and is porous or absorbent relative to the soluble components of the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulose material, like cellulosic beads, and especially fibercontaining papers such as filter paper or chromatographic paper; synthetic or modified naturally-occurring polymers, such as crosslinked gelatin, cellulose acetate, polyvinyl chloride, polyacrylamide, cellulose, polyvinyl alcohol, polysulfones, polyesters, polyacrylates, polyurethanes, crosslinked dextran, agarose, and other such crosslinked and noncrosslinked water-insoluble hydrophilic polymers. Hydrophobic and nonabsorptive substances are not suitable for use as the carrier matrix of the present invention. The carrier matrix can be of different chemical compositions or a mixture of chemical compositions. The matrix also can vary in regards to smoothness and roughness combined with hardness and softness. However, in every instance, the carrier matrix comprises a hydrophilic or absorptive material. The carrier matrix is most advantageously constructed from bibulous filter paper or nonbibulous polymeric films. A preferred carrier matrix is a hydrophilic, bibulous matrix, including cellulosic materials, such as paper, and preferably filter paper or a nonbibulous matrix, including polymeric films, such as a polyurethane or a crosslinked gelatin. A reagent composition which produces a colourimetric change when reacted with any one or more markers in a sample can be homogeneously incorporated into the carrier matrix, and the carrier matrix then holds the reagent composition homogeneously throughout the carrier matrix while maintaining carrier matrix penetrability by the predetermined component of the test sample. Examples of suitable reagent compositions may include for instance a binding molecule for said one or more markers in case of an antibody-based technique, or pH buffer in case of enzymatic detection. The reagent composition is preferably dried and stabilized onto a test pad adhered to at least one end of a solid support. The test pad onto which the reagent composition is absorbed and dried, is preferably made of a membrane material that shows minimal background colour. Preferably, the test pad may be constructed of acid or base washed materials in order to minimize background colour. In another embodiment the reagent composition which is dried onto the reagent strip further comprises wetting agents to reduce brittleness of the test pad. Non-limiting examples of preferred wetting agents include TritonX-100, Bioterg, glycerol, Tween, and the like. The reagent composition can be applied to the reagent strip by any method known in the art. For example, the carrier matrix from which the test pads are made may be dipped into a solution of the reagent composition and dried according to techniques known in the art. A reagent strip according to the invention may be provided with multiple test pads to assay for more than one analyte in a urine sample.

A possible embodiment of a reagent strip 101 according to the invention is depicted diagrammatically in FIG. 16 A-B. The strip 101 includes a proximal end 102 and a distal end 103. Various test pads 109, 109', 109" on which the reagent compositions are provided at the proximal end 102 on a solid support 107 of the reagent strip. The strip must be designed in such a way that it can be wetted with a sufficiently large amount of sample, optionally diluted by a physiological fluid improving the capillary flow of a viscous sample such as blood or saliva and the like.

A reagent strip as defined herein is used as follows. Briefly, one or more test pad areas of the reagent strip of the invention is dipped into a sample or a small amount of sample is applied to the reagent strip onto the test pad area(s). A colour development which can be analyzed visually or by reflectometry occurs on the reagent strip within a short time, usually within 0.5 to 10 minutes. The change in colour of the reagent area on the test pad upon reacting with any one or more markers is preferably directly proportional to the concentration of said one or more markers in the patient sample. The colour intensity that develops on the test pad may be determined visually or by a reflectance-based reader, for example. Colour development at the test pad area(s) is compared to a reference colour or colours to determine an estimate of the amount of said one or more markers present in the sample The colour intensity that develops on the test pad is compared to at least one, and preferably at least two standard colour shades that correspond to a range of concentration of said one or more markers determined by application of a correction factor.

The reagent strip may further comprises a fluorescent or infrared dye, applied either to the support strip or incorporated into a test pad, which ensures proper alignment of the reagent strip in an apparatus having a detection system for the detectable or measurable response.

In another embodiment, the invention also relates to a test pad for measuring the presence of any one or more markers in a sample. Preferably said test pad comprises a carrier matrix incorporating a reagent composition capable of interacting with said one or more markers to produce a measurable response, preferably a visually or instrumentally measurable response. In another preferred embodiment the invention provides a test pad according as define herein for use in on a reagent strip, preferably on a reagent strip as defined herein.

The specific-binding agents, peptides, polypeptides, proteins, biomarkers etc. in the present kits may be in various forms, e.g., lyophilised, free in solution or immobilised on a solid phase. They may be, e.g., provided in a multi-well plate or as an array or microarray, or they may be packaged separately and/or individually. The may be suitably labelled as taught herein. Said kits may be particularly suitable for performing the assay methods of the invention, such as, e.g., immunoassays, ELISA assays, mass spectrometry assays, and the like.

The term "modulate" generally denotes a qualitative or quantitative alteration, change or variation specifically encompassing both increase (e.g., activation) or decrease (e.g., inhibition), of that which is being modulated. The term encompasses any extent of such modulation.

For example, where modulation effects a determinable or measurable variable, then modulation may encompass an increase in the value of said variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of said variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation.

Preferably, modulation of the activity and/or level of intended target(s) (e.g., any one or more markers, nucleic acids, peptides, polypeptides or proteins as taught herein) may be specific or selective, i.e., the activity and/or level of intended target(s) may be modulated without substantially altering the activity and/or level of random, unrelated (unintended, undesired) targets.

Reference to the "activity" of a target may generally encompass any one or more aspects of the biological activity of the target, such as without limitation any one or more aspects of its biochemical activity, enzymatic activity, signalling activity and/or structural activity, e.g., within a cell, tissue, organ or an organism.

In the context of therapeutic or prophylactic targeting of a target, the reference to the "level" of a target may preferably encompass the quantity and/or the availability (e.g., availability for performing its biological activity) of the target, e.g., within a cell, tissue, organ or an organism.

For example, the level of a target may be modulated by modulating the target's expression and/or modulating the expressed target. Modulation of the target's expression may be achieved or observed, e.g., at the level of heterogeneous nuclear RNA (hnRNA), precursor mRNA (pre-mRNA), mRNA or cDNA encoding the target. By means of example and not limitation, decreasing the expression of a target may be achieved by methods known in the art, such as, e.g., by transfecting (e.g., by electroporation, lipofection, etc.) or transducing (e.g., using a viral vector) a cell, tissue, organ or organism with an antisense agent, such as, e.g., antisense DNA or RNA oligonucleotide, a construct encoding the antisense agent, or an RNA interference agent, such as siRNA or shRNA, or a ribozyme or vectors encoding such, etc. By means of example and not limitation, increasing the expression of a target may be achieved by methods known in the art, such as, e.g., by transfecting (e.g., by electroporation, lipofection, etc.) or transducing (e.g., using a viral vector) a cell, tissue, organ or organism with a recombinant nucleic acid which encodes said target under the control of regulatory sequences effecting suitable expression level in said cell, tissue, organ or organism. By means of example and not limitation, the level of the target may be modulated via alteration of the formation of the target (such as, e.g., folding, or interactions leading to formation of a complex), and/or the stability (e.g., the propensity of complex constituents to associate to a complex or disassociate from a complex), degradation or cellular localisation, etc. of the target.

The term "antisense" generally refers to a molecule designed to interfere with gene expression and capable of specifically binding to an intended target nucleic acid sequence. Antisense agents typically encompass an oligonucleotide or oligonucleotide analogue capable of specifically hybridising to the target sequence, and may typically comprise, consist essentially of or consist of a nucleic acid sequence that is complementary or substantially complementary to a sequence within genomic DNA, hnRNA, mRNA or cDNA, preferably mRNA or cDNA corresponding to the target nucleic acid. Antisense agents suitable herein may typically be capable of hybridising to their respective target at high stringency conditions, and may hybridise specifically to the target under physiological conditions.

The term "ribozyme" generally refers to a nucleic acid molecule, preferably an oligonucleotide or oligonucleotide analogue, capable of catalytically cleaving a polynucleotide. Preferably, a "ribozyme" may be capable of cleaving mRNA of a given target protein, thereby reducing translation thereof. Exemplary ribozymes contemplated herein include, without limitation, hammer head type ribozymes, ribozymes of the hairpin type, delta type ribozymes, etc. For teaching on ribozymes and design thereof, see, e.g., U.S. Pat. Nos. 5,354,855, 5,591,610, Pierce et al. 1998 (Nucleic Acids Res 26: 5093-5101), Lieber et al. 1995 (Mol Cell Biol 15: 540-551), and Benseler et al. 1993 (J Am Chem Soc 115: 8483-8484).

"RNA interference" or "RNAi" technology is routine in the art, and suitable RNAi agents intended herein may include inter alia short interfering nucleic acids (siNA), short interfering RNA (siRNA), double-stranded RNA (dsRNA), micro-RNA (miRNA), and short hairpin RNA (shRNA) molecules as known in the art. For teaching on RNAi molecules and design thereof, see inter alia Elbashir et al. 2001 (Nature 411: 494-501), Reynolds et al. 2004 (Nat Biotechnol 22: 326-30), Wang & Mu 2004 (Bioinformatics 20: 1818-20), Yuan et al. 2004 (Nucleic Acids Res 32(Web Server issue): W130-4), by M Sohail 2004 ("Gene Silencing by RNA Interference: Technology and Application", $1^{st}$ ed., CRC, ISBN 0849321417), U Schepers 2005 ("RNA Interference in Practice: Principles, Basics, and Methods for Gene Silencing in C.elegans, Drosophila, and Mammals", $1^{st}$ ed., Wiley-VCH, ISBN 3527310207), and DR Engelke & JJ Rossi 2005 ("Methods in Enzymology, Volume 392: RNA Interference", $1^{st}$ ed., Academic Press, ISBN 0121827976).

The term "pharmaceutically acceptable" as used herein is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colourants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

The present active substances (agents) may be used alone or in combination with any therapies known in the art for the disease and conditions as taught herein ("combination therapy"). Combination therapies as contemplated herein may comprise the administration of at least one active substance of the present invention and at least one other pharmaceutically or biologically active ingredient. Said present active substance(s) and said pharmaceutically or biologically active ingredient(s) may be administered in either the same or different pharmaceutical formulation(s), simultaneously or sequentially in any order.

The dosage or amount of the present active substances (agents) used, optionally in combination with one or more other active compound to be administered, depends on the individual case and is, as is customary, to be adapted to the individual circumstances to achieve an optimum effect. Thus, it depends on the nature and the severity of the disorder to be treated, and also on the sex, age, body weight, general health, diet, mode and time of administration, and individual responsiveness of the human or animal to be treated, on the route of administration, efficacy, metabolic stability and duration of action of the compounds used, on whether the therapy is acute or chronic or prophylactic, or on whether other active compounds are administered in addition to the agent(s) of the invention.

Without limitation, depending on the type and severity of the disease, a typical daily dosage might range from about 1 µg/kg to 100 mg/kg of body weight or more, depending on the factors mentioned above. For repeated administrations over several days or longer, depending on the condition, the treatment is sustained until a desired suppression of disease symptoms occurs. A preferred dosage of the active substance of the invention may be in the range from about 0.05 mg/kg to about 10 mg/kg of body weight. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every two or three weeks.

As used herein, a phrase such as "a subject in need of treatment" includes subjects that would benefit from treatment of a given disease or condition as taught herein. Such subjects may include, without limitation, those that have been diagnosed with said condition, those prone to contract or develop said condition and/or those in whom said condition is to be prevented.

The terms "treat" or "treatment" encompass both the therapeutic treatment of an already developed disease or condition, as well as prophylactic or preventative measures, wherein the aim is to prevent or lessen the chances of incidence of an undesired affliction, such as to prevent the chances of contraction and progression of a disease or condition as taught herein. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

The term "prophylactically effective amount" refers to an amount of an active compound or pharmaceutical agent that inhibits or delays in a subject the onset of a disorder as being sought by a researcher, veterinarian, medical doctor or other clinician. The term "therapeutically effective amount" as used herein, refers to an amount of active compound or pharmaceutical agent that elicits the biological or medicinal response in a subject that is being sought by a researcher, veterinarian, medical doctor or other clinician, which may include inter alia alleviation of the symptoms of the disease or condition being treated. Methods are known in the art for determining therapeutically and prophylactically effective doses for the present compounds.

The above aspects and embodiments are further supported by the following non-limiting examples.

EXAMPLES

Example 1

MASSTERMIND Discovery Platform for Discovery of New Biomarkers for PE

MASSTERMIND Experimental Setup

For biomarker discovery, we analysed the changes in protein expression using mass spectrometric detection of protein levels using our previously published COF-RADIC™ technology platform (substantially as described inter alia in WO 02/077016 and in Gevaert et al. 2003, Nat Biotechnol 21(5): 566-9).

All plasma samples were depleted for the most abundant proteins using commercially available affinity-based chromatographic columns (e.g. Agilent Technologies). Depletion efficiency of albumin and immunoglobulin G (IgG) was checked using Western Blot analysis. Samples were prepared for MASStermind analysis according to the standard N-terminal COFRADIC procedures. Samples and controls were differentially labelled by trypsin mediated incorporation of $^{18}O/^{16}O$ at the C-terminus of every tryptic peptide. After N-terminal peptide sorting, NanoLC separations followed by direct spotting onto MALDI targets were performed. MALDI-TOF/TOF instrumentation was used to generate MS spectra. The MS spectra were analyzed using in-house developed bioinformatics tools, such as tools for peak recognition and deisotoping, ratio determination between analyte and reference, clustering, inter-sample alignment and extensive sample quality control. Once all the samples were aligned and quality controlled, statistical analysis was initiated.

MASSTERMIND Statistical Analysis

To select for differential features (or peptides) that discriminate two populations, two different statistical measures were applied: one-rule classifier and Significance Analysis of Microarrays (SAM) analysis. Conceptually the simplest machine learning technique to find differential features is a one-rule classifier (oneR). In this method a simple rule of the form "If ratio<X then class=A else class=B" is generated for each feature. The performance of this rule on the data is determined by leave-one-out cross-validation. Features that show low error rates in this analysis are prime biomarker candidates. SAM (Tusher et al. 2001, PNAS 98: 5116-5121) is a method to select the most differential features, while controlling the False Discovery Rate (FDR). The method was originally developed for use in microarray experiments and proves applicable in Pronota's data matrices. The main advantage of this method over the one-rule classifier is that it will still allow to pick up useful trends when the difference in ratios between both classes start to diminish and random noise from the experiment starts to obscure the actual levels of the candidate markers. SAM calculates the relative difference in the ratio of features between two classes of samples. To estimate the significance of this score, a null distribution is estimated by permuting the class assignments of all samples and re-scoring. This gives us a confident estimation of the false discovery rat (FDR), that is the percentage of proteins or gene products that were identified by chance. To optimally account for missing values and intensity of the MS signal, the complete SAM analysis was run on different subsets of the data, using different cut-offs for these values. All results were compiled in a final report.

Example 2

Identification of Markers Useful in PE

The study design aimed to identify protein-based biomarkers allowing to discern pregnant women destined to develop preeclampsia (PE) later in their pregnancy (cases) from women that will not develop PE later in their pregnancy (controls).

Figure 17:
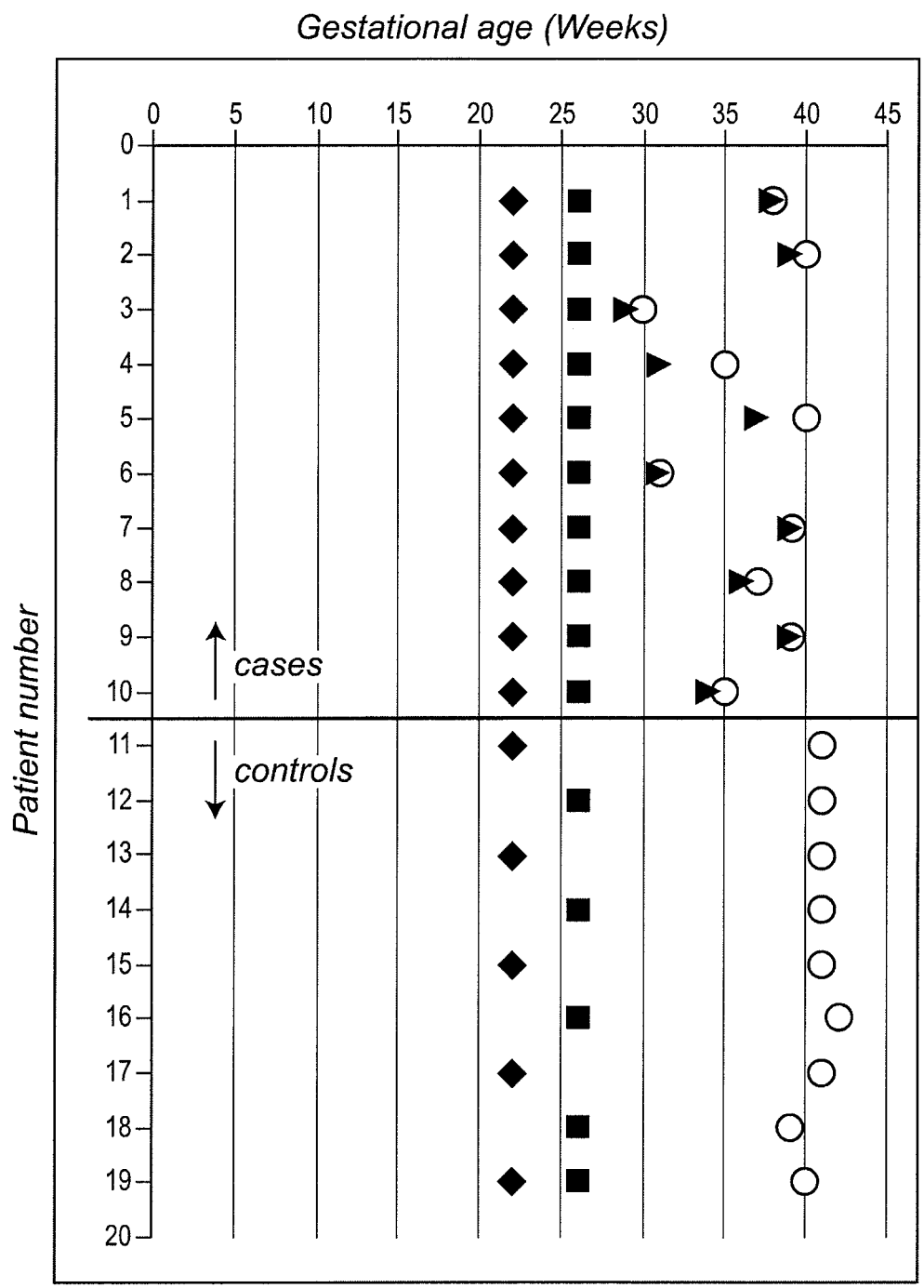
FIG. 17 illustrates the population of cases and controls. ◇ 22 weeks of gestation: 1st plasma sample is obtained; ■ 26 weeks of gestation: 2nd plasma sample is obtained; ≃ gestation time at which PE was clinically diagnosed within the cases; ○ gestation time when birth was given.

Plasma samples were obtained from pregnant women at two distinct time points within their pregnancy (22 and 26 weeks of gestation), i.e., 2 samples per individual were obtained (FIG. 17). At the time of sampling any clinical sign of later PE are still absent within the cases.

The MASStermind discovery study applied was a so-called "Reference design" wherein all samples were compared to a common reference, which constitutes a mixture of most samples used in the study.

Four groups of samples were defined: group 1 (PE-destined women at 22 weeks of gestation, n=10), group 2 (PE-destined women at 26 weeks of gestation, n=10), group 3 (control pregnant women at 22 weeks of gestation, n=5), and group 4 (control pregnant women at 26 weeks of gestation, n=5). The samples of groups 1 and 2 were obtained from the same individuals (i.e., paired). The samples of groups 3 and 4 were obtained from different individuals (i.e., unpaired, except 1). A few samples were excluded from the statistical analyses applied for biomarker candidate selection, such that n=9, 10, 5 and 4 for respectively groups 1, 2, 3 and 4.

Data analysis searched for population differences, i.e., populations were treated as a whole and differences were looked for between the mean quantity of markers between the control group and PE group, using the SAM and oneR statistical methods.

Various comparisons were made, including: group 1+2 vs. group 3+4; group 1 vs. group 3+4; group 2 vs. group 3+4; group 3 vs. group 4; group 3 vs. group 1+2+3+4; paired comparison (longitudinal trends) of group 2 and group 1. These were supplemented with manual selection for PE selectivity, pregnancy selectivity and consideration of time-to-diagnosis profiles.

Data for markers which behave differently between PE-destined and normal women, and are useful for the diagnosis, prediction, prognosis and/or monitoring PE, are shown in FIGS. 1 to 13. The data was based on assessment of peptides as listed in Table 1 above. Where more than 1 peptides were identified for a marker, they exhibited similar behaviour to the peptide retained.

The herein identified biomarkers displayed a variety of useful behaviours. Some markers were up-regulated or down regulated in PE groups compared to the controls at the 2 gestation time points considered. This effect could be independent from pregnancy (e.g., HGFL) or could be super-imposed on a pregnancy trend (e.g., ANGI). Some markers were up-regulated or down regulated in one of the PE groups compared to the controls at one of the 2 gestation time points considered (e.g., FBN2). Some markers were up-regulated or down regulated in one of the control groups compared to the PE groups at one of the 2 gestation time points considered (e.g., PGRP2). Some markers showed consistent up- or down-regulation within the same individual when considering the 2 gestation time points (i.e., longitudinal trends/slopes) (e.g., LCAP). Some markers showed an interesting time-to-diagnosis behaviour; for these cases the protein expressions is plotted in function of the time (# weeks) before the actual diagnosis of PE in FIGS. 12 and 13. Some markers showed combinations of the above behaviours.

Example 3

MASSTERCLASS Targeted Protein Quantification

The following describes one exemplary way of targeted protein quantification in samples.
MASSTERCLASS Experimental Setup MASSterclass assays use targeted tandem mass spectrometry with stable isotope dilution as an end-stage peptide quantitation system (also called Multiple Reaction Monitoring (MRM) and Single Reaction Monitoring (SRM)). The targeted peptide is specific (i.e., proteotypic) for the specific protein of interest. i.e., the amount of peptide measured is directly related to the amount of protein in the original sample (see, e.g., the peptides in Table 1). To reach the specificity and sensitivity needed for biomarker quantitation in complex samples, peptide fractionations precede the end-stage quantitation step.

A suitable MASSTERCLASS assay may include the following steps:
Plasma/serum sample
Depletion of human albumin and IgG (complexity reduction on protein level) using affinity capture with anti-albumin and anti-IgG antibodies using ProteoPrep spin columns (Sigma Aldrich)
Spiking of known amounts of isotopically labelled peptides. This peptide has the same amino acid sequence as the proteotypic peptide of interest, typically with one isotopically labelled amino acid built in to generate a mass difference. During the entire process, the labelled peptide has identical chemical and chromatographic behaviour as the endogenous peptide, except during the end-stage quantitation step which is based on molecular mass.
Tryptic digest. The proteins in the depleted serum/plasma sample are digested into peptides using trypsin. This enzyme cleaves proteins C-terminally from lysine and argninine, except when a proline is present C-terminally of the lysine or arginine. Before digestion, proteins are denatured by boiling, which renders the protein molecule more accessible for the trypsin activity during the 16 h incubation at 37° C.
First peptide-based fractionation: Free Flow Electrophoresis (FFE; BD Diagnostic) is a gel-free, fluid separation technique in which charged molecules moving in a continuous laminar flow are separated through an electrical field perpendicular to the flow. The electrical field causes the charged molecules to separate in the pH gradient according to their isoelectric point (ph. Only those fractions containing the monitored peptides are selected for further fractionation and LC-MS/MS analysis. Each peptide of interest elutes from the FFE chamber at a specific fraction number, which is determined during protein assay development using the synthetic peptide homologue. Specific fractions or fraction pools (multiplexing) proceed to the next level of fractionation.
Second peptide-based fractionation: Phenyl HPLC (XBridge Phenyl; Waters) separates peptides according to hydrophobicity and aromatic nature of amino acids present in the peptide sequence. Orthogonality with the back-end C18 separation is achieved by operating the column at an increased pH value (pH 10). As demonstrated by Gilar et al. 2005, J Sep Sci 28(14): 1694-1703), pH is by far the most drastic parameter to alter peptide selectivity in RP-HPLC. Each peptide of interest elutes from the Phenyl column at a specific retention time, which is determined during protein assay development using the synthetic peptide homologue. The use of an external control system, in which a mixture of 9 standard peptides is separated upfront a batch of sample separations, allows adjusting the fraction collection in order to correct for retention time shifts. The extent of fractionation is dependent on the concentration of the protein in the sample and the complexity of that sample.
LC-MS/MS based quantitation, including further separation on reversed phase (C18) nanoLC (PepMap C18; Dionex) and MS/MS: tandem mass spectrometry using MRM (4000 QTRAP; ABI)/SRM (Vantage TSQ; Thermo Scientific) mode. The LC column is connected to an electrospray needle connected to the source head of the mass spectrometer. As material elutes from the column, molecules are ionized and enter the mass spectrometer in the gas phase. The peptide that is monitored is specifically selected to pass the first quadrupole (Q1), based on its mass to charge ratio (m/z). The selected peptide is then fragmented in a second quadrupole (Q2) which is used as a collision cell. The resulting fragments then enter the third quadrupole (Q3). Depending on the instrument settings (determined during the assay development phase) only a specific peptide fragment or specific peptide fragments (or so called transitions) are selected for detection.
The combination of the m/z of the monitored peptide and the m/z of the monitored fragment of this peptide is called a transition. This process can be performed for multiple transitions during one experiment. Both the endogenous peptide (analyte) and its corresponding isotopically labelled synthetic peptide (internal standard) elute at the same retention time, and are measured in the same LC-MS/MS experiment.
The MASSTERCLASS readout is defined by the ratio between the area under the peak specific for the analyte and the area under the peak specific for the synthetic isotopically labelled analogue (internal standard). The readouts are directly related to the original concentration of the protein in the sample. The readouts can therefore be compared between different samples and groups of samples.

A typical MASSTERCLASS protocol for targeted peptide quantitation may be as follows:
25 µL of plasma is subjected to a depletion of human albumin and IgG (ProteoPrep spin columns; Sigma Aldrich) according to the manufacturer's protocol, except that 20 mM $NH_4HCO_3$ is used as the binding/equilibration buffer.
The depleted sample (225 µL) is denatured for 15 min at 95° C. and immediately cooled on ice 500 fmol of the isotopically labelled peptide (custom made 'Heavy AQUA' peptide; Thermo Scientific) is spiked in the sample 20 µg trypsin is added to the sample and digestion is allowed for 16 h at 37° C.

The digested sample is first diluted 1/8 in solvent A (0.1% formic acid) and then 1/20 in the same solvent containing 250 amol/µL of all isotopically labelled peptides (custom made 'Heavy AQUA' peptide; Thermo Scientific) of interest.

20 µL of the final dilution is separated using reverse-phase NanoLC with on-line MS/MS in MRM/SRM mode:

Column: PepMap C18, 75 µm I.D.×25 cm L, 100 Å pore diameter, 5 µm particle size

Solvent A: 0.1% formic acid

Solvent B: 80% acetonitrile, 0.1% formic acid

Gradient: 30 min; 2%-55% Solvent B

MS/MS in MRM mode: method contains the transitions for the analyte as well as for the synthetic, labelled peptide.

The used transitions are experimentally determined and selected during protein assay development Each of the transitions of interest is measured for a period starting 3 minutes before and ending 3 minutes after the determined retention time of the peptide of interest, making sure that each peak has at least 15 datapoints.

The raw data is analysed and quantified using the LCQuan software (Thermo Scientific): the area under the analyte peak and under the internal standard peak at the same C18 retention time is determined by automatic peak detection. These are cross-checked manually.

The MASSterclass readout is defined by the ratio of the analyte peak area and the internal standard peak area. The measured ratios are differential quantitations of peptides. In other words a ratio is the normalised concentration of a peptide. The concentration of a peptide is proportional to the ratio measured in the mass spectrometer.

What is claimed is:

1. A method for identifying and treating preeclampsia (PE) in a pregnant human female not manifesting hypertension, comprising;
   (a) identifying the pregnant human female in need of treatment by having an assay conducted, wherein the assay comprises:
      (i) measuring the quantity of insulin-like growth factor-binding protein complex acid labile chain (ALS) in a sample from the pregnant human female, wherein the pregnant human female does not have active hypertensive disorder of pregnancy (HDP) or PE and does not manifest hypertension;
      (ii) comparing the quantity of ALS measured in (i) with a reference value of the quantity of ALS, said reference value representing the level of ALS in healthy pregnant human females, wherein said pregnant human female is at risk of developing PE when the quantity of ALS measured is elevated compared to the reference value;
      (iii) finding an elevated quantity of ALS measured in (i) from the reference value in the pregnant human female; and
   (b) administering to the pregnant human female having the elevated quantity of ALS for PE an anti-hypertensive treatment selected from the group consisting of beta-blockers, calcium channel blockers, vasodilators and DOPA decarboxylase inhibitors, whereby PE is treated in the pregnant human female.

2. The method according to claim 1, wherein ALS is measured at two different time points.

3. The method according to claim 1, wherein the subject does not yet suffer from clinically manifest PE and whereby the probability, chance or risk that the subject will develop clinically manifest PE is predicted.

4. The method according to claim 1, whereby gestational or postpartum age of onset and/or time remaining to onset of PE is predicted.

5. The method according to claim 1, wherein the method further comprises measuring the presence or absence and/or quantity of one or more other biomarkers useful for the prediction of PE selected from the group consisting of soluble fms-like tyrosine kinase-1 (sFlt-1, sVEGFR-1), placental growth factor and vascular endothelial growth factor (VEGF).

6. The method according to claim 1, further comprising determining the presence or absence and/or level of one or more risk factors for PE in the subject.

7. The method according to claim 6, wherein the one or more risk factor for PE is selected from nulliparity, multiple gestation, prolonged interval between pregnancies, history of PE in a prior pregnancy or family history of PE, extremes in age (<20 years and >40 years), obesity, chronic hypertension, chronic renal disease, migraine, headaches, (gestational) diabetes mellitus, polycystic ovarian syndrome, autoimmune disorders such as lupus, rheumatoid arthritis, sarcoidosis or multiple sclerosis (MS), vascular or connective tissue diseases, vitamin D insufficiency, antiphospholipid antibody syndrome or inherited thrombophilia, male partner whose previous partner had PE, hydrops fetalis and unexplained foetal intrauterine growth restriction.

8. The method according to claim 5, wherein the quantity of ALS and/or the presence or absence and/or quantity of the one or more other biomarkers is measured using a binding agent capable of specifically binding to the respective biomarkers and/or to fragments thereof.

9. The method according to claim 5, wherein the quantity of ALS and/or the presence or absence and/or quantity of the one or more other biomarkers is measured using an immunoassay technology, or using a mass spectrometry analysis method or using a chromatography method, or using a combination of said methods.

10. The method of claim 1, wherein the DOPA decarboxylase inhibitor is selected from the group consisting of smethyldopa, labetalol, acebutolol, metoprolol, pindolol, propranolol, nifedipine, isradipine and/or hydralazine, and $MgSO_4$.

11. The method of claim 1, wherein the method further comprises measuring the presence or absence and/or quantity of Endoglin.

* * * * *

SEQUENCE LISTING

```
<160> NUMBER OF SEQ ID NOS: 33

<210> SEQ ID NO 1
<211> LENGTH: 11
<212> TYPE: PRT
<213> ORGANISM: Homo sapiens

<400> SEQUENCE: 1

Gln Gly Lys Asp Leu Glu Lys Val Lys Gln Arg
1               5                   10

<210> SEQ ID NO 2
<211> LENGTH: 17
<212> TYPE: PRT
<213> ORGANISM: Homo sapiens

<400> SEQUENCE: 2

Leu Thr Ser Pro Cys Lys Asp Ile Asn Thr Phe Ile His Gly Asn Lys
1               5                   10                  15

Arg

<210> SEQ ID NO 3
<211> LENGTH: 36
<212> TYPE: PRT
<213> ORGANISM: Homo sapiens

<400> SEQUENCE: 3

Ala Asp Pro Gly Thr Pro Gly Glu Ala Glu Gly Pro Ala Cys Pro Ala
1               5                   10                  15

Ala Cys Val Cys Ser Tyr Asp Asp Ala Asp Glu Leu Ser Val Phe
            20                  25                  30

Cys Ser Ser Arg
        35

<210> SEQ ID NO 4
<211> LENGTH: 16
<212> TYPE: PRT
<213> ORGANISM: Homo sapiens

<400> SEQUENCE: 4

Pro Thr Glu Leu Ser Asn Pro Gln Phe Ile Val Asp Gly Ala Thr Arg
1               5                   10                  15
```

<210> SEQ ID NO 5
<211> LENGTH: 23
<212> TYPE: PRT
<213> ORGANISM: Homo sapiens

<400> SEQUENCE: 5

Ile Pro Val Ile Glu Pro Ser Val Pro Glu Leu Val Val Lys Pro Gly
1               5                   10                  15

Ala Thr Val Thr Glu Leu Arg
            20

<210> SEQ ID NO 6
<211> LENGTH: 8
<212> TYPE: PRT
<213> ORGANISM: Homo sapiens

<400> SEQUENCE: 6

Phe Gly Gln Thr Asp Met Ser Arg
1               5

<210> SEQ ID NO 7
<211> LENGTH: 8
<212> TYPE: PRT
<213> ORGANISM: Homo sapiens

<400> SEQUENCE: 7

Val Gln Thr Val Pro Leu Ser Arg
1               5

<210> SEQ ID NO 8
<211> LENGTH: 11
<212> TYPE: PRT
<213> ORGANISM: Homo sapiens

<400> SEQUENCE: 8

His Trp Pro Ser Glu Pro Ser Glu Ala Val Arg
1               5                   10

<210> SEQ ID NO 9
<211> LENGTH: 13
<212> TYPE: PRT
<213> ORGANISM: Homo sapiens

<400> SEQUENCE: 9

Gln Val Tyr Gln Lys Gly Leu Gln Asp Val Asn Leu Arg
1               5                   10

<210> SEQ ID NO 10
<211> LENGTH: 10
<212> TYPE: PRT
<213> ORGANISM: Homo sapiens

<400> SEQUENCE: 10

Ala Trp Ile Thr Ala Pro Val Ala Leu Arg
1               5                   10

<210> SEQ ID NO 11
<211> LENGTH: 11
<212> TYPE: PRT
<213> ORGANISM: Homo sapiens

<400> SEQUENCE: 11

Ser Glu Gly Gly Phe Thr Ala Thr Gly Gln Arg

```
<210> SEQ ID NO 12
<211> LENGTH: 14
<212> TYPE: PRT
<213> ORGANISM: Homo sapiens

<400> SEQUENCE: 12

Glu Thr Val His Cys Asp Leu Gln Pro Val Gly Pro Glu Arg
1               5                   10

<210> SEQ ID NO 13
<211> LENGTH: 14
<212> TYPE: PRT
<213> ORGANISM: Homo sapiens

<400> SEQUENCE: 13

Ser Met Tyr Asp Pro Val Phe Asp Ala Thr Phe His Leu Arg
1               5                   10

<210> SEQ ID NO 14
<211> LENGTH: 13
<212> TYPE: PRT
<213> ORGANISM: Homo sapiens

<400> SEQUENCE: 14

Asp Val Leu Leu Glu Ala Cys Cys Ala Asp Gly His Arg
1               5                   10

<210> SEQ ID NO 15
<211> LENGTH: 14
<212> TYPE: PRT
<213> ORGANISM: Homo sapiens

<400> SEQUENCE: 15

Cys Asn Cys Asn Ser Gly Tyr Glu Pro Asp Ala Ser Gly Arg
1               5                   10

<210> SEQ ID NO 16
<211> LENGTH: 11
<212> TYPE: PRT
<213> ORGANISM: Homo sapiens

<400> SEQUENCE: 16

Thr His Phe Gly Val Leu Met Asp Leu Pro Arg
1               5                   10

<210> SEQ ID NO 17
<211> LENGTH: 10
<212> TYPE: PRT
<213> ORGANISM: Homo sapiens

<400> SEQUENCE: 17

Ser Pro Leu Asn Asp Phe Gln Val Leu Arg
1               5                   10

<210> SEQ ID NO 18
<211> LENGTH: 18
<212> TYPE: PRT
<213> ORGANISM: Homo sapiens

<400> SEQUENCE: 18

Gln Pro Ala Val Glu Glu Pro Ala Glu Val Thr Ala Thr Val Leu Ala
1               5                   10                  15
```

Ser Arg

<210> SEQ ID NO 19
<211> LENGTH: 10
<212> TYPE: PRT
<213> ORGANISM: Homo sapiens

<400> SEQUENCE: 19

Glu Lys Val Ala Ser Val Gly Asn Ser Arg
1               5                   10

<210> SEQ ID NO 20
<211> LENGTH: 13
<212> TYPE: PRT
<213> ORGANISM: Homo sapiens

<400> SEQUENCE: 20

Ala Thr Asn Gly Lys Leu Phe Pro Trp Ala Gln Ile Arg
1               5                   10

<210> SEQ ID NO 21
<211> LENGTH: 8
<212> TYPE: PRT
<213> ORGANISM: Homo sapiens

<400> SEQUENCE: 21

Gln Pro Gln Ala Trp Lys Asp Arg
1               5

<210> SEQ ID NO 22
<211> LENGTH: 12
<212> TYPE: PRT
<213> ORGANISM: Homo sapiens

<400> SEQUENCE: 22

Ser Ile Val Pro Gln Gly Gly Ser His Ser Leu Arg
1               5                   10

<210> SEQ ID NO 23
<211> LENGTH: 14
<212> TYPE: PRT
<213> ORGANISM: Homo sapiens

<400> SEQUENCE: 23

Ala Gly Leu Leu Arg Pro Asp Tyr Ala Leu Leu Gly His Arg
1               5                   10

<210> SEQ ID NO 24
<211> LENGTH: 12
<212> TYPE: PRT
<213> ORGANISM: Homo sapiens

<400> SEQUENCE: 24

Cys Gly Leu Ser Thr His Val Glu Ile Gly His Arg
1               5                   10

<210> SEQ ID NO 25
<211> LENGTH: 11
<212> TYPE: PRT
<213> ORGANISM: Homo sapiens

<400> SEQUENCE: 25

Gln Ile Thr Val Asn Asp Leu Pro Val Gly Arg
1               5                   10

```
<210> SEQ ID NO 26
<211> LENGTH: 16
<212> TYPE: PRT
<213> ORGANISM: Homo sapiens

<400> SEQUENCE: 26

Pro Thr Leu Ser Val Gln Gln Thr Pro Glu Gly Ser Leu Leu Ala Arg
1               5                   10                  15

<210> SEQ ID NO 27
<211> LENGTH: 23
<212> TYPE: PRT
<213> ORGANISM: Homo sapiens

<400> SEQUENCE: 27

Gln Asp Ser Pro Pro Gln Ile Leu Val His Pro Gln Asp Gln Leu Phe
1               5                   10                  15

Gln Gly Pro Gly Pro Ala Arg
            20

<210> SEQ ID NO 28
<211> LENGTH: 9
<212> TYPE: PRT
<213> ORGANISM: Homo sapiens

<400> SEQUENCE: 28

Thr Cys Lys Met Ser Gln Leu Glu Arg
1               5

<210> SEQ ID NO 29
<211> LENGTH: 15
<212> TYPE: PRT
<213> ORGANISM: Homo sapiens

<400> SEQUENCE: 29

Ser Phe Phe Lys Glu Ala Leu Gln Gly Val Gly Asp Met Gly Arg
1               5                   10                  15

<210> SEQ ID NO 30
<211> LENGTH: 19
<212> TYPE: PRT
<213> ORGANISM: Homo sapiens

<400> SEQUENCE: 30

Ala Glu Gly Thr Thr Gly Leu Ala Pro Ala Gly Gln Thr Ser Glu Glu
1               5                   10                  15

Ser Arg Pro

<210> SEQ ID NO 31
<211> LENGTH: 18
<212> TYPE: PRT
<213> ORGANISM: Homo sapiens

<400> SEQUENCE: 31

Glu Glu Tyr Val Gly Leu Ser Ala Asn Gln Cys Ala Val Pro Ala Lys
1               5                   10                  15

Asp Arg

<210> SEQ ID NO 32
<211> LENGTH: 10
<212> TYPE: PRT
<213> ORGANISM: Homo sapiens
```

<400> SEQUENCE: 32

Gln Gln Gln Asp Leu Met Pro Gln Cys Arg
1               5                   10

<210> SEQ ID NO 33
<211> LENGTH: 605
<212> TYPE: PRT
<213> ORGANISM: Homo sapiens

<400> SEQUENCE: 33

Met Ala Leu Arg Lys Gly Gly Leu Ala Leu Ala Leu Leu Leu Leu Ser
1               5                   10                  15

Trp Val Ala Leu Gly Pro Arg Ser Leu Glu Gly Ala Asp Pro Gly Thr
            20                  25                  30

Pro Gly Glu Ala Glu Gly Pro Ala Cys Pro Ala Ala Cys Val Cys Ser
        35                  40                  45

Tyr Asp Asp Asp Ala Asp Glu Leu Ser Val Phe Cys Ser Ser Arg Asn
    50                  55                  60

Leu Thr Arg Leu Pro Asp Gly Val Pro Gly Gly Thr Gln Ala Leu Trp
65                  70                  75                  80

Leu Asp Gly Asn Asn Leu Ser Ser Val Pro Pro Ala Ala Phe Gln Asn
                85                  90                  95

Leu Ser Ser Leu Gly Phe Leu Asn Leu Gln Gly Gly Gln Leu Gly Ser
            100                 105                 110

Leu Glu Pro Gln Ala Leu Leu Gly Leu Glu Asn Leu Cys His Leu His
        115                 120                 125

Leu Glu Arg Asn Gln Leu Arg Ser Leu Ala Leu Gly Thr Phe Ala His
    130                 135                 140

Thr Pro Ala Leu Ala Ser Leu Gly Leu Ser Asn Asn Arg Leu Ser Arg
145                 150                 155                 160

Leu Glu Asp Gly Leu Phe Glu Gly Leu Gly Ser Leu Trp Asp Leu Asn
                165                 170                 175

Leu Gly Trp Asn Ser Leu Ala Val Leu Pro Asp Ala Ala Phe Arg Gly
            180                 185                 190

Leu Gly Ser Leu Arg Glu Leu Val Leu Ala Gly Asn Arg Leu Ala Tyr
        195                 200                 205

Leu Gln Pro Ala Leu Phe Ser Gly Leu Ala Glu Leu Arg Glu Leu Asp
    210                 215                 220

Leu Ser Arg Asn Ala Leu Arg Ala Ile Lys Ala Asn Val Phe Val Gln
225                 230                 235                 240

Leu Pro Arg Leu Gln Lys Leu Tyr Leu Asp Arg Asn Leu Ile Ala Ala
                245                 250                 255

Val Ala Pro Gly Ala Phe Leu Gly Leu Lys Ala Leu Arg Trp Leu Asp
            260                 265                 270

Leu Ser His Asn Arg Val Ala Gly Leu Leu Glu Asp Thr Phe Pro Gly
        275                 280                 285

Leu Leu Gly Leu Arg Val Leu Arg Leu Ser His Asn Ala Ile Ala Ser
    290                 295                 300

Leu Arg Pro Arg Thr Phe Lys Asp Leu His Phe Leu Glu Glu Leu Gln
305                 310                 315                 320

Leu Gly His Asn Arg Ile Arg Gln Leu Ala Glu Arg Ser Phe Glu Gly
                325                 330                 335

Leu Gly Gln Leu Glu Val Leu Thr Leu Asp His Asn Gln Leu Gln Glu
            340                 345                 350

-continued

```
Val Lys Ala Gly Ala Phe Leu Gly Leu Thr Asn Val Ala Val Met Asn
        355                 360                 365
Leu Ser Gly Asn Cys Leu Arg Asn Leu Pro Glu Gln Val Phe Arg Gly
    370                 375                 380
Leu Gly Lys Leu His Ser Leu His Leu Glu Gly Ser Cys Leu Gly Arg
385             390                 395                 400
Ile Arg Pro His Thr Phe Thr Gly Leu Ser Gly Leu Arg Arg Leu Phe
                405                 410                 415
Leu Lys Asp Asn Gly Leu Val Gly Ile Glu Glu Gln Ser Leu Trp Gly
            420                 425                 430
Leu Ala Glu Leu Leu Glu Leu Asp Leu Thr Ser Asn Gln Leu Thr His
        435                 440                 445
Leu Pro His Arg Leu Phe Gln Gly Leu Gly Lys Leu Glu Tyr Leu Leu
    450                 455                 460
Leu Ser Arg Asn Arg Leu Ala Glu Leu Pro Ala Asp Ala Leu Gly Pro
465                 470                 475                 480
Leu Gln Arg Ala Phe Trp Leu Asp Val Ser His Asn Arg Leu Glu Ala
                485                 490                 495
Leu Pro Asn Ser Leu Leu Ala Pro Leu Gly Arg Leu Arg Tyr Leu Ser
            500                 505                 510
Leu Arg Asn Asn Ser Leu Arg Thr Phe Thr Pro Gln Pro Pro Gly Leu
        515                 520                 525
Glu Arg Leu Trp Leu Glu Gly Asn Pro Trp Asp Cys Gly Cys Pro Leu
    530                 535                 540
Lys Ala Leu Arg Asp Phe Ala Leu Gln Asn Pro Ser Ala Val Pro Arg
545                 550                 555                 560
Phe Val Gln Ala Ile Cys Glu Gly Asp Asp Cys Gln Pro Pro Ala Tyr
                565                 570                 575
Thr Tyr Asn Asn Ile Thr Cys Ala Ser Pro Pro Glu Val Val Gly Leu
            580                 585                 590
Asp Leu Arg Asp Leu Ser Glu Ala His Phe Ala Pro Cys
        595                 600                 605
```